(12) United States Patent
Dalebout et al.

(10) Patent No.: US 10,258,828 B2
(45) Date of Patent: Apr. 16, 2019

(54) CONTROLS FOR AN EXERCISE DEVICE

(71) Applicant: ICON Health & Fitness, Inc., Logan, UT (US)

(72) Inventors: William T. Dalebout, North Logan, UT (US); Gordon Cutler, Providence, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 377 days.

(21) Appl. No.: 14/997,017

(22) Filed: Jan. 15, 2016

(65) Prior Publication Data

US 2016/0206922 A1    Jul. 21, 2016

Related U.S. Application Data

(60) Provisional application No. 62/104,146, filed on Jan. 16, 2015.

(51) Int. Cl.
| | |
|---|---|
| *A63B 24/00* | (2006.01) |
| *A63B 22/02* | (2006.01) |
| *A63B 71/06* | (2006.01) |
| *G06F 19/00* | (2018.01) |
| *A63B 21/22* | (2006.01) |
| *A63B 22/00* | (2006.01) |
| *A63B 22/06* | (2006.01) |

(52) U.S. Cl.
CPC .......... *A63B 24/0087* (2013.01); *A63B 22/02* (2013.01); *A63B 71/0622* (2013.01); *G06F 19/3481* (2013.01); *A63B 21/225* (2013.01); *A63B 22/0023* (2013.01); *A63B 22/0235* (2013.01); *A63B 22/0605* (2013.01); *A63B 22/0664* (2013.01); *A63B 2022/0278* (2013.01); *A63B 2024/0093* (2013.01); *A63B 2071/068* (2013.01); *A63B 2071/0625* (2013.01); *A63B 2071/0638* (2013.01); *A63B 2071/0677* (2013.01); *A63B 2220/40* (2013.01); *A63B 2220/801* (2013.01); *A63B 2220/806* (2013.01); *A63B 2225/50* (2013.01); *A63B 2225/685* (2013.01); *A63B 2230/062* (2013.01); *A63B 2230/207* (2013.01); *A63B 2230/30* (2013.01); *A63B 2230/40* (2013.01); *A63B 2230/60* (2013.01)

(58) Field of Classification Search
None
See application file for complete search history.

(56) References Cited

U.S. PATENT DOCUMENTS

| | | |
|---|---|---|
| 232,022 A | 9/1880 | Gifford |
| 284,294 A | 9/1883 | Graves |

(Continued)

*Primary Examiner* — Stephen R Crow
(74) *Attorney, Agent, or Firm* — Ray Quinney & Nebeker

(57) ABSTRACT

An exercise machine includes a frame, a movable element that is movable in the performance of an exercise where the movable element has at least one selectively adjustable operating parameter that selectively alters a difficulty of the exercise, and a recall mechanism connected to the frame. The exercise machine also includes a processor and memory where the memory has programmed instructions executable by the processor to apply a first difficulty setting of the selectively adjustable operating parameter to the movable element and reapply the first difficulty setting to the movable element based on activation of the recall mechanism.

20 Claims, 6 Drawing Sheets

(56) References Cited

U.S. PATENT DOCUMENTS

| | | |
|---|---|---|
| 321,388 A | 6/1885 | Ruebsam |
| 339,638 A | 4/1886 | Goldie |
| 421,779 A | 2/1890 | Steven |
| 447,780 A | 3/1891 | Luge |
| 450,792 A | 4/1891 | Dodd |
| 659,216 A | 10/1900 | Dowling |
| 663,486 A | 12/1900 | Boren |
| 674,391 A | 5/1901 | Baker |
| 683,284 A | 9/1901 | Honey |
| 766,930 A | 8/1904 | Clemons |
| 881,521 A | 3/1908 | Wilson |
| 897,722 A | 9/1908 | Day |
| 931,394 A | 8/1909 | Day |
| 937,795 A | 10/1909 | Hackney |
| 1,016,729 A | 2/1912 | Barrett |
| 1,020,777 A | 3/1912 | Peterson |
| 1,064,968 A | 6/1913 | Hagen |
| 1,082,940 A | 12/1913 | Flora |
| 1,211,765 A | 1/1917 | Schmidt |
| 1,570,482 A | 1/1926 | Hale |
| 1,580,530 A | 4/1926 | Rambo |
| 1,585,748 A | 5/1926 | Wendelken |
| 1,715,870 A | 6/1929 | Augustine |
| 1,766,089 A | 6/1930 | Wood |
| 1,778,635 A | 10/1930 | Heisler |
| 1,824,406 A | 9/1931 | Petersime |
| 1,850,530 A | 3/1932 | Brown |
| 1,893,728 A | 1/1933 | Bullis |
| 1,902,694 A | 3/1933 | Edwards |
| 1,919,627 A | 7/1933 | Fitzgerald |
| 1,928,089 A | 9/1933 | Blickman |
| 1,973,945 A | 9/1934 | Chavin |
| 1,978,579 A | 10/1934 | Hooks |
| 1,982,843 A | 12/1934 | Traver |
| 2,067,136 A | 1/1937 | Bridenbaugh |
| 2,117,957 A | 5/1938 | Ritter |
| 2,165,700 A | 7/1939 | Glynn |
| 2,177,957 A | 10/1939 | Stewart |
| 2,219,219 A | 10/1940 | Boger |
| 2,247,946 A | 7/1941 | Hein et al. |
| 2,255,864 A | 9/1941 | Stephens |
| 2,315,485 A | 4/1943 | Le Roy |
| 2,399,915 A | 5/1946 | Drake |
| 2,440,644 A | 4/1948 | Powell |
| 2,569,007 A | 9/1951 | Klyce |
| 2,632,645 A | 3/1953 | Barkschat |
| 2,645,539 A | 7/1953 | Thompson |
| 2,646,282 A | 7/1953 | Ringman |
| 2,648,540 A | 8/1953 | Hunter |
| 2,674,453 A | 4/1954 | Hummert |
| 2,743,623 A | 5/1956 | Wells |
| 2,746,822 A | 5/1956 | Copenhaver |
| 2,842,365 A | 7/1958 | Kelley |
| 2,855,200 A | 10/1958 | Blickman |
| 2,874,971 A | 2/1959 | Devery |
| 2,969,060 A | 1/1961 | Swanda |
| 2,984,594 A | 5/1961 | Runton |
| 3,035,671 A | 5/1962 | Sicherman |
| 3,059,312 A | 10/1962 | Jamieson |
| 3,068,950 A | 12/1962 | Davidson |
| 3,072,426 A | 1/1963 | Gilbert |
| 3,112,108 A | 11/1963 | Hanke |
| 3,127,171 A | 3/1964 | Noland et al. |
| 3,179,071 A | 4/1965 | Johnston |
| 3,193,287 A | 7/1965 | Robinson |
| 3,205,888 A | 9/1965 | Stroop |
| 3,316,898 A | 5/1967 | Brown |
| 3,319,273 A | 5/1967 | Solin |
| 3,342,485 A | 9/1967 | Gaul |
| 3,345,067 A | 10/1967 | Smith |
| 3,358,813 A | 12/1967 | Kohlhagen |
| 3,378,259 A | 4/1968 | Kupchinski |
| 3,408,067 A | 10/1968 | Armstrong |
| 3,408,069 A | 10/1968 | Lewis |
| 3,411,497 A | 11/1968 | Rickey et al. |
| 3,416,174 A | 12/1968 | Novitske |
| 3,430,507 A | 3/1969 | Hurst et al. |
| 3,438,627 A | 4/1969 | La Lanne |
| 3,444,830 A | 5/1969 | Doetsch |
| 3,446,503 A | 5/1969 | Lawton |
| 3,501,140 A | 3/1970 | Eichorn |
| 3,511,500 A | 5/1970 | Dunn |
| 3,514,110 A | 5/1970 | Thomander |
| 3,518,985 A | 7/1970 | Quinton |
| 3,547,435 A | 12/1970 | Scott |
| 3,554,541 A | 1/1971 | Spoth |
| 3,563,541 A | 2/1971 | Sanquist |
| 3,566,861 A | 3/1971 | Weiss |
| 3,567,219 A | 3/1971 | Foster |
| 3,568,669 A | 3/1971 | Stites |
| 3,572,700 A | 3/1971 | Mastropaolo |
| 3,583,465 A | 6/1971 | Youngs et al. |
| 3,586,322 A | 6/1971 | Kverneland |
| 3,589,715 A | 6/1971 | Mark |
| 3,592,466 A | 7/1971 | Parsons |
| 3,598,404 A | 8/1971 | Bowman |
| 3,602,502 A | 8/1971 | Jaegar |
| 3,606,320 A | 9/1971 | Erwin, Jr. |
| 3,608,898 A | 9/1971 | Berlin |
| 3,614,097 A | 10/1971 | Blickman |
| 3,628,654 A | 12/1971 | Haracz |
| 3,628,791 A | 12/1971 | Garcia |
| 3,634,895 A | 1/1972 | Childers |
| 3,636,577 A | 1/1972 | Nissen |
| 3,638,941 A | 2/1972 | Kulkens |
| 3,640,528 A | 2/1972 | Proctor |
| 3,641,601 A | 2/1972 | Sieg |
| 3,642,279 A | 2/1972 | Cutter |
| 3,643,943 A | 2/1972 | Erwin, Jr. et al. |
| 3,650,529 A | 3/1972 | Salm |
| 3,658,327 A | 4/1972 | Thiede |
| 3,659,845 A | 5/1972 | Quinton |
| 3,664,666 A | 5/1972 | Lloyd |
| 3,686,776 A | 8/1972 | Dahl |
| 3,689,066 A | 9/1972 | Hagen |
| 3,703,284 A | 11/1972 | Hesen |
| 3,708,166 A | 1/1973 | Annas |
| 3,709,197 A | 1/1973 | Moseley |
| 3,731,917 A | 5/1973 | Townsend |
| 3,738,649 A | 6/1973 | Miller |
| 3,741,538 A | 6/1973 | Useldinger |
| 3,751,033 A | 8/1973 | Rosenthal |
| 3,756,595 A | 9/1973 | Hague |
| 3,788,412 A | 1/1974 | Vincent |
| 3,792,860 A | 2/1974 | Seines |
| 3,809,393 A | 5/1974 | Jones |
| 3,814,420 A | 6/1974 | Encke |
| 3,822,488 A | 7/1974 | Johnson |
| 3,826,491 A | 7/1974 | Elder |
| 3,848,467 A | 11/1974 | Flavell |
| 3,851,874 A | 12/1974 | Wilkin |
| 3,858,938 A | 1/1975 | Kristensson et al. |
| 3,861,215 A | 1/1975 | Bradley |
| 3,869,121 A | 3/1975 | Flavell |
| 3,870,297 A | 3/1975 | Elder |
| 3,874,657 A | 4/1975 | Niebojewski |
| 3,880,274 A | 4/1975 | Bechtloff |
| 3,883,922 A | 5/1975 | Fleischhauer |
| 3,892,404 A | 7/1975 | Martucci |
| 3,901,379 A | 8/1975 | Bruhm |
| 3,903,613 A | 9/1975 | Bisberg |
| 3,904,196 A | 9/1975 | Berlin |
| 3,909,857 A | 10/1975 | Herrera |
| 3,912,263 A | 10/1975 | Yatso |
| 3,918,710 A | 11/1975 | Niebojewski |
| 3,926,430 A | 12/1975 | Good |
| 3,929,026 A | 12/1975 | Hofmann |
| 3,938,400 A | 2/1976 | Konyha |
| 3,941,377 A | 3/1976 | Lie |
| 3,948,513 A | 4/1976 | Pfotenhauer |
| 3,963,101 A | 6/1976 | Stadelmann et al. |
| 3,977,451 A | 8/1976 | Duba |
| 3,981,500 A | 9/1976 | Ryan |
| 4,012,015 A | 3/1977 | Nelson et al. |

(56) References Cited

U.S. PATENT DOCUMENTS

| | | |
|---|---|---|
| 4,024,949 A | 5/1977 | Kleysteuber et al. |
| 4,026,545 A | 5/1977 | Schonenberger |
| 4,033,567 A | 7/1977 | Lipfert |
| 4,056,265 A | 11/1977 | Ide |
| 4,063,726 A | 12/1977 | Wilson |
| 4,063,727 A | 12/1977 | Hall |
| 4,066,257 A | 1/1978 | Moller |
| 4,066,259 A | 1/1978 | Brentham |
| 4,067,372 A | 1/1978 | Masson |
| 4,072,309 A | 2/1978 | Wilson |
| 4,077,626 A | 3/1978 | Newman |
| 4,082,267 A | 4/1978 | Flavell |
| 4,093,196 A | 6/1978 | Bauer |
| 4,094,330 A | 6/1978 | Jong |
| 4,111,417 A | 9/1978 | Gardner |
| 4,113,071 A | 9/1978 | Muller et al. |
| 4,120,294 A | 10/1978 | Wolfe |
| 4,141,158 A | 2/1979 | Benseler et al. |
| 4,146,222 A | 3/1979 | Hribar |
| 4,149,714 A | 4/1979 | Lambert, Jr. |
| 4,151,988 A | 5/1979 | Nabinger |
| 4,151,994 A | 5/1979 | Stalberger, Jr. |
| 4,161,998 A | 7/1979 | Trimble |
| 4,167,938 A | 9/1979 | Remih |
| 4,168,061 A | 9/1979 | Gordon |
| 4,171,805 A | 10/1979 | Abbott |
| 4,179,134 A | 12/1979 | Atkinson |
| 4,183,156 A | 1/1980 | Rudy |
| 4,183,494 A | 1/1980 | Cleveland |
| 4,188,030 A | 2/1980 | Hooper |
| 4,199,139 A | 4/1980 | Mahnke |
| 4,204,673 A | 5/1980 | Speer, Sr. |
| 4,208,049 A | 6/1980 | Wilson |
| 4,215,516 A | 8/1980 | Huschle et al. |
| 4,216,856 A | 8/1980 | Moring et al. |
| 4,227,689 A | 10/1980 | Keiser |
| 4,235,437 A | 11/1980 | Ruis et al. |
| 4,240,627 A | 12/1980 | Brentham |
| 4,248,476 A | 2/1981 | Phelps |
| 4,249,725 A | 2/1981 | Mattox |
| 4,251,932 A | 2/1981 | Love |
| 4,253,661 A | 3/1981 | Russell |
| 4,258,821 A | 3/1981 | Wendt |
| 4,258,913 A | 3/1981 | Brentham |
| 4,274,625 A | 6/1981 | Gaetano |
| 4,278,095 A | 7/1981 | Lapeyre |
| 4,278,249 A | 7/1981 | Forrest |
| 4,286,782 A | 9/1981 | Fuhrhop |
| 4,290,601 A | 9/1981 | Mittelstadt |
| 4,300,761 A | 11/1981 | Howard |
| 4,313,602 A | 2/1982 | Sullivan |
| 4,313,603 A | 2/1982 | Simjian |
| 4,324,501 A | 4/1982 | Herbenar |
| 4,333,978 A | 6/1982 | Kocher |
| 4,334,676 A | 6/1982 | Schonenberger |
| 4,334,695 A | 6/1982 | Ashby |
| 4,337,283 A | 6/1982 | Haas, Jr. |
| 4,342,452 A | 8/1982 | Summa |
| 4,344,616 A | 8/1982 | Ogden |
| 4,349,597 A | 9/1982 | Fine et al. |
| 4,350,336 A | 9/1982 | Hanford |
| 4,358,105 A | 11/1982 | Sweeney, Jr. |
| 4,363,480 A | 12/1982 | Fisher et al. |
| 4,363,486 A | 12/1982 | Chaudhry |
| 4,367,895 A | 1/1983 | Pacitti et al. |
| 4,369,081 A | 1/1983 | Curry et al. |
| 4,370,766 A | 2/1983 | Teague, Jr. |
| 4,374,587 A | 2/1983 | Ogden |
| 4,377,045 A | 3/1983 | Moulinex |
| 4,383,684 A | 5/1983 | Schliep |
| 4,383,714 A | 5/1983 | Ishida |
| 4,397,462 A | 8/1983 | Wilmarth |
| 4,406,451 A | 9/1983 | Gaetano |
| 4,408,613 A | 10/1983 | Relyea |
| 4,422,635 A | 12/1983 | Herod |
| 4,422,636 A | 12/1983 | de Angeli |
| 4,423,864 A | 1/1984 | Wiik |
| 4,426,077 A | 1/1984 | Becker |
| 4,431,181 A | 2/1984 | Baswell |
| 4,434,981 A | 3/1984 | Norton |
| 4,441,708 A | 4/1984 | Brentham |
| 4,445,684 A | 5/1984 | Ruff |
| 4,452,448 A | 6/1984 | Ausherman |
| 4,453,766 A | 6/1984 | DiVito |
| 4,461,472 A | 7/1984 | Martinez |
| 4,465,277 A | 8/1984 | Dittrich |
| 4,476,582 A | 10/1984 | Strauss et al. |
| 4,477,071 A | 10/1984 | Brown et al. |
| 4,489,933 A | 12/1984 | Fisher |
| 4,491,318 A | 1/1985 | Francke |
| 4,494,662 A | 1/1985 | Clymer |
| 4,496,147 A | 1/1985 | DeCloux et al. |
| 4,499,784 A | 2/1985 | Shum |
| 4,502,679 A | 3/1985 | De Lorenzo |
| 4,505,474 A | 3/1985 | Mattox |
| 4,505,475 A | 3/1985 | Olschansky et al. |
| 4,509,510 A | 4/1985 | Hook |
| 4,512,567 A | 4/1985 | Phillips |
| 4,512,571 A | 4/1985 | Hermelin |
| 4,522,394 A | 6/1985 | Broussard |
| 4,529,194 A | 7/1985 | Haaheim |
| 4,533,136 A | 8/1985 | Smith et al. |
| 4,536,244 A | 8/1985 | Greci et al. |
| 4,538,805 A | 9/1985 | Parviainen |
| 4,542,899 A | 9/1985 | Hendricks |
| 4,544,152 A | 10/1985 | Taitel |
| 4,544,153 A | 10/1985 | Babcock |
| 4,546,971 A | 10/1985 | Raasoch |
| 4,548,405 A | 10/1985 | Lee |
| 4,549,733 A | 10/1985 | Salyer |
| 4,556,216 A | 12/1985 | Pitkanen |
| 4,563,001 A | 1/1986 | Terauds |
| 4,563,003 A | 1/1986 | Bugallo et al. |
| 4,564,193 A | 1/1986 | Stewart |
| 4,566,689 A | 1/1986 | Ogden |
| 4,566,732 A | 1/1986 | Ostergaard, Sr. |
| 4,569,518 A | 2/1986 | Fulks |
| 4,571,682 A | 2/1986 | Silverman et al. |
| 4,572,500 A | 2/1986 | Weiss |
| 4,572,504 A | 2/1986 | DiBartolo |
| 4,576,352 A | 3/1986 | Ogden |
| 4,576,376 A | 3/1986 | Miller |
| 4,577,860 A | 3/1986 | Matias et al. |
| 4,580,983 A | 4/1986 | Cassini et al. |
| 4,581,269 A | 4/1986 | Tilman |
| 4,582,320 A | 4/1986 | Shaw |
| 4,589,656 A | 5/1986 | Baldwin |
| 4,591,147 A | 5/1986 | Smith et al. |
| 4,592,544 A | 6/1986 | Smith et al. |
| 4,600,196 A | 7/1986 | Jones |
| 4,601,142 A | 7/1986 | Frommelt |
| 4,602,779 A | 7/1986 | Ogden |
| 4,610,449 A | 9/1986 | Diercks, Jr. |
| 4,614,337 A | 9/1986 | Schonenberger |
| 4,616,822 A | 10/1986 | Trulaske |
| 4,618,139 A | 10/1986 | Haaheim |
| 4,618,140 A | 10/1986 | Brown |
| 4,619,454 A | 10/1986 | Walton |
| 4,621,623 A | 11/1986 | Wang |
| 4,624,457 A | 11/1986 | Silberman et al. |
| 4,625,962 A | 12/1986 | Street |
| 4,627,614 A | 12/1986 | De Angeli |
| 4,627,615 A | 12/1986 | Nurkowski |
| 4,627,616 A | 12/1986 | Kauffman |
| 4,630,817 A | 12/1986 | Buckley |
| 4,632,385 A | 12/1986 | Geraci |
| 4,632,386 A | 12/1986 | Beech |
| 4,632,390 A | 12/1986 | Richey |
| 4,634,127 A | 1/1987 | Rockwell |
| 4,635,927 A | 1/1987 | Shu |
| 4,635,928 A | 1/1987 | Ogden et al. |
| 4,637,605 A | 1/1987 | Ritchie |
| 4,638,523 A | 1/1987 | Todd |
| 4,638,969 A | 1/1987 | Brown |

(56) References Cited

U.S. PATENT DOCUMENTS

| | | | |
|---|---|---|---|
| 4,641,833 A | 2/1987 | Trethewey |
| 4,642,080 A | 2/1987 | Takano et al. |
| 4,643,418 A | 2/1987 | Bart |
| 4,645,197 A | 2/1987 | Mcfee |
| 4,645,200 A | 2/1987 | Hix |
| 4,645,201 A | 2/1987 | Evans |
| 4,645,917 A | 2/1987 | Penney et al. |
| 4,647,041 A | 3/1987 | Whiteley |
| 4,650,067 A | 3/1987 | Brule |
| 4,650,184 A | 3/1987 | Brebner |
| 4,650,185 A | 3/1987 | Cartwright |
| 4,651,581 A | 3/1987 | Svensson |
| 4,659,074 A | 4/1987 | Taitel et al. |
| 4,659,077 A | 4/1987 | Stropkay |
| 4,659,078 A | 4/1987 | Blome |
| 4,662,630 A | 5/1987 | Dignard et al. |
| 4,664,371 A | 5/1987 | Viander |
| 4,664,373 A | 5/1987 | Hait |
| 4,664,646 A | 5/1987 | Rorabaugh |
| 4,673,177 A | 6/1987 | Szymski |
| 4,674,740 A | 6/1987 | Iams et al. |
| 4,674,743 A | 6/1987 | Hirano |
| 4,678,185 A | 7/1987 | Mahnke |
| 4,679,787 A | 7/1987 | Guilbault |
| 4,684,121 A | 8/1987 | Nestegard |
| 4,685,670 A | 8/1987 | Zinkin |
| 4,687,195 A | 8/1987 | Potts |
| 4,697,809 A | 10/1987 | Rockwell |
| 4,700,946 A | 10/1987 | Breunig |
| 4,702,475 A | 10/1987 | Elstein et al. |
| 4,705,267 A | 11/1987 | Jackson |
| 4,708,337 A | 11/1987 | Shyu |
| 4,709,917 A | 12/1987 | Yang |
| 4,709,918 A | 12/1987 | Grinblat |
| 4,709,920 A | 12/1987 | Schnell |
| 4,711,447 A | 12/1987 | Mansfield |
| 4,714,248 A | 12/1987 | Koss |
| 4,718,207 A | 1/1988 | Frommelt |
| 4,720,093 A | 1/1988 | Del Mar |
| 4,720,099 A | 1/1988 | Carlson |
| 4,720,789 A | 1/1988 | Hector et al. |
| 4,721,303 A | 1/1988 | Fitzpatrick |
| 4,725,057 A | 2/1988 | Shifferaw |
| 4,726,581 A | 2/1988 | Chang |
| 4,729,558 A | 3/1988 | Kuo |
| 4,729,562 A | 3/1988 | Pipasik |
| 4,733,858 A | 3/1988 | Lan |
| 4,743,009 A | 5/1988 | Beale |
| 4,743,015 A | 5/1988 | Marshall |
| 4,744,559 A | 5/1988 | Mahnke et al. |
| 4,746,115 A | 5/1988 | Lahman |
| 4,749,184 A | 6/1988 | Tobin |
| 4,750,736 A | 6/1988 | Watterson |
| 4,751,755 A | 6/1988 | Carey, Jr. et al. |
| 4,756,098 A | 7/1988 | Boggia |
| 4,757,987 A | 7/1988 | Allemand |
| 4,759,540 A | 7/1988 | Yu et al. |
| 4,771,148 A | 9/1988 | Bersonnet |
| 4,772,015 A | 9/1988 | Carlson et al. |
| 4,773,170 A | 9/1988 | Moore et al. |
| 4,776,582 A | 10/1988 | Ramhorst |
| 4,779,884 A | 10/1988 | Minati |
| 4,786,049 A | 11/1988 | Lautenschlager |
| 4,786,050 A | 11/1988 | Geschwender |
| 4,790,528 A | 12/1988 | Nakao et al. |
| 4,792,134 A | 12/1988 | Chen |
| 4,797,968 A | 1/1989 | Wenzlick |
| 4,798,760 A | 1/1989 | Diaz-Kotti |
| 4,799,475 A | 1/1989 | Iams et al. |
| 4,799,671 A | 1/1989 | Hoggan et al. |
| 4,801,079 A | 1/1989 | Gonella |
| 4,804,178 A | 2/1989 | Friedebach |
| 4,805,901 A | 2/1989 | Kulick |
| 4,807,874 A | 2/1989 | Little |
| 4,809,804 A | 3/1989 | Houston et al. |
| 4,809,972 A | 3/1989 | Rasmussen et al. |
| 4,813,667 A | 3/1989 | Watterson |
| 4,813,668 A | 3/1989 | Solloway |
| 4,813,743 A | 3/1989 | Mizelle |
| 4,817,939 A | 4/1989 | Augspurger et al. |
| 4,818,175 A | 4/1989 | Kimura |
| 4,819,583 A | 4/1989 | Guerra |
| 4,822,029 A | 4/1989 | Sarno |
| 4,822,034 A | 4/1989 | Shields |
| 4,824,104 A | 4/1989 | Bloch |
| 4,826,153 A | 5/1989 | Schalip |
| 4,826,157 A | 5/1989 | Fitzpatrick |
| 4,826,158 A | 5/1989 | Fields, Jr. |
| 4,826,159 A | 5/1989 | Hersey |
| 4,826,255 A | 5/1989 | Lahman |
| 4,828,257 A | 5/1989 | Dyer et al. |
| 4,830,362 A | 5/1989 | Bull |
| 4,832,332 A | 5/1989 | Dumbser |
| 4,836,530 A | 6/1989 | Stanley, Jr. |
| 4,838,543 A | 6/1989 | Armstrong et al. |
| 4,838,544 A | 6/1989 | Sasakawa et al. |
| 4,842,266 A | 6/1989 | Sweeney, Sr. |
| 4,842,274 A | 6/1989 | Oosthuizen |
| 4,844,449 A | 7/1989 | Truslaske |
| 4,844,450 A | 7/1989 | Rodgers, Jr. |
| 4,848,737 A | 7/1989 | Ehrenfield |
| 4,850,585 A | 7/1989 | Dalebout |
| 4,861,023 A | 8/1989 | Wedman |
| 4,861,025 A | 8/1989 | Rockwell |
| 4,863,161 A | 9/1989 | Telle |
| 4,865,344 A | 9/1989 | Romero, Sr. et al. |
| 4,867,443 A | 9/1989 | Jensen |
| 4,869,493 A | 9/1989 | Johnston |
| 4,869,494 A | 9/1989 | Lambert, Sr. |
| 4,869,497 A | 9/1989 | Stewart et al. |
| 4,875,676 A | 10/1989 | Zimmer |
| 4,877,239 A | 10/1989 | Dela Rosa |
| 4,878,662 A | 11/1989 | Chern |
| 4,878,663 A | 11/1989 | Luquette |
| 4,880,227 A | 11/1989 | Sowell |
| 4,883,272 A | 11/1989 | Lay |
| 4,886,266 A | 12/1989 | Trulaske |
| 4,891,764 A | 1/1990 | McIntosh |
| 4,894,933 A | 1/1990 | Tonkel et al. |
| 4,898,379 A | 2/1990 | Shiba |
| 4,898,381 A | 2/1990 | Gordon |
| 4,900,012 A | 2/1990 | Fu |
| 4,900,017 A | 2/1990 | Bold, Jr. |
| 4,900,018 A | 2/1990 | Ish, III |
| 4,902,006 A | 2/1990 | Stallings, Jr. |
| 4,904,829 A | 2/1990 | Berthaud et al. |
| 4,905,330 A | 3/1990 | Jacobs |
| 4,907,795 A | 3/1990 | Shaw et al. |
| 4,907,797 A | 3/1990 | Gezari et al. |
| 4,907,798 A | 3/1990 | Burchatz |
| 4,909,504 A | 3/1990 | Yang |
| 4,911,438 A | 3/1990 | Van Straaten |
| 4,913,396 A | 4/1990 | Dalebout et al. |
| 4,913,423 A | 4/1990 | Farran |
| 4,915,377 A | 4/1990 | Malnke et al. |
| 4,915,379 A | 4/1990 | Sapp |
| 4,917,376 A | 4/1990 | Lo |
| 4,919,418 A | 4/1990 | Miller |
| 4,919,419 A | 4/1990 | Houston |
| 4,921,242 A | 5/1990 | Watterson |
| 4,921,247 A | 5/1990 | Sterling |
| 4,923,193 A | 5/1990 | Pitzen et al. |
| 4,925,183 A | 5/1990 | Kim |
| 4,925,724 A | 5/1990 | Ogden |
| 4,927,136 A | 5/1990 | Leask |
| 4,928,546 A | 5/1990 | Walters |
| 4,928,957 A | 5/1990 | Lanier et al. |
| 4,930,768 A | 6/1990 | Lapcevic |
| 4,930,769 A | 6/1990 | Nenoff |
| 4,934,690 A | 6/1990 | Bull |
| 4,934,692 A | 6/1990 | Owens |
| 4,938,473 A | 7/1990 | Lee |
| 4,940,233 A | 7/1990 | Bull |
| 4,941,652 A | 7/1990 | Nagano et al. |

(56) References Cited

U.S. PATENT DOCUMENTS

| | | |
|---|---|---|
| 4,941,673 A | 7/1990 | Bennett |
| 4,948,121 A | 8/1990 | Haaheim et al. |
| 4,949,954 A | 8/1990 | Hix |
| 4,949,958 A | 8/1990 | Richey |
| 4,949,959 A | 8/1990 | Stevens |
| 4,952,265 A | 8/1990 | Yamanaka et al. |
| 4,953,415 A | 9/1990 | Oy |
| 4,953,858 A | 9/1990 | Zelli |
| 4,955,466 A | 9/1990 | Almes et al. |
| 4,958,832 A | 9/1990 | Kim |
| 4,960,276 A | 10/1990 | Feuer et al. |
| 4,964,632 A | 10/1990 | Rockwell |
| 4,968,028 A | 11/1990 | Wehrell |
| 4,971,316 A | 11/1990 | Dalebout et al. |
| 4,974,831 A | 12/1990 | Dunham |
| 4,974,832 A | 12/1990 | Dalebout |
| 4,976,424 A | 12/1990 | Sargeant et al. |
| 4,976,428 A | 12/1990 | Ghazi |
| 4,976,435 A | 12/1990 | Shatford |
| 4,984,810 A | 1/1991 | Stearns |
| 4,989,860 A | 2/1991 | Iams et al. |
| 4,998,725 A | 3/1991 | Watterson et al. |
| 5,000,440 A | 3/1991 | Lynch |
| 5,000,442 A | 3/1991 | Dalebout et al. |
| 5,001,632 A | 3/1991 | Hall |
| 5,002,271 A | 3/1991 | Gonzales |
| 5,004,224 A | 4/1991 | Wang |
| 5,007,630 A | 4/1991 | Real et al. |
| 5,007,631 A | 4/1991 | Wang |
| 5,013,031 A | 5/1991 | Bull |
| 5,016,870 A | 5/1991 | Bulloch et al. |
| 5,020,793 A | 6/1991 | Loane |
| 5,024,441 A | 6/1991 | Rousseau |
| 5,026,049 A | 6/1991 | Goodman |
| 5,027,303 A | 6/1991 | Witte |
| 5,029,801 A | 7/1991 | Dalebout et al. |
| 5,031,455 A | 7/1991 | Cline |
| 5,031,901 A | 7/1991 | Oy |
| 5,034,576 A | 7/1991 | Dalebout et al. |
| RE33,662 E | 8/1991 | Blair et al. |
| 5,037,084 A | 8/1991 | Flor |
| 5,037,089 A | 8/1991 | Spagnuolo |
| 5,039,089 A | 8/1991 | Lapcevic |
| 5,039,091 A | 8/1991 | Johnson |
| 5,042,799 A | 8/1991 | Stanley |
| 5,046,382 A | 9/1991 | Steinberg |
| 5,046,722 A | 9/1991 | Antoon |
| 5,048,823 A | 9/1991 | Bean |
| 5,051,638 A | 9/1991 | Pyles |
| 5,054,770 A | 10/1991 | Bull |
| 5,058,881 A | 10/1991 | Measom |
| 5,058,882 A | 10/1991 | Dalebout et al. |
| 5,058,888 A | 10/1991 | Walker et al. |
| 5,062,626 A | 11/1991 | Dalebout et al. |
| 5,062,629 A | 11/1991 | Vaughan |
| 5,062,632 A | 11/1991 | Dalebout et al. |
| 5,066,000 A | 11/1991 | Dolan |
| 5,067,710 A | 11/1991 | Watterson et al. |
| 5,071,115 A | 12/1991 | Welch |
| 5,072,928 A | 12/1991 | Stearns et al. |
| 5,072,929 A | 12/1991 | Peterson et al. |
| 5,074,550 A | 12/1991 | Sloan |
| 5,077,916 A | 1/1992 | Beneteau |
| 5,080,353 A | 1/1992 | Tench |
| 5,081,991 A | 1/1992 | Chance |
| 5,085,426 A | 2/1992 | Wanzer et al. |
| 5,085,427 A | 2/1992 | Finn |
| 5,087,047 A | 2/1992 | McConnell |
| 5,088,729 A | 2/1992 | Dalebout |
| 5,094,249 A | 3/1992 | Marras et al. |
| 5,094,447 A | 3/1992 | Wang |
| 5,096,225 A | 3/1992 | Osawa |
| 5,102,122 A | 4/1992 | Piane, Jr. |
| 5,102,380 A | 4/1992 | Jacobson et al. |
| 5,104,119 A | 4/1992 | Lynch |
| 5,104,120 A | 4/1992 | Watterson et al. |
| 5,108,093 A | 4/1992 | Watterson |
| 5,109,778 A | 5/1992 | Berkowitz et al. |
| 5,110,117 A | 5/1992 | Fisher et al. |
| 5,112,045 A | 5/1992 | Mason et al. |
| 5,114,388 A | 5/1992 | Trulaske |
| 5,114,391 A | 5/1992 | Pitzen et al. |
| 5,123,629 A | 6/1992 | Takeuchi |
| 5,123,885 A | 6/1992 | Shields |
| 5,123,886 A | 6/1992 | Cook |
| 5,129,872 A | 7/1992 | Dalton et al. |
| 5,131,895 A | 7/1992 | Rogers, Jr. |
| 5,135,458 A | 8/1992 | Huang |
| 5,137,501 A | 8/1992 | Mertesdorf |
| 5,138,730 A | 8/1992 | Masuda |
| 5,141,480 A | 8/1992 | Lennox et al. |
| 5,142,358 A | 8/1992 | Jason |
| 5,145,475 A | 9/1992 | Cares |
| 5,145,481 A | 9/1992 | Friedebach |
| 5,147,266 A | 9/1992 | Ricard |
| 5,149,084 A | 9/1992 | Dalebout et al. |
| 5,149,312 A | 9/1992 | Croft et al. |
| 5,158,520 A | 10/1992 | Lemke et al. |
| 5,162,029 A | 11/1992 | Schine |
| 5,163,885 A | 11/1992 | Wanzer et al. |
| 5,167,159 A | 12/1992 | Lucking |
| 5,167,597 A | 12/1992 | David |
| 5,171,196 A | 12/1992 | Lynch |
| 5,178,593 A | 1/1993 | Roberts |
| 5,178,599 A | 1/1993 | Scott |
| 5,181,894 A | 1/1993 | Shieng |
| 5,184,295 A | 2/1993 | Mann |
| 5,184,988 A | 2/1993 | Dunham |
| 5,186,697 A | 2/1993 | Rennex |
| 5,192,255 A | 3/1993 | Dalebout et al. |
| 5,192,257 A | 3/1993 | Panasewicz |
| 5,192,258 A | 3/1993 | Keller |
| 5,195,781 A | 3/1993 | Osawa |
| 5,195,935 A | 3/1993 | Fencel |
| 5,195,937 A | 3/1993 | Engel et al. |
| 5,199,931 A | 4/1993 | Easley et al. |
| 5,201,694 A | 4/1993 | Zappel |
| 5,203,229 A | 4/1993 | Chen |
| 5,203,800 A | 4/1993 | Meredith |
| 5,203,826 A | 4/1993 | Dalebout |
| 5,205,798 A | 4/1993 | Lekhtman |
| 5,205,800 A | 4/1993 | Grant |
| 5,207,489 A | 5/1993 | Miller |
| 5,207,622 A | 5/1993 | Wilkinson et al. |
| 5,207,625 A | 5/1993 | White |
| 5,207,628 A | 5/1993 | Graham |
| 5,211,617 A | 5/1993 | Millen |
| 5,215,510 A | 6/1993 | Baran |
| 5,217,422 A | 6/1993 | Domzalski |
| 5,226,866 A | 7/1993 | Engel et al. |
| 5,232,422 A | 8/1993 | Bishop, Jr. |
| 5,234,392 A | 8/1993 | Clark |
| 5,240,417 A | 8/1993 | Smithson et al. |
| 5,242,339 A | 9/1993 | Thornton |
| 5,242,340 A | 9/1993 | Jerome |
| 5,242,343 A | 9/1993 | Miller |
| 5,242,347 A | 9/1993 | Keeton |
| 5,247,853 A | 9/1993 | Dalebout |
| 5,250,012 A | 10/1993 | Whitcomb, Jr. |
| 5,250,013 A | 10/1993 | Brangi |
| 5,254,067 A | 10/1993 | Habing et al. |
| 5,256,117 A | 10/1993 | Potts et al. |
| 5,256,118 A | 10/1993 | Chen |
| 5,256,126 A | 10/1993 | Grotstein |
| 5,257,701 A | 11/1993 | Edelson |
| 5,257,964 A | 11/1993 | Petters |
| 5,261,864 A | 11/1993 | Fitzpatrick |
| 5,269,736 A | 12/1993 | Roberts |
| 5,271,416 A | 12/1993 | Lepley |
| 5,273,285 A | 12/1993 | Long |
| 5,277,678 A | 1/1994 | Friedebach et al. |
| 5,279,528 A | 1/1994 | Dalebout et al. |
| 5,279,529 A | 1/1994 | Eschenbach |
| 5,279,531 A | 1/1994 | Jen Huey |

(56) References Cited

U.S. PATENT DOCUMENTS

| | | |
|---|---|---|
| 5,282,776 A | 2/1994 | Dalebout |
| 5,284,461 A | 2/1994 | Wilkinson et al. |
| 5,290,205 A | 3/1994 | Densmore et al. |
| 5,290,211 A | 3/1994 | Stearns |
| 5,292,293 A | 3/1994 | Schumacher |
| 5,295,928 A | 3/1994 | Rennex |
| 5,295,935 A | 3/1994 | Wang |
| 5,299,992 A | 4/1994 | Wilkinson |
| 5,299,993 A | 4/1994 | Habing |
| 5,302,162 A | 4/1994 | Pasero |
| 5,306,221 A | 4/1994 | Itaru |
| 5,308,075 A | 5/1994 | Theriault |
| 5,308,304 A | 5/1994 | Habing |
| 5,310,392 A | 5/1994 | Lo |
| 5,313,852 A | 5/1994 | Arena |
| 5,314,390 A | 5/1994 | Westing et al. |
| 5,314,391 A | 5/1994 | Potash et al. |
| 5,314,392 A | 5/1994 | Hawkins et al. |
| 5,314,394 A | 5/1994 | Ronan |
| 5,318,487 A | 6/1994 | Golen et al. |
| 5,320,343 A | 6/1994 | McKinney |
| 5,320,588 A | 6/1994 | Wanzer et al. |
| 5,320,591 A | 6/1994 | Harmon et al. |
| 5,324,242 A | 6/1994 | Lo |
| 5,328,420 A | 7/1994 | Allen |
| 5,328,422 A | 7/1994 | Nichols |
| 5,328,429 A | 7/1994 | Potash et al. |
| 5,330,401 A | 7/1994 | Walstead |
| 5,330,402 A | 7/1994 | Johnson |
| 5,334,120 A | 8/1994 | Rasmussen |
| 5,336,144 A | 8/1994 | Rodden |
| 5,336,145 A | 8/1994 | Keiser |
| 5,336,146 A | 8/1994 | Piaget et al. |
| 5,342,264 A | 8/1994 | Gordon |
| 5,342,271 A | 8/1994 | Long |
| RE34,728 E | 9/1994 | Hall-Tipping |
| 5,344,372 A | 9/1994 | Hung |
| 5,348,524 A | 9/1994 | Grant |
| 5,350,344 A | 9/1994 | Kissel |
| 5,352,166 A | 10/1994 | Chang |
| 5,352,167 A | 10/1994 | Ulicny |
| 5,352,169 A | 10/1994 | Eschenbach |
| 5,353,452 A | 10/1994 | Rulis |
| 5,354,248 A | 10/1994 | Rawls et al. |
| 5,354,251 A | 10/1994 | Sleamaker |
| 5,356,356 A | 10/1994 | Hildebrandt et al. |
| 5,358,461 A | 10/1994 | Bailey, Jr. |
| 5,359,986 A | 11/1994 | Magrath, III et al. |
| 5,362,069 A | 11/1994 | Hall-Tipping |
| 5,362,295 A | 11/1994 | Nurge |
| 5,364,327 A | 11/1994 | Graham |
| 5,368,532 A | 11/1994 | Farnet |
| 5,372,556 A | 12/1994 | Ropp |
| 5,372,559 A | 12/1994 | Dalebout et al. |
| 5,372,560 A | 12/1994 | Chang |
| 5,372,564 A | 12/1994 | Spirito |
| 5,374,227 A | 12/1994 | Webb |
| 5,378,212 A | 1/1995 | Pin-Kuo |
| 5,380,258 A | 1/1995 | Hawley, Jr. |
| 5,382,207 A | 1/1995 | Skowronski et al. |
| 5,382,208 A | 1/1995 | Hu |
| 5,382,209 A | 1/1995 | Pasier |
| 5,383,827 A | 1/1995 | Stern |
| 5,383,828 A | 1/1995 | Sands et al. |
| 5,385,346 A | 1/1995 | Carroll et al. |
| 5,385,519 A | 1/1995 | Hsu |
| 5,387,169 A | 2/1995 | Wang |
| 5,387,170 A | 2/1995 | Rawls et al. |
| 5,387,171 A | 2/1995 | Casey et al. |
| 5,394,922 A | 3/1995 | Colson et al. |
| 5,396,876 A | 3/1995 | Liscio et al. |
| 5,398,948 A | 3/1995 | Mathis |
| 5,401,226 A | 3/1995 | Stearns |
| 5,403,251 A | 4/1995 | Belsito et al. |
| 5,403,252 A | 4/1995 | Leon et al. |
| 5,403,253 A | 4/1995 | Gaylord |
| 5,403,254 A | 4/1995 | Lundin et al. |
| 5,403,255 A | 4/1995 | Johnston |
| 5,406,661 A | 4/1995 | Pekar |
| 5,407,403 A | 4/1995 | Coleman |
| 5,407,408 A | 4/1995 | Wilkinson |
| 5,409,435 A | 4/1995 | Daniels |
| RE34,959 E | 5/1995 | Potts |
| 5,410,971 A | 5/1995 | Golden et al. |
| 5,417,643 A | 5/1995 | Taylor |
| 5,419,570 A | 5/1995 | Bollotte |
| 5,419,571 A | 5/1995 | Vaughan |
| 5,419,751 A | 5/1995 | Byrd et al. |
| 5,423,729 A | 6/1995 | Eschenbach |
| 5,423,730 A | 6/1995 | Hirsch |
| 5,429,563 A | 7/1995 | Engel et al. |
| 5,429,569 A | 7/1995 | Gunnari |
| 5,431,612 A | 7/1995 | Holden |
| 5,433,679 A | 7/1995 | Szymczak et al. |
| 5,435,315 A | 7/1995 | McPhee et al. |
| 5,435,798 A | 7/1995 | Habing et al. |
| 5,441,467 A | 8/1995 | Stevens |
| 5,441,468 A | 8/1995 | Deckers et al. |
| 5,449,334 A | 9/1995 | Kingsbury |
| 5,454,772 A | 10/1995 | Rodden |
| 5,454,773 A | 10/1995 | Blanchard et al. |
| 5,456,648 A | 10/1995 | Edinburg |
| 5,460,586 A | 10/1995 | Wilkinson |
| 5,462,503 A | 10/1995 | Benjamin et al. |
| 5,462,504 A | 10/1995 | Trulaske et al. |
| 5,466,200 A | 11/1995 | Ulrich et al. |
| 5,466,203 A | 11/1995 | Chen |
| 5,470,298 A | 11/1995 | Curtis |
| 5,471,405 A | 11/1995 | Marsh |
| 5,474,087 A | 12/1995 | Nashner |
| 5,474,510 A | 12/1995 | Chen |
| 5,476,430 A | 12/1995 | Lee et al. |
| 5,484,358 A | 1/1996 | Wang et al. |
| 5,484,362 A | 1/1996 | Skowronski et al. |
| 5,487,707 A | 1/1996 | Sharf et al. |
| 5,489,249 A | 2/1996 | Brewer et al. |
| 5,489,250 A | 2/1996 | Densmore et al. |
| 5,490,818 A | 2/1996 | Haber et al. |
| 5,492,514 A | 2/1996 | Daum |
| 5,492,520 A | 2/1996 | Brown |
| 5,496,235 A | 3/1996 | Stevens |
| 5,496,236 A | 3/1996 | Buonauito |
| 5,496,238 A | 3/1996 | Taylor |
| 5,496,239 A | 3/1996 | Kallman |
| 5,499,956 A | 3/1996 | Habing et al. |
| 5,505,011 A | 4/1996 | Bleimhofer |
| 5,507,271 A | 4/1996 | Actor |
| 5,509,870 A | 4/1996 | Lloyd |
| 5,512,025 A | 4/1996 | Dalebout et al. |
| 5,512,029 A | 4/1996 | Barnard |
| 5,514,053 A | 5/1996 | Hawkins et al. |
| 5,518,471 A | 5/1996 | Hettinger et al. |
| 5,518,473 A | 5/1996 | Miller |
| 5,520,599 A | 5/1996 | Chen |
| 5,522,783 A | 6/1996 | Gordon |
| 5,527,245 A | 6/1996 | Dalebout et al. |
| 5,529,554 A | 6/1996 | Eschenbach |
| 5,531,658 A | 7/1996 | L. S. C. |
| 5,533,899 A | 7/1996 | Young |
| 5,533,948 A | 7/1996 | Wilkinson |
| 5,533,951 A | 7/1996 | Chang |
| 5,538,489 A | 7/1996 | Magid |
| 5,542,892 A | 8/1996 | Buhler |
| 5,545,112 A | 8/1996 | Densmore et al. |
| 5,549,052 A | 8/1996 | Hoffman |
| 5,549,536 A | 8/1996 | Clark |
| 5,551,934 A | 9/1996 | Binette |
| 5,551,937 A | 9/1996 | Kwo |
| 5,554,033 A | 9/1996 | Bizzi et al. |
| 5,554,083 A | 9/1996 | Chen |
| 5,556,362 A | 9/1996 | Whipps |
| 5,562,572 A | 10/1996 | Carmein |
| 5,562,574 A | 10/1996 | Miller |
| 5,563,487 A | 10/1996 | Davis |

(56) References Cited

U.S. PATENT DOCUMENTS

| | | |
|---|---|---|
| 5,568,993 A | 10/1996 | Potzick |
| 5,569,128 A | 10/1996 | Dalebout |
| 5,569,138 A | 10/1996 | Wang et al. |
| 5,573,485 A | 11/1996 | Geschwender |
| 5,575,740 A | 11/1996 | Piaget |
| 5,577,985 A | 11/1996 | Miller |
| 5,577,987 A | 11/1996 | Brown |
| 5,580,249 A | 12/1996 | Jacobsen et al. |
| 5,582,563 A | 12/1996 | Fan |
| 5,584,700 A | 12/1996 | Feldman et al. |
| 5,584,779 A | 12/1996 | Knecht |
| 5,585,561 A | 12/1996 | Bahl et al. |
| 5,586,736 A | 12/1996 | Mollet |
| 5,588,938 A | 12/1996 | Schneider et al. |
| 5,590,893 A | 1/1997 | Robinson et al. |
| 5,591,104 A | 1/1997 | Andrus et al. |
| 5,591,106 A | 1/1997 | Dalebout et al. |
| 5,591,107 A | 1/1997 | Rodgers, Jr. |
| 5,591,908 A | 1/1997 | Reid |
| 5,593,372 A | 1/1997 | Rodgers, Jr. |
| 5,593,380 A | 1/1997 | Bittikofer |
| 5,595,556 A | 1/1997 | Dalebout et al. |
| 5,599,261 A | 2/1997 | Easley et al. |
| 5,600,310 A | 2/1997 | Whipple, III et al. |
| 5,603,675 A | 2/1997 | Wu |
| 5,603,678 A | 2/1997 | Wilson |
| 5,607,375 A | 3/1997 | Dalebout |
| 5,613,216 A | 3/1997 | Galler |
| 5,613,856 A | 3/1997 | Hoover |
| 5,616,103 A | 4/1997 | Lee |
| 5,622,527 A | 4/1997 | Watterson et al. |
| 5,625,577 A | 4/1997 | Kunii et al. |
| 5,626,539 A | 5/1997 | Piaget |
| 5,630,566 A | 5/1997 | Case |
| 5,632,209 A | 5/1997 | Sakakibara |
| 5,634,870 A | 6/1997 | Wilkinson |
| 5,643,142 A | 7/1997 | Salerno et al. |
| 5,643,144 A | 7/1997 | Trulaske |
| 5,643,147 A | 7/1997 | Huang |
| 5,643,152 A | 7/1997 | Simonson |
| 5,643,153 A | 7/1997 | Nylen et al. |
| 5,643,157 A | 7/1997 | Seliber |
| 5,645,509 A | 7/1997 | Brewer et al. |
| 5,645,914 A | 7/1997 | Horowitz |
| 5,649,882 A | 7/1997 | Parikh et al. |
| 5,650,709 A | 7/1997 | Rotunda et al. |
| 5,653,662 A | 8/1997 | Rodgers, Jr. |
| 5,655,997 A | 8/1997 | Greenberg et al. |
| 5,656,003 A | 8/1997 | Robinson et al. |
| 5,658,227 A | 8/1997 | Stearns |
| 5,662,557 A | 9/1997 | Watterson et al. |
| 5,665,031 A | 9/1997 | Hsieh |
| 5,665,033 A | 9/1997 | Palmer |
| 5,667,459 A | 9/1997 | Su |
| 5,669,833 A | 9/1997 | Stone |
| 5,669,857 A | 9/1997 | Watterson et al. |
| 5,669,865 A | 9/1997 | Gordon |
| 5,672,140 A | 9/1997 | Watterson et al. |
| 5,674,156 A | 10/1997 | Watterson et al. |
| 5,674,453 A | 10/1997 | Watterson et al. |
| 5,676,624 A | 10/1997 | Watterson et al. |
| 5,679,047 A | 10/1997 | Engel |
| 5,679,101 A | 10/1997 | Magid |
| 5,683,332 A | 11/1997 | Watterson et al. |
| 5,685,804 A | 11/1997 | Whan-Tong et al. |
| 5,688,209 A | 11/1997 | Trulaske et al. |
| 5,688,216 A | 11/1997 | Mauriello |
| 5,690,582 A | 11/1997 | Ulrich et al. |
| 5,690,587 A | 11/1997 | Gruenangerl |
| 5,690,589 A | 11/1997 | Rodgers, Jr. |
| 5,692,994 A | 12/1997 | Eschenbach |
| 5,695,436 A | 12/1997 | Huang |
| 5,702,325 A | 12/1997 | Watterson et al. |
| 5,704,879 A | 1/1998 | Watterson et al. |
| 5,707,319 A | 1/1998 | Riley |
| 5,708,355 A | 1/1998 | Schrey |
| 5,709,632 A | 1/1998 | Socwell |
| 5,709,633 A | 1/1998 | Sokol |
| 5,711,745 A | 1/1998 | Yang |
| 5,711,749 A | 1/1998 | Miller |
| 5,713,549 A | 2/1998 | Shieh |
| 5,713,821 A | 2/1998 | Nissen |
| 5,716,308 A | 2/1998 | Lee |
| 5,718,657 A | 2/1998 | Dalebout et al. |
| 5,718,660 A | 2/1998 | Chen |
| 5,720,200 A | 2/1998 | Anderson et al. |
| 5,720,474 A | 2/1998 | Sugiyama |
| 5,722,917 A | 3/1998 | Olschansky et al. |
| 5,722,920 A | 3/1998 | Bauer |
| 5,722,922 A | 3/1998 | Watterson et al. |
| 5,725,459 A | 3/1998 | Rexach |
| 5,730,236 A | 3/1998 | Miller et al. |
| 5,733,228 A | 3/1998 | Stevens |
| 5,733,229 A | 3/1998 | Dalebout et al. |
| 5,735,586 A | 4/1998 | Cheng |
| 5,735,773 A | 4/1998 | Vittone |
| 5,735,776 A | 4/1998 | Swezey |
| 5,738,612 A | 4/1998 | Tsuda |
| 5,741,205 A | 4/1998 | Doll et al. |
| 5,743,193 A | 4/1998 | Kakuta et al. |
| 5,743,832 A | 4/1998 | Sands et al. |
| 5,743,833 A | 4/1998 | Watterson et al. |
| 5,743,835 A | 4/1998 | Trotter |
| 5,746,682 A | 5/1998 | Hung |
| 5,749,372 A | 5/1998 | Allen |
| 5,749,787 A | 5/1998 | Jank |
| 5,749,807 A | 5/1998 | Webb |
| 5,749,809 A | 5/1998 | Lin |
| 5,749,813 A | 5/1998 | Domzalski |
| 5,752,879 A | 5/1998 | Berdut |
| 5,752,897 A | 5/1998 | Skowronski et al. |
| 5,755,642 A | 5/1998 | Miller |
| 5,755,645 A | 5/1998 | Miller et al. |
| 5,755,651 A | 5/1998 | Homyonfer |
| 5,759,136 A | 6/1998 | Chen |
| 5,760,353 A | 6/1998 | Rapp |
| 5,761,831 A | 6/1998 | Cho |
| 5,762,587 A | 6/1998 | Dalebout et al. |
| 5,762,588 A | 6/1998 | Chen |
| 5,769,759 A | 6/1998 | Alter |
| 5,771,152 A | 6/1998 | Crompton et al. |
| 5,772,522 A | 6/1998 | Nesbit |
| 5,772,558 A | 6/1998 | Rodgers, Jr. |
| 5,772,560 A | 6/1998 | Watterson et al. |
| 5,776,582 A | 7/1998 | Needham |
| 5,779,599 A | 7/1998 | Chen |
| 5,779,607 A | 7/1998 | Harris |
| 5,782,639 A | 7/1998 | Beal |
| 5,782,723 A | 7/1998 | Kuo |
| 5,785,630 A | 7/1998 | Bobick et al. |
| 5,788,609 A | 8/1998 | Miller |
| 5,788,610 A | 8/1998 | Eschenbach |
| 5,788,611 A | 8/1998 | Kuo |
| 5,792,027 A | 8/1998 | Gvoich |
| 5,792,031 A | 8/1998 | Alton |
| 5,795,270 A | 8/1998 | Woods et al. |
| 5,797,578 A | 8/1998 | Graffeo |
| 5,803,874 A | 9/1998 | Wilkinson |
| 5,803,877 A | 9/1998 | Franey |
| 5,803,882 A | 9/1998 | Habing et al. |
| 5,807,210 A | 9/1998 | Devlin |
| 5,810,696 A | 9/1998 | Webb |
| 5,810,697 A | 9/1998 | Joiner |
| 5,810,698 A | 9/1998 | Hullett et al. |
| 5,813,142 A | 9/1998 | Demon |
| 5,813,947 A | 9/1998 | Densmore |
| 5,813,953 A | 9/1998 | Whipple |
| 5,816,981 A | 10/1998 | Hung |
| 5,820,478 A | 10/1998 | Wood et al. |
| 5,823,618 A | 10/1998 | Fox et al. |
| 5,827,155 A | 10/1998 | Jensen et al. |
| 5,827,158 A | 10/1998 | Drecksel |
| 5,830,113 A | 11/1998 | Coody et al. |
| 5,830,114 A | 11/1998 | Halfen et al. |

(56) References Cited

U.S. PATENT DOCUMENTS

| | | | |
|---|---|---|---|
| 5,833,577 A | 11/1998 | Hurt | |
| 5,833,583 A | 11/1998 | Chuang | |
| 5,833,584 A | 11/1998 | Piaget et al. | |
| 5,833,587 A | 11/1998 | Strong et al. | |
| 5,836,770 A | 11/1998 | Powers | |
| 5,839,990 A | 11/1998 | Virkkala | |
| 5,839,993 A | 11/1998 | Fox | |
| 5,842,961 A | 12/1998 | Davis | |
| 5,846,166 A | 12/1998 | Kuo | |
| 5,848,954 A | 12/1998 | Stearns et al. | |
| 5,852,264 A | 12/1998 | Muller | |
| 5,855,537 A | 1/1999 | Coody et al. | |
| 5,855,538 A | 1/1999 | Argabright | |
| 5,857,939 A | 1/1999 | Kaufman | |
| 5,857,940 A | 1/1999 | Husted | |
| 5,857,941 A | 1/1999 | Maresh | |
| 5,857,943 A | 1/1999 | Murray | |
| 5,860,893 A | 1/1999 | Watterson et al. | |
| 5,860,894 A | 1/1999 | Dalebout et al. | |
| 5,860,899 A | 1/1999 | Rassman | |
| 5,865,710 A | 2/1999 | Wilson-Hyde | |
| 5,868,108 A | 2/1999 | Schmitz et al. | |
| 5,868,648 A | 2/1999 | Coody et al. | |
| 5,871,421 A | 2/1999 | Trulaske et al. | |
| 5,876,095 A | 3/1999 | Johnston | |
| 5,879,271 A | 3/1999 | Stearns et al. | |
| 5,879,273 A | 3/1999 | Wei | |
| 5,879,276 A | 3/1999 | Miller | |
| 5,882,281 A | 3/1999 | Stearns et al. | |
| 5,885,197 A | 3/1999 | Barton | |
| 5,888,172 A | 3/1999 | Andrus et al. | |
| 5,890,562 A | 4/1999 | Bartels et al. | |
| 5,890,995 A | 4/1999 | Bobick et al. | |
| 5,891,001 A | 4/1999 | Carnes et al. | |
| 5,891,003 A | 4/1999 | Deac et al. | |
| 5,895,339 A | 4/1999 | Maresh | |
| 5,895,340 A | 4/1999 | Keller | |
| 5,897,457 A | 4/1999 | Mackovjak | |
| 5,897,459 A | 4/1999 | Habing et al. | |
| 5,897,460 A | 4/1999 | McBride et al. | |
| 5,897,461 A | 4/1999 | Socwell | |
| 5,899,833 A | 5/1999 | Ryan et al. | |
| 5,899,834 A | 5/1999 | Dalebout et al. | |
| 5,902,214 A | 5/1999 | Makikawa et al. | |
| 5,904,398 A | 5/1999 | Farricielli | |
| 5,904,636 A | 5/1999 | Chen | |
| 5,906,269 A | 5/1999 | Zabron et al. | |
| 5,906,564 A | 5/1999 | Jacobsen | |
| 5,910,070 A | 6/1999 | Henry et al. | |
| 5,910,072 A | 6/1999 | Rawls et al. | |
| 5,911,132 A | 6/1999 | Sloane | |
| 5,913,751 A | 6/1999 | Eschenbach | |
| 5,916,064 A | 6/1999 | Eschenbach | |
| 5,916,069 A | 6/1999 | Wang | |
| 5,917,692 A | 6/1999 | Schmitz et al. | |
| 5,919,118 A | 7/1999 | Stearns | |
| 5,921,892 A | 7/1999 | Easton | |
| 5,921,896 A | 7/1999 | Boland | |
| 5,925,001 A | 7/1999 | Hoyt et al. | |
| 5,938,551 A | 8/1999 | Warner | |
| 5,938,565 A | 8/1999 | Bernacki | |
| 5,938,570 A | 8/1999 | Maresh | |
| 5,938,571 A | 8/1999 | Stevens | |
| 5,938,575 A | 8/1999 | Stearns | |
| 5,940,502 A | 8/1999 | Hirai et al. | |
| 5,940,911 A | 8/1999 | Wang | |
| 5,941,807 A | 8/1999 | Cassidy | |
| 5,943,794 A | 8/1999 | Gelsomini | |
| 5,944,641 A | 8/1999 | Habing | |
| 5,947,869 A | 9/1999 | Shea | |
| 5,947,872 A | 9/1999 | Ryan et al. | |
| 5,951,444 A | 9/1999 | Webber | |
| 5,951,447 A | 9/1999 | Butler | |
| 5,951,449 A | 9/1999 | Oppriecht | |
| 5,957,814 A | 9/1999 | Eschenbach | |
| 5,961,423 A | 10/1999 | Sellers | |
| 5,961,430 A | 10/1999 | Zuckerman et al. | |
| 5,967,944 A | 10/1999 | Vittone et al. | |
| 5,967,954 A | 10/1999 | Habing | |
| 5,967,955 A | 10/1999 | Westfall et al. | |
| 5,971,902 A | 10/1999 | Robertson et al. | |
| 5,976,039 A | 11/1999 | Epel et al. | |
| 5,976,061 A | 11/1999 | Moon et al. | |
| 5,980,430 A | 11/1999 | Wang | |
| 5,980,432 A | 11/1999 | Ahman | |
| 5,984,798 A | 11/1999 | Gilmour | |
| 5,984,839 A | 11/1999 | Corkum | |
| 5,989,161 A | 11/1999 | Wang et al. | |
| 5,989,163 A | 11/1999 | Rodgers, Jr. | |
| 5,989,168 A | 11/1999 | See | |
| 5,991,143 A | 11/1999 | Wright et al. | |
| 5,993,358 A | 11/1999 | Gureghian et al. | |
| 5,993,359 A | 11/1999 | Eschenbach | |
| 5,993,362 A | 11/1999 | Ghobadi | |
| 5,997,447 A | 12/1999 | Giannelli et al. | |
| 5,997,450 A | 12/1999 | Wilkinson | |
| 6,003,481 A | 12/1999 | Pischinger et al. | |
| 6,004,244 A | 12/1999 | Simonson | |
| 6,006,379 A | 12/1999 | Hensley | |
| 6,010,432 A | 1/2000 | Vawter | |
| 6,012,591 A | 1/2000 | Brandenberg | |
| 6,012,772 A | 1/2000 | Conde et al. | |
| 6,013,011 A | 1/2000 | Moore et al. | |
| 6,015,367 A | 1/2000 | Scaramucci | |
| 6,015,368 A | 1/2000 | Clem | |
| 6,027,429 A | 2/2000 | Daniels | |
| 6,027,430 A | 2/2000 | Stearns et al. | |
| 6,027,432 A | 2/2000 | Cheng | |
| 6,029,858 A | 2/2000 | Srokose | |
| 6,030,320 A | 2/2000 | Stearns | |
| 6,030,323 A | 2/2000 | Fontenot | |
| 6,033,344 A | 3/2000 | Trulaske et al. | |
| 6,033,347 A | 3/2000 | Dalebout et al. | |
| 6,033,350 A | 3/2000 | Krull | |
| 6,036,622 A | 3/2000 | Gordon | |
| 6,042,512 A | 3/2000 | Eschenbach | |
| 6,042,514 A | 3/2000 | Abelbeck | |
| 6,042,515 A | 3/2000 | Wang | |
| 6,042,516 A | 3/2000 | Norton | |
| 6,042,518 A | 3/2000 | Hildebrandt et al. | |
| 6,042,523 A | 3/2000 | Graham | |
| 6,045,487 A | 4/2000 | Miller | |
| 6,045,488 A | 4/2000 | Eschenbach | |
| 6,045,490 A | 4/2000 | Shafer | |
| 6,045,491 A | 4/2000 | Elyse McNergney | |
| 6,050,920 A | 4/2000 | Ehrenfried | |
| 6,050,921 A | 4/2000 | Wang | |
| 6,050,922 A | 4/2000 | Wang | |
| 6,050,923 A | 4/2000 | Yu | |
| 6,053,844 A | 4/2000 | Clem | |
| 6,053,847 A | 4/2000 | Stearns et al. | |
| 6,053,848 A | 4/2000 | Eschenbach | |
| 6,055,747 A | 5/2000 | Lombardino | |
| 6,056,678 A | 5/2000 | Giannelli et al. | |
| 6,059,692 A | 5/2000 | Hickman | |
| 6,059,695 A | 5/2000 | Hung | |
| 6,063,009 A | 5/2000 | Stearns | |
| 6,066,075 A | 5/2000 | Poulton | |
| 6,068,578 A | 5/2000 | Wang | |
| 6,068,579 A | 5/2000 | Killian et al. | |
| 6,071,031 A | 6/2000 | Bailey | |
| 6,071,216 A | 6/2000 | Giannelli et al. | |
| 6,075,525 A | 6/2000 | Hsieh | |
| 6,077,196 A | 6/2000 | Eschenbach | |
| 6,077,198 A | 6/2000 | Eschenbach | |
| 6,077,199 A | 6/2000 | Hsu | |
| 6,077,200 A | 6/2000 | Lin | |
| 6,080,091 A | 6/2000 | Habing et al. | |
| 6,086,520 A | 7/2000 | Rodriquez | |
| 6,090,014 A | 7/2000 | Eschenbach | |
| 6,090,016 A | 7/2000 | Kuo | |
| 6,095,951 A | 8/2000 | Skowronski et al. | |
| 6,099,439 A | 8/2000 | Ryan et al. | |
| 6,102,412 A | 8/2000 | Staffaroni | |

(56) References Cited

U.S. PATENT DOCUMENTS

| | | |
|---|---|---|
| 6,102,832 A | 8/2000 | Tani |
| 6,110,076 A | 8/2000 | Hurt |
| 6,110,077 A | 8/2000 | Yu |
| 6,113,188 A | 9/2000 | Stewart et al. |
| 6,113,522 A | 9/2000 | Montgomery |
| 6,117,049 A | 9/2000 | Lowe |
| 6,120,421 A | 9/2000 | Kuo |
| 6,123,646 A | 9/2000 | Colassi |
| 6,123,647 A | 9/2000 | Mitchell |
| 6,123,648 A | 9/2000 | Stevens |
| 6,123,649 A | 9/2000 | Lee |
| 6,123,650 A | 9/2000 | Birrell |
| 6,125,851 A | 10/2000 | Walker et al. |
| 6,126,574 A | 10/2000 | Stearns et al. |
| 6,126,575 A | 10/2000 | Wang |
| 6,126,576 A | 10/2000 | Wang |
| 6,129,962 A | 10/2000 | Quigley et al. |
| 6,132,340 A | 10/2000 | Wang |
| 6,135,924 A | 10/2000 | Gibbs et al. |
| 6,135,925 A | 10/2000 | Liu |
| 6,142,870 A | 11/2000 | Wada et al. |
| 6,142,913 A | 11/2000 | Ewert |
| 6,142,914 A | 11/2000 | Crawford et al. |
| 6,142,915 A | 11/2000 | Eschenbach |
| 6,146,313 A | 11/2000 | Whan-Tong et al. |
| 6,146,315 A | 11/2000 | Schonenberger |
| 6,149,551 A | 11/2000 | Pyles et al. |
| 6,149,552 A | 11/2000 | Chen |
| 6,152,856 A | 11/2000 | Studor et al. |
| 6,152,859 A | 11/2000 | Stearns |
| 6,162,183 A | 12/2000 | Hoover |
| 6,163,451 A | 12/2000 | Chiu |
| 6,165,107 A | 12/2000 | Birrell |
| 6,168,551 B1 | 1/2001 | McGuinness |
| 6,171,216 B1 | 1/2001 | Wang |
| 6,174,267 B1 | 1/2001 | Dalebout |
| 6,174,268 B1 | 1/2001 | Novak |
| 6,176,814 B1 | 1/2001 | Ryan et al. |
| 6,179,753 B1 | 1/2001 | Barker et al. |
| 6,181,647 B1 | 1/2001 | Tipton et al. |
| 6,183,397 B1 | 2/2001 | Stearns et al. |
| 6,186,290 B1 | 2/2001 | Carlson |
| 6,186,460 B1 | 2/2001 | Lin |
| 6,186,929 B1 | 2/2001 | Endelman et al. |
| 6,189,846 B1 | 2/2001 | Wang |
| 6,190,289 B1 | 2/2001 | Pyles et al. |
| 6,193,635 B1 | 2/2001 | Webber et al. |
| 6,203,474 B1 | 3/2001 | Jones |
| 6,206,795 B1 | 3/2001 | Ou |
| 6,210,305 B1 | 4/2001 | Eschenbach |
| 6,213,919 B1 | 4/2001 | Wang |
| 6,215,870 B1 | 4/2001 | Hirai et al. |
| 6,217,487 B1 | 4/2001 | Reinert |
| 6,220,990 B1 | 4/2001 | Crivello |
| 6,220,995 B1 | 4/2001 | Chen |
| 6,224,516 B1 | 5/2001 | Disch |
| 6,224,519 B1 | 5/2001 | Doolittle |
| 6,230,047 B1 | 5/2001 | McHugh |
| 6,230,460 B1 | 5/2001 | Huyett |
| 6,231,482 B1 | 5/2001 | Thompson |
| 6,231,946 B1 | 5/2001 | Brown, Jr. et al. |
| 6,234,935 B1 | 5/2001 | Chu |
| 6,234,936 B1 | 5/2001 | Wang |
| 6,237,583 B1 | 5/2001 | Ripley et al. |
| 6,238,323 B1 | 5/2001 | Simonson |
| 6,241,638 B1 | 6/2001 | Hurt |
| 6,244,988 B1 | 6/2001 | Delman |
| 6,244,992 B1 | 6/2001 | James |
| 6,245,001 B1 | 6/2001 | Siaperas |
| 6,251,047 B1 | 6/2001 | Stearns et al. |
| 6,254,514 B1 | 7/2001 | Maresh et al. |
| 6,254,515 B1 | 7/2001 | Carman et al. |
| 6,261,209 B1 | 7/2001 | Coody |
| 6,264,586 B1 | 7/2001 | Webber |
| 6,267,710 B1 | 7/2001 | Liu |
| 6,273,842 B1 | 8/2001 | Wang |
| 6,273,843 B1 | 8/2001 | Lo |
| 6,276,749 B1 | 8/2001 | Okazawa et al. |
| 6,277,054 B1 | 8/2001 | Kuo |
| 6,277,056 B1 | 8/2001 | McBride et al. |
| 6,280,361 B1 | 8/2001 | Harvey et al. |
| 6,280,362 B1 | 8/2001 | Dalebout et al. |
| 6,280,367 B1 | 8/2001 | Arsenault |
| 6,282,816 B1 | 9/2001 | Rosendahl |
| 6,283,896 B1 | 9/2001 | Grunfeld |
| 6,287,240 B1 | 9/2001 | Trabbic |
| 6,293,375 B1 | 9/2001 | Chen |
| 6,299,959 B1 | 10/2001 | Squires et al. |
| 6,302,815 B1 | 10/2001 | Shishido et al. |
| 6,302,826 B1 | 10/2001 | Lee |
| 6,302,828 B1 | 10/2001 | Martin et al. |
| 6,302,829 B1 | 10/2001 | Schmidt |
| 6,302,830 B1 | 10/2001 | Stearns |
| 6,302,833 B1 | 10/2001 | Ellis et al. |
| 6,306,108 B1 | 10/2001 | Butler |
| 6,307,167 B1 | 10/2001 | Kajio et al. |
| 6,312,363 B1 | 11/2001 | Watterson et al. |
| 6,314,667 B1 | 11/2001 | Rife et al. |
| 6,315,486 B1 | 11/2001 | Lunz |
| 6,322,059 B1 | 11/2001 | Kelm et al. |
| 6,322,481 B1 | 11/2001 | Krull |
| 6,325,745 B1 | 12/2001 | Yu |
| 6,325,746 B1 | 12/2001 | Wang |
| 6,328,676 B1 | 12/2001 | Alessandri |
| 6,328,677 B1 | 12/2001 | Drapeau |
| 6,334,624 B1 | 1/2002 | Giglio |
| 6,344,986 B1 | 2/2002 | Jain et al. |
| 6,347,603 B1 | 2/2002 | Felger |
| 6,348,028 B1 | 2/2002 | Cragg |
| 6,350,218 B1 | 2/2002 | Dalebout et al. |
| 6,352,494 B2 | 3/2002 | McAlonan |
| 6,357,077 B1 | 3/2002 | Jones, Jr. et al. |
| 6,361,476 B1 | 3/2002 | Eschenbach |
| 6,368,252 B1 | 4/2002 | Stearns |
| 6,368,254 B1 | 4/2002 | Wall |
| 6,371,738 B2 | 4/2002 | Jones |
| 6,371,895 B1 | 4/2002 | Endelman et al. |
| 6,375,580 B1 | 4/2002 | Schmidt |
| 6,379,289 B1 | 4/2002 | Gossie |
| 6,382,627 B1 | 5/2002 | Lundberg |
| 6,383,120 B1 | 5/2002 | Lo |
| 6,387,015 B1 | 5/2002 | Watson |
| 6,387,016 B1 | 5/2002 | Lo |
| 6,390,953 B1 | 5/2002 | Maresh |
| 6,390,955 B1 | 5/2002 | Wang |
| 6,394,239 B1 | 5/2002 | Carlson |
| 6,397,797 B1 | 6/2002 | Kolmanovsky et al. |
| 6,398,695 B2 | 6/2002 | Miller |
| 6,402,666 B2 | 6/2002 | Krull |
| 6,409,632 B1 | 6/2002 | Eschenbach |
| 6,409,633 B1 | 6/2002 | Abelbeck |
| 6,413,197 B2 | 7/2002 | McKechnie et al. |
| 6,416,442 B1 | 7/2002 | Stearns et al. |
| 6,416,444 B1 | 7/2002 | Lim |
| 6,419,611 B1 | 7/2002 | Levine et al. |
| 6,422,976 B1 | 7/2002 | Eschenbach |
| 6,422,977 B1 | 7/2002 | Eschenbach |
| 6,422,983 B1 | 7/2002 | Weck |
| 6,428,449 B1 | 8/2002 | Apseloff |
| 6,430,997 B1 | 8/2002 | French et al. |
| 6,432,026 B1 | 8/2002 | Wang |
| 6,435,466 B1 | 8/2002 | Adams |
| 6,436,007 B1 | 8/2002 | Eschenbach |
| 6,436,008 B1 | 8/2002 | Skowronski et al. |
| 6,440,013 B1 | 8/2002 | Brown |
| 6,440,042 B2 | 8/2002 | Eschenbach |
| 6,443,875 B1 | 9/2002 | Golen, Jr. et al. |
| 6,447,424 B1 | 9/2002 | Ashby et al. |
| 6,447,430 B1 | 9/2002 | Webb et al. |
| 6,450,284 B1 | 9/2002 | Sakyo et al. |
| 6,450,922 B1 | 9/2002 | Henderson et al. |
| 6,450,923 B1 | 9/2002 | Vatti |
| 6,450,925 B1 | 9/2002 | Kuo |
| 6,454,682 B1 | 9/2002 | Kuo |

(56) References Cited

U.S. PATENT DOCUMENTS

| | | |
|---|---|---|
| 6,455,960 B1 | 9/2002 | Trago et al. |
| 6,458,060 B1 | 10/2002 | Watterson et al. |
| 6,461,275 B1 | 10/2002 | Wang et al. |
| 6,461,279 B1 | 10/2002 | Kuo |
| 6,466,460 B1 | 10/2002 | Rein et al. |
| 6,468,189 B2 | 10/2002 | Alessandri |
| 6,471,622 B1 | 10/2002 | Hammer et al. |
| 6,475,121 B2 | 11/2002 | Wang |
| 6,478,721 B1 | 11/2002 | Hunter |
| 6,482,130 B1 | 11/2002 | Pasero et al. |
| 6,482,132 B2 | 11/2002 | Eschenbach |
| 6,485,397 B1 | 11/2002 | Manderbacka |
| 6,488,020 B1 | 12/2002 | Rosas-Magallan |
| 6,491,610 B1 | 12/2002 | Henn |
| 6,494,814 B1 | 12/2002 | Wang |
| 6,494,817 B2 | 12/2002 | Lake |
| 6,500,097 B1 | 12/2002 | Hall |
| 6,503,173 B2 | 1/2003 | Clem |
| 6,505,503 B1 | 1/2003 | Teresi et al. |
| 6,513,669 B2 | 2/2003 | Ozawa et al. |
| 6,514,180 B1 | 2/2003 | Rawls |
| 6,520,891 B1 | 2/2003 | Stephens, Jr. |
| 6,527,674 B1 | 3/2003 | Clem |
| 6,527,678 B1 | 3/2003 | Wang |
| 6,527,685 B2 | 3/2003 | Endelman et al. |
| 6,527,796 B1 | 3/2003 | Magovern |
| 6,530,864 B1 | 3/2003 | Parks |
| 6,533,707 B2 | 3/2003 | Wang |
| 6,537,184 B2 | 3/2003 | Kim |
| 6,539,931 B2 | 4/2003 | Trajkovic et al. |
| 6,543,247 B2 | 4/2003 | Strauss |
| 6,544,146 B1 | 4/2003 | Stearns et al. |
| 6,547,701 B1 | 4/2003 | Eschenbach |
| 6,547,702 B1 | 4/2003 | Heidecke |
| 6,551,218 B2 | 4/2003 | Goh |
| 6,551,223 B2 | 4/2003 | Cheng |
| 6,554,749 B2 | 4/2003 | Iund et al. |
| 6,558,301 B1 | 5/2003 | Jackson |
| 6,561,960 B2 | 5/2003 | Webber |
| 6,563,489 B1 | 5/2003 | Latypov et al. |
| 6,569,061 B2 | 5/2003 | Stearns et al. |
| 6,569,062 B2 | 5/2003 | Wang |
| 6,572,511 B1 | 6/2003 | Volpe |
| 6,572,512 B2 | 6/2003 | Anderson et al. |
| 6,572,513 B2 | 6/2003 | Whan-Tong et al. |
| 6,575,878 B1 | 6/2003 | Choy |
| 6,579,210 B1 | 6/2003 | Stearns et al. |
| 6,582,344 B2 | 6/2003 | Tang |
| 6,585,624 B1 | 7/2003 | Chen |
| 6,585,626 B2 | 7/2003 | McBride |
| 6,589,138 B2 | 7/2003 | Dyer et al. |
| 6,592,502 B1 | 7/2003 | Phillips |
| 6,599,223 B2 | 7/2003 | Wang |
| 6,601,016 B1 | 7/2003 | Brown et al. |
| 6,601,358 B2 | 8/2003 | Panatta |
| 6,601,825 B2 | 8/2003 | Bressner et al. |
| 6,604,008 B2 | 8/2003 | Chudley et al. |
| 6,605,020 B1 | 8/2003 | Huang |
| 6,609,478 B2 | 8/2003 | Del Valle |
| 6,610,063 B2 | 8/2003 | Kumar et al. |
| 6,612,969 B2 | 9/2003 | Eschenbach |
| 6,612,971 B1 | 9/2003 | Morris |
| 6,619,681 B2 | 9/2003 | Gutierrez |
| 6,620,079 B2 | 9/2003 | Kuo |
| 6,623,407 B2 | 9/2003 | Novak |
| 6,623,409 B1 | 9/2003 | Abelbeck |
| 6,626,799 B2 | 9/2003 | Watterson et al. |
| 6,626,802 B2 | 9/2003 | Rodgers, Jr. |
| 6,626,803 B1 | 9/2003 | Oglesby et al. |
| 6,629,902 B2 | 10/2003 | Murphy et al. |
| 6,629,909 B1 | 10/2003 | Stearns et al. |
| 6,629,910 B1 | 10/2003 | Krull |
| 6,632,161 B1 | 10/2003 | Nir |
| 6,634,996 B2 | 10/2003 | Jacobsen |
| 6,637,811 B2 | 10/2003 | Zheng |
| 6,637,818 B2 | 10/2003 | Williams |
| 6,645,125 B1 | 11/2003 | Stearns et al. |
| 6,645,126 B1 | 11/2003 | Martin et al. |
| 6,645,130 B2 | 11/2003 | Webber |
| 6,648,800 B2 | 11/2003 | Stearns et al. |
| 6,648,801 B2 | 11/2003 | Stearns et al. |
| 6,648,802 B2 | 11/2003 | Ware |
| 6,652,424 B2 | 11/2003 | Dalebout |
| 6,652,425 B1 | 11/2003 | Martin et al. |
| 6,652,429 B2 | 11/2003 | Bushnell |
| 6,660,949 B2 | 12/2003 | Kamino et al. |
| 6,661,136 B1 | 12/2003 | Lee |
| 6,663,127 B2 | 12/2003 | Miller |
| 6,663,498 B2 | 12/2003 | Stipan |
| 6,663,500 B2 | 12/2003 | Huang |
| 6,666,800 B2 | 12/2003 | Krull |
| 6,666,801 B1 | 12/2003 | Michalow |
| 6,668,678 B1 | 12/2003 | Baba et al. |
| 6,669,600 B2 | 12/2003 | Warner |
| 6,669,609 B2 | 12/2003 | Gerschefske et al. |
| 6,671,975 B2 | 1/2004 | Hennessey |
| 6,672,992 B1 | 1/2004 | Lo et al. |
| 6,672,994 B1 | 1/2004 | Stearns et al. |
| 6,676,530 B2 | 1/2004 | Lochtefeld |
| 6,676,572 B2 | 1/2004 | Wang |
| 6,676,579 B1 | 1/2004 | Lin |
| 6,679,816 B1 | 1/2004 | Krull |
| 6,679,820 B2 | 1/2004 | Barkus et al. |
| 6,681,704 B1 | 1/2004 | Brookhiser |
| 6,681,728 B2 | 1/2004 | Haghgooie |
| 6,682,460 B2 | 1/2004 | Lo |
| 6,682,461 B2 | 1/2004 | Wang |
| 6,685,601 B1 | 2/2004 | Knapp |
| 6,685,602 B2 | 2/2004 | Colosky, Jr. et al. |
| 6,685,607 B1 | 2/2004 | Olson |
| 6,689,019 B2 | 2/2004 | Ohrt et al. |
| 6,695,694 B2 | 2/2004 | Ishikawa et al. |
| 6,698,110 B1 | 3/2004 | Robbins |
| 6,699,159 B2 | 3/2004 | Rouse |
| 6,699,162 B2 | 3/2004 | Chen |
| 6,702,719 B1 | 3/2004 | Brown et al. |
| 6,705,977 B1 | 3/2004 | Ziak |
| 6,708,427 B2 | 3/2004 | Sussmann et al. |
| 6,712,737 B1 | 3/2004 | Nusbaum |
| 6,716,142 B2 | 4/2004 | Kuo |
| 6,716,144 B1 | 4/2004 | Shifferaw |
| 6,719,667 B2 | 4/2004 | Wong et al. |
| 6,719,669 B1 | 4/2004 | Wang |
| 6,723,413 B2 | 4/2004 | Walters |
| 6,726,600 B2 | 4/2004 | Miller |
| 6,726,601 B1 | 4/2004 | Beutel |
| 6,726,602 B2 | 4/2004 | Chang |
| 6,730,002 B2 | 5/2004 | Hald et al. |
| 6,733,423 B1 | 5/2004 | Chang |
| 6,733,424 B2 | 5/2004 | Krull |
| 6,736,360 B1 | 5/2004 | Buczek |
| 6,738,274 B2 | 5/2004 | Prasad et al. |
| 6,740,009 B1 | 5/2004 | Hall |
| 6,741,052 B2 | 5/2004 | Fitzgibbon |
| 6,743,153 B2 | 6/2004 | Watterson et al. |
| 6,746,371 B1 | 6/2004 | Brown et al. |
| 6,747,427 B1 | 6/2004 | Carson |
| 6,749,540 B1 | 6/2004 | Pasero et al. |
| 6,749,542 B2 | 6/2004 | Wu |
| 6,758,790 B1 | 7/2004 | Ellis |
| 6,758,791 B1 | 7/2004 | Kuo |
| 6,758,792 B1 | 7/2004 | Chang |
| 6,761,387 B2 | 7/2004 | Sloss |
| 6,761,667 B1 | 7/2004 | Cutler et al. |
| 6,764,429 B1 | 7/2004 | Michalow |
| 6,764,430 B1 | 7/2004 | Fencel |
| 6,764,431 B1 | 7/2004 | Yoss |
| 6,765,726 B2 | 7/2004 | French et al. |
| 6,767,314 B2 | 7/2004 | Thompson |
| 6,770,015 B2 | 8/2004 | Simonson |
| 6,776,740 B1 | 8/2004 | Anderson et al. |
| 6,778,938 B1 | 8/2004 | Ng et al. |
| 6,783,482 B2 | 8/2004 | Oglesby et al. |
| 6,786,821 B2 | 9/2004 | Nobe et al. |

(56) References Cited

U.S. PATENT DOCUMENTS

| | | |
|---|---|---|
| 6,786,847 B1 | 9/2004 | Morgan et al. |
| 6,786,848 B2 | 9/2004 | Yamashita et al. |
| 6,786,850 B2 | 9/2004 | Nizamuddin |
| 6,786,852 B2 | 9/2004 | Watterson et al. |
| 6,790,162 B1 | 9/2004 | Ellis et al. |
| 6,793,609 B1 | 9/2004 | Fan |
| 6,796,159 B2 | 9/2004 | Kelm et al. |
| 6,796,927 B2 | 9/2004 | Toyama |
| 6,808,458 B1 | 10/2004 | Jung |
| 6,808,475 B2 | 10/2004 | Kehrbaum |
| 6,811,519 B2 | 11/2004 | Kuo |
| 6,811,520 B2 | 11/2004 | Wu |
| 6,817,117 B1 | 11/2004 | Campbell |
| 6,817,968 B2 | 11/2004 | Galbraith et al. |
| 6,821,230 B2 | 11/2004 | Dalebout et al. |
| 6,824,210 B2 | 11/2004 | Zheng |
| 6,824,502 B1 | 11/2004 | Huang |
| 6,830,540 B2 | 12/2004 | Watterson |
| 6,830,541 B2 | 12/2004 | Wu |
| 6,835,166 B1 | 12/2004 | Stearns et al. |
| 6,837,829 B2 | 1/2005 | Eschenbach |
| 6,837,830 B2 | 1/2005 | Eldridge |
| 6,837,838 B2 | 1/2005 | List |
| 6,840,892 B1 | 1/2005 | Wu |
| 6,842,928 B2 | 1/2005 | Yang et al. |
| 6,843,732 B1 | 1/2005 | Huang |
| 6,846,272 B2 | 1/2005 | Rosenow et al. |
| 6,849,032 B2 | 2/2005 | Chu |
| 6,852,068 B2 | 2/2005 | Ogawa |
| 6,855,093 B2 | 2/2005 | Anderson et al. |
| 6,855,097 B2 | 2/2005 | Krull |
| 6,857,993 B2 | 2/2005 | Yeh |
| 6,860,836 B1 | 3/2005 | Wu |
| 6,860,839 B1 | 3/2005 | Dice |
| 6,872,168 B2 | 3/2005 | Wang et al. |
| 6,872,175 B2 | 3/2005 | Lin |
| 6,875,157 B1 | 4/2005 | Wang |
| 6,875,160 B2 | 4/2005 | Watterson et al. |
| 6,878,101 B2 | 4/2005 | Colley |
| 6,880,487 B2 | 4/2005 | Reinkensmeyer et al. |
| 6,881,176 B2 | 4/2005 | Oishi et al. |
| 6,887,185 B1 | 5/2005 | Kuo |
| 6,887,190 B1 | 5/2005 | Azari |
| 6,893,383 B1 | 5/2005 | Chang et al. |
| 6,896,645 B1 | 5/2005 | Krull |
| 6,899,657 B2 | 5/2005 | Chuang |
| 6,899,659 B2 | 5/2005 | Anderson et al. |
| 6,902,513 B1 | 6/2005 | Mcclure |
| 6,902,515 B2 | 6/2005 | Howell et al. |
| 6,905,446 B2 | 6/2005 | Greenland |
| 6,908,416 B2 | 6/2005 | Mercado et al. |
| 6,908,417 B2 | 6/2005 | Jackson |
| 6,913,562 B2 | 7/2005 | Chen |
| 6,913,563 B1 | 7/2005 | Chen |
| 6,916,278 B2 | 7/2005 | Webber |
| 6,918,858 B2 | 7/2005 | Watterson et al. |
| 6,918,859 B1 | 7/2005 | Yeh |
| 6,918,860 B1 | 7/2005 | Nusbaum |
| 6,921,354 B1 | 7/2005 | Shifferaw |
| 6,921,355 B2 | 7/2005 | Campanaro et al. |
| 6,923,746 B1 | 8/2005 | Skowronski et al. |
| 6,923,747 B1 | 8/2005 | Chu |
| 6,926,644 B2 | 8/2005 | Chen |
| 6,926,646 B1 | 8/2005 | Nguyen |
| 6,932,745 B1 | 8/2005 | Ellis |
| 6,939,271 B1 | 9/2005 | Whan-Tong et al. |
| 6,944,294 B2 | 9/2005 | Tsay |
| 6,945,912 B2 | 9/2005 | Levi |
| 6,945,917 B1 | 9/2005 | Baatz |
| 6,949,053 B1 | 9/2005 | Stearns |
| 6,949,054 B1 | 9/2005 | Stearns |
| 6,953,418 B1 | 10/2005 | Chen |
| 6,964,632 B1 | 11/2005 | Ko |
| 6,966,872 B2 | 11/2005 | Eschenbach |
| 6,974,404 B1 | 12/2005 | Watterson et al. |
| 6,976,698 B2 | 12/2005 | Kuiken |
| 6,979,283 B2 | 12/2005 | Pan |
| 6,991,588 B1 | 1/2006 | Adams |
| 6,994,306 B1 | 2/2006 | Sweere et al. |
| 6,994,657 B1 | 2/2006 | Eschenbach |
| 6,997,852 B2 | 2/2006 | Watterson et al. |
| 6,997,856 B2 | 2/2006 | Krull |
| 7,001,288 B2 | 2/2006 | Harrell |
| 7,003,122 B2 | 2/2006 | Chen |
| 7,004,271 B1 | 2/2006 | Kamen et al. |
| 7,004,887 B2 | 2/2006 | Pan et al. |
| 7,004,888 B1 | 2/2006 | Weng |
| 7,008,359 B2 | 3/2006 | Fan et al. |
| 7,011,326 B1 | 3/2006 | Schroeder et al. |
| 7,011,607 B2 | 3/2006 | Kolda et al. |
| 7,011,609 B1 | 3/2006 | Kuo |
| 7,022,048 B1 | 4/2006 | Fernandez |
| 7,022,049 B2 | 4/2006 | Ryan et al. |
| 7,022,051 B2 | 4/2006 | Ota |
| 7,032,870 B2 | 4/2006 | Sweere et al. |
| 7,033,176 B2 | 4/2006 | Feldman |
| 7,033,306 B2 | 4/2006 | Graber |
| 7,039,263 B2 | 5/2006 | Towle |
| 7,041,034 B1 | 5/2006 | Stearns et al. |
| 7,041,038 B1 | 5/2006 | Smith |
| 7,041,041 B1 | 5/2006 | Evans |
| 7,044,891 B1 | 5/2006 | Rivera |
| 7,052,426 B2 | 5/2006 | Battat et al. |
| 7,052,440 B2 | 5/2006 | Pyles et al. |
| 7,052,444 B2 | 5/2006 | Webber |
| 7,052,446 B2 | 5/2006 | Morris et al. |
| 7,055,899 B2 | 6/2006 | Zhurong et al. |
| 7,060,005 B2 | 6/2006 | Carlsen et al. |
| 7,060,006 B1 | 6/2006 | Watterson et al. |
| 7,070,542 B2 | 7/2006 | Reyes et al. |
| 7,070,545 B2 | 7/2006 | Lull et al. |
| 7,073,852 B1 | 7/2006 | Zheng |
| 7,077,788 B2 | 7/2006 | Chang |
| 7,077,791 B2 | 7/2006 | Krull |
| 7,081,073 B1 | 7/2006 | Smith |
| 7,082,703 B2 | 8/2006 | Greene et al. |
| 7,086,994 B2 | 8/2006 | Turak et al. |
| 7,090,621 B2 | 8/2006 | Loane |
| 7,090,622 B2 | 8/2006 | Hetrick |
| 7,097,591 B2 | 8/2006 | Moon |
| 7,097,593 B2 | 8/2006 | Chang |
| 7,100,517 B1 | 9/2006 | Godwin |
| 7,101,319 B1 | 9/2006 | Potts |
| 7,101,322 B2 | 9/2006 | Carle |
| 7,101,330 B2 | 9/2006 | Elbaz et al. |
| 7,104,926 B2 | 9/2006 | Carlson |
| 7,104,937 B2 | 9/2006 | Arbuckle |
| 7,108,641 B2 | 9/2006 | Pertegaz-Esteban |
| 7,108,659 B2 | 9/2006 | Ross et al. |
| 7,115,073 B2 | 10/2006 | Nizamuddin |
| 7,125,371 B2 | 10/2006 | Henderson |
| 7,132,939 B2 | 11/2006 | Tyndall et al. |
| 7,140,626 B1 | 11/2006 | Keay |
| 7,141,008 B2 | 11/2006 | Krull et al. |
| 7,156,776 B2 | 1/2007 | Maser |
| 7,163,493 B1 | 1/2007 | Kuo |
| 7,163,498 B1 | 1/2007 | Abelbeck |
| 7,163,500 B2 | 1/2007 | Endelman et al. |
| 7,166,062 B1 | 1/2007 | Watterson et al. |
| 7,166,064 B2 * | 1/2007 | Watterson ............ A63B 21/005 482/51 |
| 7,166,067 B2 | 1/2007 | Talish et al. |
| 7,168,668 B2 | 1/2007 | Coyle |
| 7,169,087 B2 | 1/2007 | Ercanbrack et al. |
| 7,169,088 B2 | 1/2007 | Rodgers, Jr. |
| 7,172,531 B2 | 2/2007 | Rodgers, Jr. |
| 7,175,193 B2 | 2/2007 | Wu |
| 7,179,207 B2 | 2/2007 | Gerschefske |
| 7,179,208 B1 | 2/2007 | Nalley |
| 7,179,209 B2 | 2/2007 | Sechrest et al. |
| 7,186,189 B2 | 3/2007 | Huang |
| 7,192,387 B2 | 3/2007 | Mendel |
| 7,192,388 B2 | 3/2007 | Dalebout et al. |
| 7,195,568 B2 | 3/2007 | Huang |

(56) References Cited

U.S. PATENT DOCUMENTS

| | | |
|---|---|---|
| 7,201,705 B2 | 4/2007 | Rodgers, Jr. |
| 7,201,707 B1 | 4/2007 | Moon |
| 7,204,328 B2 | 4/2007 | LoPresti |
| 7,211,029 B2 | 5/2007 | Kau |
| 7,217,224 B2 | 5/2007 | Thomas |
| 7,217,225 B2 | 5/2007 | Husted et al. |
| 7,220,219 B2 | 5/2007 | Papadopoulos et al. |
| 7,220,221 B2 | 5/2007 | Mosimann et al. |
| 7,223,209 B2 | 5/2007 | Lee |
| 7,223,216 B1 | 5/2007 | McBride |
| 7,225,694 B2 | 6/2007 | Said |
| 7,226,402 B1 | 6/2007 | Joya |
| 7,235,942 B2 | 6/2007 | Nagaoka et al. |
| 7,238,147 B2 | 7/2007 | Mills et al. |
| 7,247,128 B2 | 7/2007 | Oga |
| 7,250,022 B2 | 7/2007 | Dalebout |
| 7,257,468 B1 | 8/2007 | Costa et al. |
| 7,258,651 B2 | 8/2007 | Clarke |
| 7,264,554 B2 | 9/2007 | Bentley |
| 7,269,038 B2 | 9/2007 | Shekhawat |
| 7,278,934 B2 | 10/2007 | McBride et al. |
| 7,278,966 B2 | 10/2007 | Hjelt et al. |
| 7,279,868 B2 | 10/2007 | Lanni |
| 7,285,075 B2 | 10/2007 | Cutler et al. |
| 7,287,770 B2 | 10/2007 | Drabant et al. |
| 7,290,760 B1 | 11/2007 | Lindsay |
| 7,291,096 B2 | 11/2007 | Ho |
| 7,292,151 B2 | 11/2007 | Ferguson |
| 7,293,510 B1 | 11/2007 | Siao et al. |
| 7,294,094 B1 | 11/2007 | Howle |
| 7,294,100 B2 | 11/2007 | Bull |
| 7,303,508 B2 | 12/2007 | Toyama et al. |
| 7,303,510 B2 | 12/2007 | Gebhardt |
| 7,311,640 B2 | 12/2007 | Baatz |
| 7,316,633 B2 | 1/2008 | Liao et al. |
| 7,319,457 B2 | 1/2008 | Lin et al. |
| 7,322,907 B2 | 1/2008 | Bowser |
| 7,334,350 B2 | 2/2008 | Ellis, III |
| 7,335,139 B2 | 2/2008 | Bartholomew et al. |
| 7,335,140 B2 | 2/2008 | Webber et al. |
| 7,335,147 B2 | 2/2008 | Jones |
| 7,344,481 B2 | 3/2008 | Watterson et al. |
| 7,346,935 B1 | 3/2008 | Patterson |
| 7,347,806 B2 | 3/2008 | Nakano et al. |
| 7,351,187 B2 | 4/2008 | Seliber |
| 7,352,365 B2 | 4/2008 | Trachte |
| 7,354,380 B2 | 4/2008 | Volpe, Jr. |
| 7,357,758 B2 | 4/2008 | Polk, III |
| 7,359,121 B2 | 4/2008 | French et al. |
| 7,361,125 B2 | 4/2008 | Webber et al. |
| 7,364,538 B2 | 4/2008 | Aucamp |
| 7,366,921 B2 | 4/2008 | Ranganathan |
| 7,367,926 B2 | 5/2008 | Clark |
| 7,369,121 B2 | 5/2008 | Lane |
| 7,374,522 B2 | 5/2008 | Arnold |
| 7,377,881 B2 | 5/2008 | Moon |
| 7,384,013 B2 | 6/2008 | Yen |
| 7,393,308 B1 | 7/2008 | Huang |
| 7,402,145 B1 | 7/2008 | Woggon |
| 7,413,532 B1 | 8/2008 | Monsrud et al. |
| 7,425,189 B1 | 9/2008 | Eschenbach |
| 7,428,760 B2 | 9/2008 | McCrimmon |
| 7,429,236 B2 | 9/2008 | Dalebout et al. |
| 7,432,677 B2 | 10/2008 | Heydt et al. |
| 7,435,205 B2 | 10/2008 | Reyes et al. |
| 7,455,621 B1 | 11/2008 | Anthony |
| 7,455,626 B2 | 11/2008 | Trevino et al. |
| 7,455,628 B2 | 11/2008 | Stearns |
| 7,470,234 B1 | 12/2008 | Elhag et al. |
| 7,475,613 B2 | 1/2009 | Bailey |
| 7,488,277 B1 | 2/2009 | Knapp |
| 7,494,450 B2 | 2/2009 | Solomon |
| 7,497,784 B2 | 3/2009 | Henry |
| 7,507,187 B2 | 3/2009 | Dyer et al. |
| 7,507,189 B2 | 3/2009 | Krull |
| 7,510,511 B2 | 3/2009 | Von Detten |
| 7,517,303 B2 | 4/2009 | Crawford et al. |
| 7,520,840 B2 | 4/2009 | Shifferaw |
| 7,524,272 B2 | 4/2009 | Bruck et al. |
| 7,525,293 B1 | 4/2009 | Notohamiprodjo et al. |
| 7,537,546 B2 | 5/2009 | Watterson et al. |
| 7,537,549 B2 | 5/2009 | Nelson et al. |
| 7,537,550 B1 | 5/2009 | Krull |
| 7,540,828 B2 | 6/2009 | Watterson et al. |
| 7,540,829 B1 | 6/2009 | Lin |
| 7,544,153 B2 | 6/2009 | Trevino et al. |
| 7,553,260 B2 | 6/2009 | Piaget et al. |
| 7,553,262 B2 | 6/2009 | Piane, Jr. |
| 7,556,590 B2 | 7/2009 | Watterson et al. |
| 7,556,591 B2 | 7/2009 | Chuang |
| 7,559,879 B2 | 7/2009 | Anderson et al. |
| 7,563,203 B2 | 7/2009 | Dalebout et al. |
| 7,563,205 B2 | 7/2009 | Alling |
| 7,569,000 B2 | 8/2009 | Wang |
| 7,569,004 B2 | 8/2009 | Kolomeir |
| 7,575,537 B2 | 8/2009 | Ellis |
| 7,585,251 B2 | 9/2009 | Doody, Jr. et al. |
| 7,585,254 B1 | 9/2009 | Vittone |
| 7,585,258 B2 | 9/2009 | Watson et al. |
| 7,591,770 B2 | 9/2009 | Stewart et al. |
| 7,591,795 B2 | 9/2009 | Whalen et al. |
| 7,594,877 B2 | 9/2009 | Anderson et al. |
| 7,594,878 B1 | 9/2009 | Joannou |
| 7,601,101 B2 | 10/2009 | Jackson et al. |
| 7,602,301 B1 | 10/2009 | Stirling et al. |
| 7,604,571 B2 | 10/2009 | Wilkins |
| 7,604,572 B2 | 10/2009 | Stanford |
| 7,604,573 B2 | 10/2009 | Dalebout et al. |
| 7,608,015 B2 | 10/2009 | Radow |
| 7,608,021 B1 | 10/2009 | Nalley |
| 7,608,023 B2 | 10/2009 | Casagrande |
| 7,614,639 B2 | 11/2009 | Tholkes et al. |
| 7,614,981 B2 | 11/2009 | Cao |
| 7,618,346 B2 | 11/2009 | Crawford et al. |
| 7,618,350 B2 | 11/2009 | Dalebout et al. |
| 7,621,850 B2 | 11/2009 | Piaget et al. |
| 7,621,855 B1 | 11/2009 | Krull |
| 7,625,314 B2 | 12/2009 | Ungari |
| 7,628,730 B1 | 12/2009 | Watterson et al. |
| 7,628,732 B1 | 12/2009 | Porszasz et al. |
| 7,637,847 B1 | 12/2009 | Hickman |
| 7,637,850 B2 | 12/2009 | Lin |
| 7,639,520 B1 | 12/2009 | Zansky et al. |
| 7,645,212 B2 | 1/2010 | Ashby et al. |
| 7,645,214 B2 | 1/2010 | Lull |
| 7,645,218 B2 | 1/2010 | Potok et al. |
| 7,647,196 B2 | 1/2010 | Kahn et al. |
| 7,648,446 B2 | 1/2010 | Chiles et al. |
| 7,651,442 B2 | 1/2010 | Carlson |
| 7,654,229 B2 | 2/2010 | Smith |
| 7,658,694 B2 | 2/2010 | Ungari |
| 7,658,695 B1 | 2/2010 | Amsbury et al. |
| 7,658,698 B2 | 2/2010 | Pacheco et al. |
| 7,670,263 B2 | 3/2010 | Ellis |
| 7,674,205 B2 | 3/2010 | Dalebout et al. |
| 7,674,206 B2 | 3/2010 | Jones |
| 7,677,518 B2 | 3/2010 | Chouinard et al. |
| 7,682,286 B2 | 3/2010 | Badarneh et al. |
| 7,682,287 B1 | 3/2010 | Hsieh |
| 7,682,290 B2 | 3/2010 | Liao et al. |
| 7,682,291 B2 | 3/2010 | Gill et al. |
| 7,690,556 B1 | 4/2010 | Kahn et al. |
| 7,695,409 B2 | 4/2010 | Helie et al. |
| 7,704,191 B2 | 4/2010 | Smith et al. |
| 7,704,192 B2 | 4/2010 | Dyer et al. |
| 7,708,668 B2 | 5/2010 | Rodgers, Jr. |
| 7,708,672 B2 | 5/2010 | Gibson et al. |
| 7,713,172 B2 | 5/2010 | Watterson et al. |
| 7,713,177 B2 | 5/2010 | Lo |
| 7,717,826 B2 | 5/2010 | Cox et al. |
| 7,717,828 B2 | 5/2010 | Simonson et al. |
| 7,717,830 B1 | 5/2010 | Charniga et al. |
| 7,722,503 B1 | 5/2010 | Smith et al. |
| 7,722,509 B2 | 5/2010 | Eder |

(56) References Cited

U.S. PATENT DOCUMENTS

| | | | |
|---|---|---|---|
| 7,731,634 B2 | 6/2010 | Stewart et al. |
| 7,736,272 B2 | 6/2010 | Martens |
| 7,736,273 B2 | 6/2010 | Cox et al. |
| 7,736,279 B2 | 6/2010 | Dalebout et al. |
| 7,736,280 B2 | 6/2010 | Weier et al. |
| 7,736,281 B2 | 6/2010 | Corbalis et al. |
| 7,740,563 B2 | 6/2010 | Dalebout et al. |
| 7,745,716 B1 | 6/2010 | Murphy |
| 7,749,137 B2 | 7/2010 | Watt et al. |
| 7,753,830 B1 | 7/2010 | Marsh et al. |
| 7,753,861 B1 | 7/2010 | Kahn et al. |
| 7,758,469 B2 | 7/2010 | Dyer et al. |
| 7,762,952 B2 | 7/2010 | Lee et al. |
| 7,766,797 B2 | 8/2010 | Dalebout |
| 7,771,319 B1 | 8/2010 | Lannon |
| 7,771,320 B2 | 8/2010 | Riley et al. |
| 7,771,329 B2 | 8/2010 | Dalebout et al. |
| 7,775,128 B2 | 8/2010 | Roessingh et al. |
| 7,775,936 B2 | 8/2010 | Wilkinson |
| 7,775,943 B2 | 8/2010 | Vittone |
| 7,780,578 B2 | 8/2010 | Packham |
| 7,789,800 B1 | 9/2010 | Watterson et al. |
| 7,794,363 B2 | 9/2010 | Wang |
| 7,795,824 B2 | 9/2010 | Shen et al. |
| 7,806,780 B1 | 10/2010 | Plunkett |
| 7,806,805 B2 | 10/2010 | Barufka et al. |
| 7,811,209 B2 | 10/2010 | Crawford et al. |
| 7,815,550 B2 | 10/2010 | Watterson et al. |
| 7,815,554 B2 | 10/2010 | Gibson et al. |
| 7,837,161 B2 | 11/2010 | Chase |
| 7,837,595 B2 | 11/2010 | Rice |
| 7,839,058 B1 | 11/2010 | Churchill et al. |
| 7,846,070 B2 * | 12/2010 | Oglesby | A63B 22/0023 482/51 |
| 7,854,669 B2 | 12/2010 | Marty et al. |
| 7,862,483 B2 | 1/2011 | Hendrickson et al. |
| 7,871,355 B2 | 1/2011 | Yeh |
| 7,871,357 B2 | 1/2011 | Gibson et al. |
| 7,878,950 B1 | 2/2011 | Bastian |
| 7,883,448 B2 | 2/2011 | Wang |
| 7,887,465 B2 | 2/2011 | Uffelman |
| 7,892,148 B1 | 2/2011 | Stauffer et al. |
| 7,892,149 B2 | 2/2011 | Wu |
| 7,892,150 B1 | 2/2011 | Colley |
| 7,901,325 B2 | 3/2011 | Henderson |
| 7,908,981 B2 | 3/2011 | Agee |
| 7,914,420 B2 | 3/2011 | Daly et al. |
| 7,914,421 B2 | 3/2011 | Weier et al. |
| 7,919,950 B2 | 4/2011 | Uno et al. |
| 7,922,635 B2 | 4/2011 | Lull et al. |
| 7,927,253 B2 | 4/2011 | Vincent |
| 7,931,563 B2 | 4/2011 | Shaw et al. |
| 7,938,751 B2 | 5/2011 | Nicolas et al. |
| 7,938,755 B1 | 5/2011 | Dyer et al. |
| 7,942,783 B2 | 5/2011 | Ochi |
| 7,942,788 B2 | 5/2011 | Wu |
| 7,946,968 B2 | 5/2011 | Kjellberg |
| 7,949,295 B2 | 5/2011 | Kumar et al. |
| 7,951,046 B1 | 5/2011 | Barber, Jr. |
| 7,959,124 B2 | 6/2011 | Phifer et al. |
| 7,972,249 B1 | 7/2011 | Napalan |
| 7,976,437 B1 | 7/2011 | Von Detten |
| 7,978,081 B2 | 7/2011 | Shears et al. |
| 7,980,996 B2 | 7/2011 | Hickman |
| 7,985,164 B2 * | 7/2011 | Ashby | A63B 22/02 434/247 |
| 7,988,600 B2 | 8/2011 | Rodgers, Jr. |
| 8,001,472 B2 | 8/2011 | Gilley et al. |
| 8,002,674 B2 | 8/2011 | Piaget et al. |
| 8,002,684 B2 | 8/2011 | Laurent |
| 8,007,409 B2 | 8/2011 | Ellis |
| 8,012,067 B2 | 9/2011 | Joannou |
| 8,012,068 B1 | 9/2011 | Malcolm |
| 8,029,415 B2 * | 10/2011 | Ashby | G06F 19/3481 482/49 |
| 8,043,173 B2 | 10/2011 | Menalagha et al. |
| 8,047,965 B2 | 11/2011 | Shea |
| 8,047,966 B2 | 11/2011 | Dorogusker et al. |
| 8,047,970 B2 | 11/2011 | Nalley |
| 8,055,469 B2 | 11/2011 | Kulach et al. |
| 8,057,368 B1 | 11/2011 | Lyszczarz |
| 8,062,196 B1 | 11/2011 | Khubani |
| 8,066,514 B2 | 11/2011 | Clarke |
| 8,079,939 B1 | 12/2011 | Wang |
| 8,082,029 B2 | 12/2011 | Honda |
| 8,083,693 B1 | 12/2011 | McKeon et al. |
| 8,103,379 B2 | 1/2012 | Biba et al. |
| 8,104,411 B2 | 1/2012 | Fenton |
| 8,105,213 B2 | 1/2012 | Stewart et al. |
| 8,109,858 B2 | 2/2012 | Redmann |
| 8,113,994 B2 | 2/2012 | Piaget et al. |
| 8,123,527 B2 | 2/2012 | Holljes |
| 8,141,276 B2 | 3/2012 | Ellis |
| 8,147,385 B2 | 4/2012 | Crawford et al. |
| 8,162,804 B2 | 4/2012 | Tagliabue |
| 8,172,729 B2 | 5/2012 | Ellis |
| 8,177,688 B2 | 5/2012 | Burnfield et al. |
| 8,182,399 B2 | 5/2012 | Davis et al. |
| 8,188,700 B2 | 5/2012 | Tseng et al. |
| 8,221,290 B2 | 7/2012 | Vincent et al. |
| 8,221,295 B2 | 7/2012 | Wilkins |
| 8,240,430 B2 | 8/2012 | Downey |
| 8,241,187 B2 | 8/2012 | Moon et al. |
| 8,251,874 B2 | 8/2012 | Ashby et al. |
| 8,260,858 B2 | 9/2012 | Belz et al. |
| 8,272,996 B2 | 9/2012 | Weier |
| 8,275,265 B2 | 9/2012 | Kobyakov et al. |
| 8,280,259 B2 | 10/2012 | George et al. |
| 8,306,635 B2 | 11/2012 | Pryor |
| 8,315,823 B2 | 11/2012 | Berme et al. |
| 8,320,578 B2 | 11/2012 | Kahn et al. |
| 8,323,157 B2 | 12/2012 | Campanaro et al. |
| 8,333,681 B2 | 12/2012 | Schmidt |
| 8,343,016 B1 | 1/2013 | Astilean |
| 8,360,904 B2 | 1/2013 | Oleson et al. |
| 8,360,935 B2 | 1/2013 | Olsen et al. |
| 8,360,936 B2 | 1/2013 | Dibenedetto et al. |
| 8,368,329 B1 | 2/2013 | Depew et al. |
| 8,378,647 B2 | 2/2013 | Yonezawa et al. |
| 8,394,005 B2 | 3/2013 | Solow et al. |
| 8,395,366 B2 | 3/2013 | Uno |
| 8,435,160 B1 | 5/2013 | Clum |
| 8,446,275 B2 | 5/2013 | Utter, II |
| 8,449,620 B2 | 5/2013 | Hakansson et al. |
| 8,454,437 B2 | 6/2013 | Dugan |
| 8,459,479 B2 | 6/2013 | Yourist |
| 8,475,346 B2 | 7/2013 | Gerschefske et al. |
| 8,475,367 B1 | 7/2013 | Yuen et al. |
| 8,480,541 B1 | 7/2013 | Brunts |
| 8,485,944 B2 | 7/2013 | Drazan |
| 8,485,945 B2 | 7/2013 | Leonhard |
| 8,487,759 B2 | 7/2013 | Hill |
| 8,505,597 B2 | 8/2013 | Sharperson |
| 8,506,370 B2 | 8/2013 | Homsi |
| 8,512,210 B2 | 8/2013 | Shauli |
| 8,516,723 B2 | 8/2013 | Ferrigan et al. |
| 8,535,247 B2 | 9/2013 | Williams |
| 8,540,560 B2 | 9/2013 | Crowley et al. |
| 8,550,962 B2 | 10/2013 | Piaget et al. |
| 8,562,489 B2 | 10/2013 | Burton et al. |
| 8,573,982 B1 | 11/2013 | Chuang |
| 8,602,951 B2 | 12/2013 | Morris |
| 8,608,624 B2 | 12/2013 | Shabodyash et al. |
| 8,614,595 B2 | 12/2013 | Acatrinei |
| 8,614,902 B2 | 12/2013 | Pansier et al. |
| 8,617,008 B2 | 12/2013 | Marty et al. |
| 8,655,004 B2 | 2/2014 | Prest et al. |
| 8,657,724 B2 | 2/2014 | Yang |
| 8,690,578 B1 | 4/2014 | Nusbaum et al. |
| 8,690,735 B2 | 4/2014 | Watterson et al. |
| 8,690,738 B1 | 4/2014 | Astilian |
| 8,701,567 B1 | 4/2014 | Esfandiari et al. |
| 8,702,430 B2 | 4/2014 | Dibenedetto et al. |
| 8,702,567 B2 | 4/2014 | Hu |

(56) References Cited

U.S. PATENT DOCUMENTS

| | | |
|---|---|---|
| 8,708,870 B2 | 4/2014 | Nalley |
| 8,734,157 B1 | 5/2014 | Hummel, III |
| 8,734,301 B2 | 5/2014 | Remelius |
| 8,734,302 B2 | 5/2014 | Hsieh |
| 8,740,756 B2 | 6/2014 | Shabodyash et al. |
| 8,749,380 B2 | 6/2014 | Vock et al. |
| 8,758,201 B2 | 6/2014 | Ashby et al. |
| 8,762,101 B2 | 6/2014 | Yuen et al. |
| 8,764,609 B1 | 7/2014 | Elahmadie |
| 8,777,820 B2 | 7/2014 | Lo |
| 8,783,326 B1 | 7/2014 | Vaninger et al. |
| 8,784,274 B1 | 7/2014 | Chuang |
| 8,790,222 B2 | 7/2014 | Burger |
| 8,801,581 B2 | 8/2014 | Lai et al. |
| 8,824,697 B2 | 9/2014 | Christoph |
| 8,825,445 B2 | 9/2014 | Hoffman et al. |
| 8,847,988 B2 | 9/2014 | Geisner et al. |
| 8,851,565 B2 | 10/2014 | Hontz et al. |
| 8,864,627 B2 | 10/2014 | Bayerlein et al. |
| 8,876,661 B2 | 11/2014 | Lu |
| 8,888,660 B1 | 11/2014 | Oteman |
| 8,894,551 B2 | 11/2014 | Kerdjoudj |
| 8,920,291 B2 | 12/2014 | Chen et al. |
| 8,926,475 B2 | 1/2015 | Lin et al. |
| 8,926,479 B2 | 1/2015 | Chen et al. |
| 8,956,290 B2 | 2/2015 | Gilley et al. |
| 8,956,715 B2 | 2/2015 | Kim |
| 8,968,163 B1 | 3/2015 | Vidmar |
| 8,979,709 B2 | 3/2015 | Toback et al. |
| 8,986,165 B2 | 3/2015 | Ashby |
| 9,005,085 B2 | 4/2015 | Astilean |
| 9,011,291 B2 | 4/2015 | Birrell |
| 9,015,952 B2 | 4/2015 | Magosaki |
| 9,028,368 B2 | 5/2015 | Ashby et al. |
| 9,038,218 B1 | 5/2015 | Heil et al. |
| 9,039,578 B2 | 5/2015 | Dalebout |
| 9,050,491 B2 | 6/2015 | Gordon et al. |
| 9,050,498 B2 | 6/2015 | Lu et al. |
| 9,072,932 B2 | 7/2015 | Piaget et al. |
| 9,089,732 B2 | 7/2015 | Andon et al. |
| 9,095,740 B2 | 8/2015 | Wu |
| 9,108,079 B2 | 8/2015 | Solow et al. |
| 9,114,275 B2 | 8/2015 | Lu et al. |
| 9,114,276 B2 | 8/2015 | Bayerlein et al. |
| 9,119,983 B2 | 9/2015 | Rhea |
| 9,132,051 B2 | 9/2015 | Heil |
| 9,138,614 B2 | 9/2015 | Lu et al. |
| 9,138,615 B2 | 9/2015 | Olson et al. |
| 9,144,703 B2 | 9/2015 | Dalebout et al. |
| 9,162,102 B1 | 10/2015 | Eder et al. |
| 9,162,106 B1 | 10/2015 | Scheiman |
| 9,168,414 B2 | 10/2015 | Liu et al. |
| 9,174,085 B2 | 11/2015 | Foley |
| 9,186,537 B2 | 11/2015 | Arnold et al. |
| 9,186,549 B2 | 11/2015 | Watterson et al. |
| 9,186,552 B1 | 11/2015 | Deal |
| 9,192,800 B1 | 11/2015 | Meyer et al. |
| 9,199,115 B2 | 12/2015 | Yim et al. |
| 9,199,123 B2 | 12/2015 | Solow |
| 9,201,458 B2 | 12/2015 | Hunt et al. |
| 9,220,940 B2 | 12/2015 | Al Kuwari |
| 9,221,545 B2 | 12/2015 | Popescu et al. |
| 9,224,291 B2 | 12/2015 | Moll-Carrillo et al. |
| 9,226,692 B2 | 1/2016 | Haas |
| 9,289,063 B2 | 3/2016 | Baugh et al. |
| 9,308,415 B2 | 4/2016 | Crawford et al. |
| 9,311,802 B1 | 4/2016 | Chin et al. |
| 9,333,388 B2 | 5/2016 | Lee et al. |
| 9,339,681 B1 | 5/2016 | Nalley |
| 9,339,683 B2 | 5/2016 | Dilli et al. |
| 9,352,185 B2 | 5/2016 | Hendrickson et al. |
| 9,352,186 B2 | 5/2016 | Watterson |
| 9,352,187 B2 | 5/2016 | Piaget et al. |
| 9,357,551 B2 | 5/2016 | Gutman |
| 9,358,422 B2 | 6/2016 | Brontman |
| 9,364,706 B2 | 6/2016 | Lo |
| 9,364,708 B2 | 6/2016 | Luger et al. |
| 9,364,714 B2 | 6/2016 | Koduri et al. |
| 9,367,668 B2 * | 6/2016 | Flynt .................. G06F 19/3481 |
| 9,370,687 B2 | 6/2016 | Hao |
| 9,387,387 B2 | 7/2016 | Dalebout |
| 9,389,718 B1 | 7/2016 | Letourneur |
| 9,409,050 B2 | 8/2016 | Mintz |
| 9,415,257 B2 | 8/2016 | Habing |
| 9,452,315 B1 | 9/2016 | Murray et al. |
| 9,452,320 B2 | 9/2016 | Yang |
| 9,455,784 B2 | 9/2016 | Cune et al. |
| 9,457,224 B2 | 10/2016 | Giannelli et al. |
| 9,463,349 B1 | 10/2016 | Chang |
| 9,480,874 B2 | 11/2016 | Cutler |
| 9,486,658 B2 | 11/2016 | Alexander |
| 9,498,671 B1 | 11/2016 | Softky |
| 9,505,241 B2 | 11/2016 | Lyon |
| 9,539,458 B1 | 1/2017 | Ross |
| 9,540,071 B2 | 1/2017 | Jordan et al. |
| 9,540,174 B2 | 1/2017 | Josserond et al. |
| 9,560,917 B2 | 2/2017 | Roslund, Jr. |
| 9,573,017 B2 | 2/2017 | Chang |
| 9,579,534 B2 | 2/2017 | Sutkowski et al. |
| 9,579,544 B2 | 2/2017 | Watterson |
| 9,582,976 B2 | 2/2017 | Chin et al. |
| 9,604,099 B2 | 3/2017 | Taylor |
| 9,610,475 B1 | 4/2017 | DeKnock et al. |
| 9,623,286 B1 | 4/2017 | Chen |
| 9,673,904 B2 | 6/2017 | Palanisamy et al. |
| 9,681,313 B2 | 6/2017 | Malach |
| 9,682,306 B2 * | 6/2017 | Lin .................... A63B 71/0619 |
| 9,694,234 B2 | 7/2017 | Dalebout et al. |
| 9,700,780 B2 * | 7/2017 | Riley .................... A63B 71/06 |
| 9,707,441 B2 | 7/2017 | Yang |
| 9,707,447 B1 | 7/2017 | Lopez Babodilla |
| 9,731,158 B1 | 8/2017 | Lo |
| 9,737,747 B1 | 8/2017 | Walsh et al. |
| 9,757,605 B2 | 9/2017 | Olson et al. |
| 9,764,184 B2 | 9/2017 | Kueker et al. |
| 9,776,039 B1 | 10/2017 | Xu |
| 9,795,827 B2 | 10/2017 | Wiener et al. |
| 9,814,927 B2 | 11/2017 | Forystek |
| 9,814,929 B2 | 11/2017 | Moser |
| 9,814,930 B2 | 11/2017 | Manzke et al. |
| 9,827,458 B2 | 11/2017 | Dalton |
| 9,829,068 B2 | 11/2017 | Marchetti |
| 9,833,658 B2 | 12/2017 | Wiener et al. |
| 9,849,330 B2 | 12/2017 | Lagree |
| 9,889,334 B2 | 2/2018 | Ashby et al. |
| 9,901,767 B2 | 2/2018 | Kuo |
| 9,901,780 B2 * | 2/2018 | DeLuca ............ A63B 24/0087 |
| 9,901,805 B2 | 2/2018 | Hughes, Jr. |
| 9,914,011 B2 | 3/2018 | Downey et al. |
| 9,914,014 B2 | 3/2018 | Lagree et al. |
| 9,937,375 B2 | 4/2018 | Zhu |
| 9,943,719 B2 | 4/2018 | Smith et al. |
| 9,948,349 B2 | 4/2018 | Malach |
| 9,950,209 B2 | 4/2018 | Yim et al. |
| 9,956,450 B2 | 5/2018 | Bayerlein et al. |
| 9,968,821 B2 | 5/2018 | Finlayson et al. |
| 9,968,823 B2 | 5/2018 | Cutler |
| 9,987,513 B2 | 6/2018 | Yim et al. |
| 9,987,517 B1 | 6/2018 | Kuo |
| 9,993,680 B2 | 6/2018 | Gordon |
| 10,004,940 B2 | 6/2018 | Badarneh |
| 10,022,590 B2 | 7/2018 | Foley et al. |
| 2001/0001303 A1 | 5/2001 | Ohsuga et al. |
| 2001/0008053 A1 | 7/2001 | Belli |
| 2001/0024998 A1 | 9/2001 | Novak |
| 2001/0049470 A1 | 12/2001 | Mault et al. |
| 2001/0051564 A1 | 12/2001 | Iund |
| 2002/0016235 A1 | 2/2002 | Ashby et al. |
| 2002/0019298 A1 | 2/2002 | Eschenbach |
| 2002/0024521 A1 | 2/2002 | Goden |
| 2002/0025888 A1 | 2/2002 | Germanton |
| 2002/0026130 A1 | 2/2002 | West |
| 2002/0039952 A1 | 4/2002 | Clem |
| 2002/0043909 A1 | 4/2002 | Nielsen |

(56) References Cited

U.S. PATENT DOCUMENTS

| | | |
|---|---|---|
| 2002/0045519 A1 | 4/2002 | Watterson |
| 2002/0055418 A1 | 5/2002 | Pyles et al. |
| 2002/0055419 A1 | 5/2002 | Hinnebusch |
| 2002/0055420 A1 | 5/2002 | Stearns et al. |
| 2002/0055422 A1 | 5/2002 | Airmet |
| 2002/0066735 A1 | 6/2002 | Hewlitt et al. |
| 2002/0077221 A1 | 6/2002 | Dalebout et al. |
| 2002/0094914 A1 | 7/2002 | Maresh et al. |
| 2002/0107058 A1 | 8/2002 | Namba et al. |
| 2002/0115536 A1 | 8/2002 | Hojo |
| 2002/0128127 A1 | 9/2002 | Chen |
| 2002/0142890 A1 | 10/2002 | Ohrt |
| 2002/0147078 A1 | 10/2002 | Wu |
| 2002/0151413 A1 | 10/2002 | Dalebout |
| 2002/0160883 A1 | 10/2002 | Dugan |
| 2002/0171070 A1 | 11/2002 | Shim |
| 2002/0198084 A1 | 12/2002 | Stearns et al. |
| 2003/0032524 A1 | 2/2003 | Lamar et al. |
| 2003/0032535 A1 | 2/2003 | Wang |
| 2003/0045406 A1 | 3/2003 | Stone |
| 2003/0060331 A1 | 3/2003 | Polk |
| 2003/0060344 A1 | 3/2003 | David |
| 2003/0069108 A1 | 4/2003 | Rubinstein |
| 2003/0073545 A1 | 4/2003 | Liu |
| 2003/0078138 A1 | 4/2003 | Toyama |
| 2003/0092532 A1 | 5/2003 | Giannelli et al. |
| 2003/0092540 A1 | 5/2003 | Gillen |
| 2003/0092542 A1 | 5/2003 | Bartholomew et al. |
| 2003/0096675 A1 | 5/2003 | Wang |
| 2003/0097878 A1 | 5/2003 | Farringdon et al. |
| 2003/0104908 A1 | 6/2003 | Tung |
| 2003/0119635 A1 | 6/2003 | Arbuckle |
| 2003/0125165 A1 | 7/2003 | Trevino |
| 2003/0128186 A1 | 7/2003 | Laker |
| 2003/0134714 A1 | 7/2003 | Oishi et al. |
| 2003/0134718 A1 | 7/2003 | Kim |
| 2003/0148853 A1 | 8/2003 | Alessandri |
| 2003/0153434 A1 | 8/2003 | Dalebout |
| 2003/0171190 A1 | 9/2003 | Rice |
| 2003/0176815 A1 | 9/2003 | Baba et al. |
| 2003/0181289 A1 | 9/2003 | Oscar Moavro |
| 2003/0181293 A1 | 9/2003 | Baatz |
| 2003/0183027 A1 | 10/2003 | Koch |
| 2003/0211916 A1 | 11/2003 | Capuano |
| 2003/0222419 A1 | 12/2003 | Geary |
| 2003/0232707 A1 | 12/2003 | Dalebout et al. |
| 2003/0236153 A1 | 12/2003 | Pan et al. |
| 2004/0005958 A1 | 1/2004 | Kamen et al. |
| 2004/0005961 A1 | 1/2004 | Iund |
| 2004/0014567 A1 | 1/2004 | Mendel |
| 2004/0014571 A1 | 1/2004 | Haynes |
| 2004/0018915 A1 | 1/2004 | Reyes |
| 2004/0018917 A1 | 1/2004 | Corbalis |
| 2004/0018918 A1 | 1/2004 | Reyes |
| 2004/0023759 A1 | 2/2004 | Duncan et al. |
| 2004/0023761 A1 | 2/2004 | Emery |
| 2004/0023762 A1 | 2/2004 | Lull |
| 2004/0023766 A1 | 2/2004 | Slone |
| 2004/0023778 A1 | 2/2004 | Kusumoto et al. |
| 2004/0025754 A1 | 2/2004 | Dye |
| 2004/0029645 A1 | 2/2004 | Chen |
| 2004/0033865 A1 | 2/2004 | Wu |
| 2004/0043873 A1 | 3/2004 | Wilkinson et al. |
| 2004/0051392 A1 | 3/2004 | Badarneh |
| 2004/0053748 A1 | 3/2004 | Lo et al. |
| 2004/0063549 A1 | 4/2004 | Kuo |
| 2004/0067821 A1 | 4/2004 | Kehrbaum |
| 2004/0067833 A1 | 4/2004 | Talish |
| 2004/0082444 A1 | 4/2004 | Golesh |
| 2004/0092367 A1 | 5/2004 | Corbalis |
| 2004/0097331 A1 | 5/2004 | Zillig |
| 2004/0100484 A1 | 5/2004 | Barrett |
| 2004/0102292 A1 | 5/2004 | Pyles et al. |
| 2004/0103432 A1 | 5/2004 | Barrett |
| 2004/0114768 A1 | 6/2004 | Luo |
| 2004/0127335 A1 | 7/2004 | Watterson |
| 2004/0132586 A1 | 7/2004 | Leighton et al. |
| 2004/0132587 A1 | 7/2004 | Leighton et al. |
| 2004/0136750 A1 | 7/2004 | Yoshioka et al. |
| 2004/0138030 A1 | 7/2004 | Wang |
| 2004/0142800 A1 | 7/2004 | Gerschefske |
| 2004/0144626 A1 | 7/2004 | Saeki |
| 2004/0152566 A1 | 8/2004 | Yeh |
| 2004/0155622 A1 | 8/2004 | Mayhew et al. |
| 2004/0160336 A1 | 8/2004 | Hoch |
| 2004/0162189 A1 | 8/2004 | Hickman |
| 2004/0162191 A1 | 8/2004 | Ercanbrack |
| 2004/0163574 A1 | 8/2004 | Schoenbach |
| 2004/0166999 A1 | 8/2004 | Dodge |
| 2004/0171460 A1 | 9/2004 | Park |
| 2004/0171464 A1 | 9/2004 | Ashby et al. |
| 2004/0171465 A1 | 9/2004 | Hald |
| 2004/0176215 A1 | 9/2004 | Gramaccioni |
| 2004/0176217 A1 | 9/2004 | Watterson |
| 2004/0177531 A1 | 9/2004 | Dibenedetto et al. |
| 2004/0180719 A1 | 9/2004 | Feldman |
| 2004/0181972 A1 | 9/2004 | Csorba |
| 2004/0192514 A1 | 9/2004 | Piaget et al. |
| 2004/0198555 A1 | 10/2004 | Anderson |
| 2004/0198559 A1 | 10/2004 | Grossi |
| 2004/0198571 A1 | 10/2004 | Howell et al. |
| 2004/0214693 A1 | 10/2004 | Piaget et al. |
| 2004/0224740 A1 | 11/2004 | Ball et al. |
| 2004/0224825 A1 | 11/2004 | Giannelli et al. |
| 2004/0224827 A1 | 11/2004 | Ashley |
| 2004/0242378 A1 | 12/2004 | Pan |
| 2004/0242379 A1 | 12/2004 | Juva |
| 2004/0242380 A1 | 12/2004 | Kuivala |
| 2004/0248699 A1 | 12/2004 | Colley |
| 2004/0254020 A1 | 12/2004 | Dragusin |
| 2004/0256524 A1 | 12/2004 | Beck et al. |
| 2004/0259689 A1 | 12/2004 | Wilkins et al. |
| 2004/0266587 A1 | 12/2004 | Miller |
| 2005/0003931 A1 | 1/2005 | Mills et al. |
| 2005/0003933 A1 | 1/2005 | Kau |
| 2005/0008992 A1 | 1/2005 | Westergaard et al. |
| 2005/0009668 A1 | 1/2005 | Savettiere |
| 2005/0023292 A1 | 2/2005 | Market et al. |
| 2005/0032610 A1 | 2/2005 | Nelson |
| 2005/0032611 A1 | 2/2005 | Webber |
| 2005/0037898 A1 | 2/2005 | Chang |
| 2005/0037904 A1 | 2/2005 | Chang |
| 2005/0043145 A1 | 2/2005 | Anderson et al. |
| 2005/0043146 A1 | 2/2005 | Lo et al. |
| 2005/0043155 A1 | 2/2005 | Yannitte |
| 2005/0049117 A1 | 3/2005 | Rodgers |
| 2005/0049121 A1 | 3/2005 | Dalebout |
| 2005/0054492 A1 | 3/2005 | Neff |
| 2005/0064994 A1 | 3/2005 | Matsumoto |
| 2005/0075213 A1 | 4/2005 | Arick |
| 2005/0090770 A1 | 4/2005 | Chen |
| 2005/0096187 A1 | 5/2005 | Hsu |
| 2005/0096189 A1 | 5/2005 | Chen |
| 2005/0107220 A1 | 5/2005 | Wang |
| 2005/0107226 A1 | 5/2005 | Monda |
| 2005/0113158 A1 | 5/2005 | Sterchi et al. |
| 2005/0124471 A1 | 6/2005 | Wilkinson |
| 2005/0129903 A1 | 6/2005 | Carr |
| 2005/0130807 A1 | 6/2005 | Cutler |
| 2005/0131319 A1 | 6/2005 | Der Meer |
| 2005/0132838 A1 | 6/2005 | Lin |
| 2005/0143226 A1 | 6/2005 | Heidecke |
| 2005/0143228 A1 | 6/2005 | Lee |
| 2005/0148398 A1 | 7/2005 | Lochtefeld et al. |
| 2005/0148439 A1 | 7/2005 | Wu |
| 2005/0148440 A1 | 7/2005 | Denton |
| 2005/0148442 A1 | 7/2005 | Watterson |
| 2005/0148443 A1 | 7/2005 | Watterson |
| 2005/0159273 A1 | 7/2005 | Chen |
| 2005/0164838 A1 | 7/2005 | Watterson |
| 2005/0164839 A1 | 7/2005 | Watterson |
| 2005/0170935 A1 | 8/2005 | Manser |
| 2005/0170936 A1 | 8/2005 | Quinn |
| 2005/0178210 A1 | 8/2005 | Lanham |

(56) References Cited

U.S. PATENT DOCUMENTS

| | | |
|---|---|---|
| 2005/0181347 A1 | 8/2005 | Barnes et al. |
| 2005/0181911 A1 | 8/2005 | Porth |
| 2005/0192162 A1 | 9/2005 | Pan |
| 2005/0192163 A1 | 9/2005 | Pan et al. |
| 2005/0196737 A1 | 9/2005 | Mann |
| 2005/0202934 A1 | 9/2005 | Olrik et al. |
| 2005/0209052 A1 | 9/2005 | Ashby |
| 2005/0209056 A1 | 9/2005 | Daly |
| 2005/0209060 A1 | 9/2005 | Lull |
| 2005/0209061 A1 | 9/2005 | Crawford et al. |
| 2005/0209062 A1 | 9/2005 | Anderson et al. |
| 2005/0215397 A1 | 9/2005 | Watterson |
| 2005/0227820 A1 | 10/2005 | Dyer et al. |
| 2005/0233861 A1 | 10/2005 | Hickman |
| 2005/0233871 A1 | 10/2005 | Anders |
| 2005/0239600 A1 | 10/2005 | Liang |
| 2005/0239607 A1 | 10/2005 | Chang |
| 2005/0245370 A1 | 11/2005 | Boland |
| 2005/0250622 A1 | 11/2005 | Chang |
| 2005/0266961 A1 | 12/2005 | Shum et al. |
| 2005/0272562 A1 | 12/2005 | Alessandri et al. |
| 2005/0272577 A1 | 12/2005 | Olson |
| 2005/0277520 A1 | 12/2005 | Van Waes |
| 2005/0281963 A1 | 12/2005 | Cook |
| 2005/0283911 A1 | 12/2005 | Roussy |
| 2005/0288155 A1 | 12/2005 | Yang |
| 2006/0003869 A1 | 1/2006 | Huang et al. |
| 2006/0003872 A1 | 1/2006 | Chiles et al. |
| 2006/0009332 A1 | 1/2006 | Jones |
| 2006/0019804 A1 | 1/2006 | Young |
| 2006/0035755 A1 | 2/2006 | Dalebout |
| 2006/0035757 A1 | 2/2006 | Flick et al. |
| 2006/0035758 A1 | 2/2006 | Rogozinski |
| 2006/0040797 A1 | 2/2006 | Chang |
| 2006/0040798 A1 | 2/2006 | Weier et al. |
| 2006/0046905 A1 | 3/2006 | Doody, Jr. |
| 2006/0047447 A1 | 3/2006 | Brady et al. |
| 2006/0052220 A1 | 3/2006 | Jackson et al. |
| 2006/0053586 A1 | 3/2006 | Chase |
| 2006/0053587 A1 | 3/2006 | Chase |
| 2006/0058158 A1 | 3/2006 | McAvoy |
| 2006/0058162 A1 | 3/2006 | Vieno et al. |
| 2006/0063644 A1 | 3/2006 | Yang |
| 2006/0068978 A1 | 3/2006 | Moon |
| 2006/0075544 A1 | 4/2006 | Kriesel |
| 2006/0079800 A1 | 4/2006 | Martikka et al. |
| 2006/0100069 A1 | 5/2006 | Dibble et al. |
| 2006/0100546 A1 | 5/2006 | Silk |
| 2006/0122035 A1 | 6/2006 | Felix |
| 2006/0122038 A1 | 6/2006 | Chou Lin |
| 2006/0122044 A1 | 6/2006 | Ho |
| 2006/0123814 A1 | 6/2006 | Choi et al. |
| 2006/0128534 A1 | 6/2006 | Roque |
| 2006/0132070 A1 | 6/2006 | Heydt et al. |
| 2006/0135274 A1 | 6/2006 | Henry |
| 2006/0135322 A1 | 6/2006 | Rocker |
| 2006/0148622 A1 | 7/2006 | Chen |
| 2006/0151303 A1 | 7/2006 | Motoda |
| 2006/0160665 A1 | 7/2006 | Tai |
| 2006/0160666 A1 | 7/2006 | Wang |
| 2006/0166791 A1 | 7/2006 | Liao |
| 2006/0166799 A1 | 7/2006 | Boland et al. |
| 2006/0172862 A1 | 8/2006 | Badarneh et al. |
| 2006/0189439 A1 | 8/2006 | Baudhuin |
| 2006/0189440 A1 | 8/2006 | Gravagne |
| 2006/0189462 A1 | 8/2006 | Pearson et al. |
| 2006/0194679 A1 | 8/2006 | Hatcher |
| 2006/0199706 A1 | 9/2006 | Wehrell |
| 2006/0205568 A1 | 9/2006 | Huang |
| 2006/0205569 A1 | 9/2006 | Watterson |
| 2006/0205571 A1 | 9/2006 | Krull |
| 2006/0217236 A1 | 9/2006 | Watterson |
| 2006/0217245 A1 | 9/2006 | Golesh et al. |
| 2006/0223680 A1 | 10/2006 | Chang |
| 2006/0229163 A1 | 10/2006 | Waters |
| 2006/0229170 A1 | 10/2006 | Ozawa et al. |
| 2006/0232147 A1 | 10/2006 | Cheng |
| 2006/0234832 A1 | 10/2006 | Toyama et al. |
| 2006/0240947 A1 | 10/2006 | Qu |
| 2006/0240951 A1 | 10/2006 | Wang |
| 2006/0240959 A1 | 10/2006 | Huang |
| 2006/0244187 A1 | 11/2006 | Downey |
| 2006/0247109 A1 | 11/2006 | Powell |
| 2006/0248965 A1 | 11/2006 | Wyatt |
| 2006/0252602 A1 | 11/2006 | Brown |
| 2006/0252608 A1 | 11/2006 | Kang et al. |
| 2006/0258513 A1 | 11/2006 | Routley |
| 2006/0258515 A1 | 11/2006 | Kang et al. |
| 2006/0264306 A1 | 11/2006 | Tischler |
| 2006/0270522 A1 | 11/2006 | Yonehana et al. |
| 2006/0276306 A1 | 12/2006 | Pan et al. |
| 2006/0279294 A1 | 12/2006 | Cehelnik |
| 2006/0287089 A1 | 12/2006 | Addington et al. |
| 2006/0287147 A1 | 12/2006 | Kriesel |
| 2006/0287161 A1 | 12/2006 | Dalebout |
| 2006/0287163 A1 | 12/2006 | Wang |
| 2006/0288846 A1 | 12/2006 | Logan |
| 2007/0004561 A1 | 1/2007 | Yoo |
| 2007/0004562 A1 | 1/2007 | Pan et al. |
| 2007/0004569 A1 | 1/2007 | Cao |
| 2007/0006489 A1 | 1/2007 | Case et al. |
| 2007/0010383 A1 | 1/2007 | Pertegaz-Esteban |
| 2007/0015635 A1 | 1/2007 | Donner |
| 2007/0015636 A1 | 1/2007 | Molter |
| 2007/0027002 A1 | 2/2007 | Clark et al. |
| 2007/0027003 A1 | 2/2007 | Clark et al. |
| 2007/0032353 A1 | 2/2007 | Wilkins et al. |
| 2007/0037667 A1 | 2/2007 | Gordon |
| 2007/0038137 A1 | 2/2007 | Arand et al. |
| 2007/0042868 A1 | 2/2007 | Fisher |
| 2007/0049462 A1 | 3/2007 | Asukai et al. |
| 2007/0049464 A1 | 3/2007 | Chou |
| 2007/0049465 A1 | 3/2007 | Wu |
| 2007/0049466 A1 | 3/2007 | Hubbard |
| 2007/0049470 A1 | 3/2007 | Pyles et al. |
| 2007/0054790 A1 | 3/2007 | Dodge et al. |
| 2007/0060449 A1 | 3/2007 | Lo |
| 2007/0060450 A1 | 3/2007 | Lo |
| 2007/0060451 A1 | 3/2007 | Lucas |
| 2007/0066448 A1 | 3/2007 | Pan et al. |
| 2007/0072748 A1 | 3/2007 | Lee |
| 2007/0072752 A1 | 3/2007 | Koch |
| 2007/0079691 A1 | 4/2007 | Turner |
| 2007/0087908 A1 | 4/2007 | Pan et al. |
| 2007/0111858 A1 | 5/2007 | Dugan |
| 2007/0111866 A1 | 5/2007 | McVay et al. |
| 2007/0117683 A1 | 5/2007 | Ercanbrack et al. |
| 2007/0123389 A1 | 5/2007 | Martin |
| 2007/0123390 A1 | 5/2007 | Mathis |
| 2007/0123395 A1 | 5/2007 | Ellis |
| 2007/0123396 A1 | 5/2007 | Ellis |
| 2007/0131409 A1 | 6/2007 | Asahi |
| 2007/0135264 A1 | 6/2007 | Rosenberg |
| 2007/0137331 A1 | 6/2007 | Kachouh |
| 2007/0142177 A1 | 6/2007 | Simms et al. |
| 2007/0142179 A1 | 6/2007 | Terao et al. |
| 2007/0142183 A1 | 6/2007 | Chang |
| 2007/0142187 A1 | 6/2007 | Kolomeir |
| 2007/0149363 A1 | 6/2007 | Wang |
| 2007/0151489 A1 | 7/2007 | Byrne |
| 2007/0155277 A1 | 7/2007 | Amitai et al. |
| 2007/0155495 A1 | 7/2007 | Goo |
| 2007/0161466 A1 | 7/2007 | Oglesby et al. |
| 2007/0161468 A1 | 7/2007 | Yanagisawa et al. |
| 2007/0167292 A1 | 7/2007 | Kuo |
| 2007/0179023 A1 | 8/2007 | Dyer |
| 2007/0184953 A1 | 8/2007 | Luberski et al. |
| 2007/0190508 A1 | 8/2007 | Dalton |
| 2007/0191141 A1 | 8/2007 | Weber |
| 2007/0191190 A1 | 8/2007 | Kuo |
| 2007/0191197 A1 | 8/2007 | Vittone |
| 2007/0197345 A1 | 8/2007 | Wallace et al. |
| 2007/0197353 A1 | 8/2007 | Hundley |
| 2007/0197920 A1 | 8/2007 | Adams |

(56) References Cited

U.S. PATENT DOCUMENTS

| | | |
|---|---|---|
| 2007/0201727 A1 | 8/2007 | Birrell et al. |
| 2007/0204430 A1 | 9/2007 | Chase |
| 2007/0214630 A1 | 9/2007 | Kim |
| 2007/0219066 A1 | 9/2007 | Wang |
| 2007/0225119 A1 | 9/2007 | Schenk |
| 2007/0225120 A1 | 9/2007 | Schenk |
| 2007/0225126 A1 | 9/2007 | Yoo |
| 2007/0225127 A1 | 9/2007 | Pan et al. |
| 2007/0225622 A1 | 9/2007 | Huang et al. |
| 2007/0232455 A1 | 10/2007 | Hanoun |
| 2007/0232463 A1 | 10/2007 | Wu |
| 2007/0245612 A1 | 10/2007 | Tresenfeld |
| 2007/0247320 A1 | 10/2007 | Morahan |
| 2007/0249467 A1 | 10/2007 | Hong et al. |
| 2007/0270294 A1 | 11/2007 | Sheets |
| 2007/0270667 A1 | 11/2007 | Coppi et al. |
| 2007/0270726 A1 | 11/2007 | Chou |
| 2007/0281828 A1 | 12/2007 | Rice |
| 2007/0281831 A1 | 12/2007 | Wang |
| 2007/0284495 A1 | 12/2007 | Charles |
| 2007/0287601 A1 | 12/2007 | Burck et al. |
| 2007/0296313 A1 | 12/2007 | Wang |
| 2007/0298935 A1 | 12/2007 | Badarneh |
| 2007/0298937 A1 | 12/2007 | Shah |
| 2008/0001772 A1 | 1/2008 | Saito |
| 2008/0001866 A1 | 1/2008 | Martin |
| 2008/0004162 A1 | 1/2008 | Chen |
| 2008/0015094 A1 | 1/2008 | Casagrande |
| 2008/0018211 A1 | 1/2008 | Dye |
| 2008/0020898 A1 | 1/2008 | Pyles et al. |
| 2008/0020902 A1 | 1/2008 | Arnold |
| 2008/0020907 A1 | 1/2008 | Lin |
| 2008/0026658 A1 | 1/2008 | Kriesel |
| 2008/0026838 A1 | 1/2008 | Dunstan et al. |
| 2008/0032864 A1 | 2/2008 | Hakki |
| 2008/0032870 A1 | 2/2008 | Wu |
| 2008/0032871 A1 | 2/2008 | Yeh |
| 2008/0039301 A1 | 2/2008 | Halbridge |
| 2008/0046246 A1 | 2/2008 | Hakki |
| 2008/0057889 A1 | 3/2008 | Jan |
| 2008/0058169 A1 | 3/2008 | Fox |
| 2008/0058170 A1 | 3/2008 | Giannascoli et al. |
| 2008/0067302 A1 | 3/2008 | Olivera |
| 2008/0070756 A1 | 3/2008 | Chu |
| 2008/0076637 A1 | 3/2008 | Gilley et al. |
| 2008/0076972 A1 | 3/2008 | Dorogusker et al. |
| 2008/0077619 A1 | 3/2008 | Gilley et al. |
| 2008/0086318 A1 | 4/2008 | Gilley et al. |
| 2008/0096745 A1 | 4/2008 | Perry |
| 2008/0103024 A1 | 5/2008 | Habing |
| 2008/0103034 A1 | 5/2008 | Mihara et al. |
| 2008/0108917 A1 | 5/2008 | Joutras et al. |
| 2008/0119333 A1 | 5/2008 | Bowser |
| 2008/0132386 A1 | 6/2008 | Helie |
| 2008/0139370 A1 | 6/2008 | Charnitski |
| 2008/0153670 A1 | 6/2008 | Mckirdy |
| 2008/0153682 A1 | 6/2008 | Chen et al. |
| 2008/0155077 A1 | 6/2008 | James |
| 2008/0161170 A1 | 7/2008 | Lumpee |
| 2008/0161653 A1 | 7/2008 | Lin et al. |
| 2008/0171640 A1 | 7/2008 | Chang |
| 2008/0171922 A1 | 7/2008 | Teller |
| 2008/0176717 A1 | 7/2008 | Wang |
| 2008/0176718 A1 | 7/2008 | Wang |
| 2008/0182724 A1 | 7/2008 | Guthrie |
| 2008/0187689 A1 | 8/2008 | Dierkens et al. |
| 2008/0188362 A1 | 8/2008 | Chen |
| 2008/0190745 A1 | 8/2008 | Taniguchi et al. |
| 2008/0191864 A1 | 8/2008 | Wolfson |
| 2008/0200287 A1 | 8/2008 | Marty et al. |
| 2008/0200314 A1 | 8/2008 | Dalebout et al. |
| 2008/0207407 A1 | 8/2008 | Yeh |
| 2008/0214358 A1 | 9/2008 | Ogg et al. |
| 2008/0214971 A1 | 9/2008 | Talish |
| 2008/0216717 A1 | 9/2008 | Jones |
| 2008/0228110 A1 | 9/2008 | Berme |
| 2008/0229875 A1 | 9/2008 | Ray |
| 2008/0234110 A1 | 9/2008 | Webber et al. |
| 2008/0234111 A1 | 9/2008 | Packham |
| 2008/0242511 A1 | 10/2008 | Munoz et al. |
| 2008/0244870 A1 | 10/2008 | Chase |
| 2008/0245944 A1 | 10/2008 | Chase |
| 2008/0248926 A1 | 10/2008 | Cole et al. |
| 2008/0248935 A1 | 10/2008 | Solow |
| 2008/0250729 A1 | 10/2008 | Kriesel |
| 2008/0255794 A1 | 10/2008 | Levine |
| 2008/0269017 A1 | 10/2008 | Ungari |
| 2008/0279896 A1 | 11/2008 | Heinen et al. |
| 2008/0280732 A1 | 11/2008 | Jones |
| 2008/0280733 A1 | 11/2008 | Dickie et al. |
| 2008/0280734 A1 | 11/2008 | Dickie et al. |
| 2008/0280735 A1 | 11/2008 | Dickie et al. |
| 2008/0287262 A1 | 11/2008 | Chou |
| 2008/0300110 A1 | 12/2008 | Smith et al. |
| 2008/0300114 A1 | 12/2008 | Dalebout |
| 2008/0300115 A1 | 12/2008 | Erlandson |
| 2008/0300116 A1 | 12/2008 | Eder |
| 2008/0300914 A1 | 12/2008 | Karkanias et al. |
| 2008/0305936 A1 | 12/2008 | Cao |
| 2008/0312047 A1 | 12/2008 | Feng |
| 2008/0318737 A1 | 12/2008 | Chu |
| 2009/0001831 A1 | 1/2009 | Cho et al. |
| 2009/0005224 A1 | 1/2009 | Davis et al. |
| 2009/0011907 A1 | 1/2009 | Radow |
| 2009/0023553 A1 | 1/2009 | Shim |
| 2009/0023556 A1 | 1/2009 | Daly |
| 2009/0027925 A1 | 1/2009 | Kanouda et al. |
| 2009/0029831 A1 | 1/2009 | Weier |
| 2009/0036276 A1 | 2/2009 | Loach |
| 2009/0042696 A1 | 2/2009 | Wang |
| 2009/0042698 A1 | 2/2009 | Wang |
| 2009/0047645 A1 | 2/2009 | Dibenedetto et al. |
| 2009/0048044 A1 | 2/2009 | Oleson et al. |
| 2009/0048073 A1 | 2/2009 | Roimicher |
| 2009/0048079 A1 | 2/2009 | Nalley |
| 2009/0048493 A1 | 2/2009 | James et al. |
| 2009/0053682 A1 | 2/2009 | Stern |
| 2009/0054214 A1 | 2/2009 | Kadar |
| 2009/0054751 A1 | 2/2009 | Babashan et al. |
| 2009/0062072 A1 | 3/2009 | Packham |
| 2009/0069159 A1 | 3/2009 | Wang |
| 2009/0069722 A1 | 3/2009 | Flaction et al. |
| 2009/0075781 A1 | 3/2009 | Schwarzberg et al. |
| 2009/0075784 A1 | 3/2009 | Hoggan |
| 2009/0080808 A1 | 3/2009 | Hagen |
| 2009/0082176 A1 | 3/2009 | Watterson et al. |
| 2009/0088301 A1 | 4/2009 | Alling |
| 2009/0093347 A1 | 4/2009 | Wang |
| 2009/0100718 A1 | 4/2009 | Gerber |
| 2009/0105047 A1 | 4/2009 | Guidi et al. |
| 2009/0105052 A1 | 4/2009 | Dalebout et al. |
| 2009/0105548 A1 | 4/2009 | Bart |
| 2009/0111664 A1 | 4/2009 | Kau |
| 2009/0111665 A1 | 4/2009 | Wang |
| 2009/0111666 A1 | 4/2009 | Wang |
| 2009/0111670 A1 | 4/2009 | Williams |
| 2009/0118098 A1 | 5/2009 | Yeh |
| 2009/0118103 A1 | 5/2009 | Ellis |
| 2009/0119032 A1 | 5/2009 | Meyer |
| 2009/0120208 A1 | 5/2009 | Meyer |
| 2009/0120210 A1 | 5/2009 | Phillips et al. |
| 2009/0124463 A1 | 5/2009 | Lin |
| 2009/0124464 A1 | 5/2009 | Kastelic |
| 2009/0124465 A1 | 5/2009 | Wang |
| 2009/0124466 A1 | 5/2009 | Zhang |
| 2009/0128516 A1 | 5/2009 | Rimon et al. |
| 2009/0137367 A1 | 5/2009 | Hendrickson et al. |
| 2009/0144639 A1 | 6/2009 | Nims et al. |
| 2009/0156363 A1 | 6/2009 | Guidi et al. |
| 2009/0156364 A1 | 6/2009 | Simeoni |
| 2009/0158871 A1 | 6/2009 | Chuo |
| 2009/0163326 A1 | 6/2009 | Wang |
| 2009/0163327 A1 | 6/2009 | Huang et al. |
| 2009/0163334 A1 | 6/2009 | Gibson et al. |

(56) References Cited

U.S. PATENT DOCUMENTS

| | | |
|---|---|---|
| 2009/0170663 A1 | 7/2009 | Cox et al. |
| 2009/0170667 A1 | 7/2009 | Irving et al. |
| 2009/0170672 A1 | 7/2009 | Mcmullen |
| 2009/0176625 A1 | 7/2009 | Giannelli et al. |
| 2009/0176628 A1 | 7/2009 | Radding et al. |
| 2009/0180646 A1 | 7/2009 | Vulfson et al. |
| 2009/0181829 A1 | 7/2009 | Wu |
| 2009/0181830 A1 | 7/2009 | Wu |
| 2009/0181831 A1 | 7/2009 | Kuo |
| 2009/0181833 A1 | 7/2009 | Cassidy |
| 2009/0197740 A1 | 8/2009 | Julskjaer et al. |
| 2009/0209393 A1 | 8/2009 | Crater et al. |
| 2009/0221405 A1 | 9/2009 | Wang |
| 2009/0221407 A1 | 9/2009 | Hauk |
| 2009/0227424 A1 | 9/2009 | Hirata et al. |
| 2009/0227432 A1 | 9/2009 | Pacheco |
| 2009/0232420 A1 | 9/2009 | Eisenberg et al. |
| 2009/0240858 A1 | 9/2009 | Takebayashi |
| 2009/0246746 A1 | 10/2009 | Roerdink et al. |
| 2009/0253554 A1 | 10/2009 | Mcintosh |
| 2009/0258710 A1 | 10/2009 | Quatrochi et al. |
| 2009/0258763 A1 | 10/2009 | Richter |
| 2009/0264258 A1 | 10/2009 | Lo |
| 2009/0264260 A1 | 10/2009 | Piaget et al. |
| 2009/0269728 A1 | 10/2009 | Verstegen et al. |
| 2009/0280964 A1 | 11/2009 | Lin |
| 2009/0286653 A1 | 11/2009 | Wiber |
| 2009/0293319 A1 | 12/2009 | Avni |
| 2009/0312158 A1 | 12/2009 | Trevino et al. |
| 2010/0015585 A1 | 1/2010 | Baker |
| 2010/0016127 A1 | 1/2010 | Farnsworth et al. |
| 2010/0022354 A1 | 1/2010 | Fisher |
| 2010/0024590 A1 | 2/2010 | O'neill |
| 2010/0032533 A1 | 2/2010 | Chen et al. |
| 2010/0034665 A1 | 2/2010 | Zhong et al. |
| 2010/0035726 A1 | 2/2010 | Fisher et al. |
| 2010/0041516 A1 | 2/2010 | Zhong et al. |
| 2010/0062904 A1 | 3/2010 | Crawford et al. |
| 2010/0062914 A1 | 3/2010 | Splane |
| 2010/0063426 A1 | 3/2010 | Planke |
| 2010/0064255 A1 | 3/2010 | Rottler et al. |
| 2010/0069202 A1 | 3/2010 | Olsen |
| 2010/0075812 A1 | 3/2010 | Piaget et al. |
| 2010/0079291 A1 | 4/2010 | Kroll et al. |
| 2010/0081548 A1 | 4/2010 | Labedz |
| 2010/0087298 A1 | 4/2010 | Zaccherini |
| 2010/0093492 A1 | 4/2010 | Watterson et al. |
| 2010/0099541 A1 | 4/2010 | Patel |
| 2010/0105527 A1 | 4/2010 | Johnson |
| 2010/0113223 A1 | 5/2010 | Chiles et al. |
| 2010/0125026 A1 | 5/2010 | Zavadsky et al. |
| 2010/0130337 A1 | 5/2010 | Stewart |
| 2010/0137105 A1 | 6/2010 | McLaughlin |
| 2010/0144501 A1 | 6/2010 | Berhanu |
| 2010/0156625 A1 | 6/2010 | Ruha |
| 2010/0164579 A1 | 7/2010 | Acatrinei |
| 2010/0167883 A1 | 7/2010 | Grind |
| 2010/0173276 A1 | 7/2010 | Vasin |
| 2010/0173755 A1 | 7/2010 | P Erez De Lazarraga |
| 2010/0175634 A1 | 7/2010 | Chang et al. |
| 2010/0184568 A1 | 7/2010 | Schippers |
| 2010/0190615 A1 | 7/2010 | Baker et al. |
| 2010/0192715 A1 | 8/2010 | Vauchel et al. |
| 2010/0197462 A1 | 8/2010 | Piane, Jr. |
| 2010/0197465 A1 | 8/2010 | Stevenson |
| 2010/0210418 A1 | 8/2010 | Park |
| 2010/0216599 A1 | 8/2010 | Watterson |
| 2010/0216600 A1 | 8/2010 | Noffsinger |
| 2010/0216607 A1 | 8/2010 | Mueller |
| 2010/0222179 A1 | 9/2010 | Temple et al. |
| 2010/0222182 A1 | 9/2010 | Park |
| 2010/0227740 A1 | 9/2010 | Liu |
| 2010/0234185 A1 | 9/2010 | Watt et al. |
| 2010/0235667 A1 | 9/2010 | Mucignat et al. |
| 2010/0240458 A1 | 9/2010 | Gaiba et al. |
| 2010/0248899 A1 | 9/2010 | Bedell et al. |
| 2010/0248900 A1 | 9/2010 | Ashby |
| 2010/0255959 A1 | 10/2010 | Dalebout et al. |
| 2010/0267524 A1 | 10/2010 | Stewart et al. |
| 2010/0285933 A1 | 11/2010 | Nalley |
| 2010/0289466 A1 | 11/2010 | Telefus |
| 2010/0289772 A1 | 11/2010 | Miller |
| 2010/0292050 A1 | 11/2010 | DiBenedetto et al. |
| 2010/0292600 A1 | 11/2010 | Dibenedetto et al. |
| 2010/0304931 A1 | 12/2010 | Stumpf |
| 2010/0304932 A1 | 12/2010 | Kolman et al. |
| 2010/0311552 A1 | 12/2010 | Sumners |
| 2010/0320956 A1 | 12/2010 | Lumsden et al. |
| 2011/0003664 A1 | 1/2011 | Richard |
| 2011/0009249 A1 | 1/2011 | Campanaro et al. |
| 2011/0021319 A1 | 1/2011 | Nissila et al. |
| 2011/0021323 A1 | 1/2011 | Wu |
| 2011/0028282 A1 | 2/2011 | Sbragia |
| 2011/0034300 A1 | 2/2011 | Hall |
| 2011/0054359 A1 | 3/2011 | Sazonov et al. |
| 2011/0056328 A1 | 3/2011 | Ko |
| 2011/0061840 A1 | 3/2011 | Goldmann |
| 2011/0065371 A1 | 3/2011 | Leff |
| 2011/0065373 A1 | 3/2011 | Goldmann |
| 2011/0067361 A1 | 3/2011 | Sloan |
| 2011/0073743 A1 | 3/2011 | Shamie |
| 2011/0075835 A1 | 3/2011 | Hill |
| 2011/0077055 A1 | 3/2011 | Pakula et al. |
| 2011/0082011 A1 | 4/2011 | Ellis |
| 2011/0082013 A1 | 4/2011 | Bastian |
| 2011/0086707 A1 | 4/2011 | Loveland |
| 2011/0087445 A1 | 4/2011 | Sobolewski |
| 2011/0087446 A1 | 4/2011 | Redmond |
| 2011/0093100 A1 | 4/2011 | Ramsay |
| 2011/0098157 A1 | 4/2011 | Whalen et al. |
| 2011/0098615 A1 | 4/2011 | Whalen et al. |
| 2011/0109283 A1 | 5/2011 | Kapels et al. |
| 2011/0112771 A1 | 5/2011 | French |
| 2011/0118089 A1 | 5/2011 | Ellis |
| 2011/0118090 A1 | 5/2011 | Ellis |
| 2011/0124466 A1 | 5/2011 | Nishimura |
| 2011/0124476 A1 | 5/2011 | Holley |
| 2011/0131005 A1 | 6/2011 | Ueshima et al. |
| 2011/0136627 A1 | 6/2011 | Williams |
| 2011/0143769 A1 | 6/2011 | Jones et al. |
| 2011/0143898 A1 | 6/2011 | Trees |
| 2011/0152037 A1 | 6/2011 | Tsou |
| 2011/0152038 A1 | 6/2011 | Freitag |
| 2011/0152039 A1 | 6/2011 | Hendrickson et al. |
| 2011/0152635 A1 | 6/2011 | Morris et al. |
| 2011/0165995 A1 | 7/2011 | Paulus |
| 2011/0172060 A1 | 7/2011 | Morales et al. |
| 2011/0175744 A1 | 7/2011 | Englert et al. |
| 2011/0181420 A1 | 7/2011 | Mack et al. |
| 2011/0188269 A1 | 8/2011 | Hosotani |
| 2011/0197157 A1 | 8/2011 | Hoffman et al. |
| 2011/0199799 A1 | 8/2011 | Hui et al. |
| 2011/0201481 A1 | 8/2011 | Lo |
| 2011/0202236 A1 | 8/2011 | Galasso et al. |
| 2011/0205164 A1 | 8/2011 | Hansen et al. |
| 2011/0221672 A1 | 9/2011 | Osterhout et al. |
| 2011/0237396 A1 | 9/2011 | Lu |
| 2011/0237399 A1 | 9/2011 | Toback |
| 2011/0247530 A1 | 10/2011 | Coffman |
| 2011/0251021 A1 | 10/2011 | Zavadsky et al. |
| 2011/0252597 A1 | 10/2011 | Burris et al. |
| 2011/0256988 A1 | 10/2011 | Weier |
| 2011/0257797 A1 | 10/2011 | Burris et al. |
| 2011/0263384 A1 | 10/2011 | Drazan |
| 2011/0269517 A1 | 11/2011 | Englert et al. |
| 2011/0269604 A1 | 11/2011 | Tseng |
| 2011/0275482 A1 | 11/2011 | Brodess et al. |
| 2011/0275489 A1 | 11/2011 | Apau |
| 2011/0275499 A1 | 11/2011 | Eschenbach |
| 2011/0281691 A1 | 11/2011 | Ellis |
| 2011/0283188 A1 | 11/2011 | Farrenkopf et al. |
| 2011/0283231 A1 | 11/2011 | Richstein et al. |
| 2011/0308919 A1 | 12/2011 | Hahn |
| 2011/0312473 A1 | 12/2011 | Chu et al. |

(56) References Cited

U.S. PATENT DOCUMENTS

| | | |
|---|---|---|
| 2011/0319229 A1 | 12/2011 | Corbalis et al. |
| 2012/0004075 A1 | 1/2012 | Kissel et al. |
| 2012/0004080 A1 | 1/2012 | Webb |
| 2012/0010053 A1 | 1/2012 | Bayerlein et al. |
| 2012/0015778 A1 | 1/2012 | Lee et al. |
| 2012/0015779 A1 | 1/2012 | Powch et al. |
| 2012/0015784 A1 | 1/2012 | Reed |
| 2012/0020135 A1 | 1/2012 | McCune |
| 2012/0021873 A1 | 1/2012 | Brunner |
| 2012/0021875 A1 | 1/2012 | Karl |
| 2012/0029666 A1 | 2/2012 | Crowley et al. |
| 2012/0032896 A1 | 2/2012 | Vesely |
| 2012/0046144 A1 | 2/2012 | Lin et al. |
| 2012/0071301 A1 | 3/2012 | Kaylor et al. |
| 2012/0088633 A1 | 4/2012 | Crafton |
| 2012/0088634 A1 | 4/2012 | Heidecke |
| 2012/0088640 A1 | 4/2012 | Wissink |
| 2012/0116684 A1 | 5/2012 | Ingrassia et al. |
| 2012/0132877 A1 | 5/2012 | Wang |
| 2012/0133192 A1 | 5/2012 | Simpson |
| 2012/0165162 A1 | 6/2012 | Lu |
| 2012/0169603 A1 | 7/2012 | Peterson et al. |
| 2012/0174833 A1 | 7/2012 | Early |
| 2012/0178590 A1 | 7/2012 | Lu |
| 2012/0178591 A1 | 7/2012 | Remelius |
| 2012/0187012 A1 | 7/2012 | TeVault et al. |
| 2012/0190502 A1 | 7/2012 | Paulus et al. |
| 2012/0212505 A1 | 8/2012 | Burroughs et al. |
| 2012/0218184 A1 | 8/2012 | Wissmar |
| 2012/0230504 A1 | 9/2012 | Kuroda |
| 2012/0242774 A1 | 9/2012 | Numano et al. |
| 2012/0248263 A1 | 10/2012 | Grotenhuis |
| 2012/0252580 A1 | 10/2012 | Dugan |
| 2012/0253234 A1 | 10/2012 | Yang et al. |
| 2012/0253489 A1 | 10/2012 | Dugan |
| 2012/0258433 A1 | 10/2012 | Hope et al. |
| 2012/0263892 A1 | 10/2012 | Rodgers |
| 2012/0270705 A1 | 10/2012 | Lo |
| 2012/0271143 A1 | 10/2012 | Aragones et al. |
| 2012/0277040 A1 | 11/2012 | Vincent et al. |
| 2012/0277891 A1 | 11/2012 | Aragones et al. |
| 2012/0293141 A1 | 11/2012 | Zhang et al. |
| 2012/0296455 A1 | 11/2012 | Ohnemus et al. |
| 2012/0298017 A1 | 11/2012 | Chen |
| 2012/0300515 A1 | 11/2012 | Carletti et al. |
| 2012/0302408 A1 | 11/2012 | Burger |
| 2012/0319604 A1 | 12/2012 | Walters |
| 2012/0326873 A1 | 12/2012 | Utter, II |
| 2013/0002533 A1 | 1/2013 | Burroughs et al. |
| 2013/0004010 A1 | 1/2013 | Royer |
| 2013/0009993 A1 | 1/2013 | Horseman |
| 2013/0017929 A1 | 1/2013 | Hendrickson et al. |
| 2013/0018494 A1 | 1/2013 | Amini |
| 2013/0034671 A1 | 2/2013 | George |
| 2013/0035612 A1 | 2/2013 | Mason et al. |
| 2013/0040783 A1 | 2/2013 | Duda et al. |
| 2013/0041590 A1 | 2/2013 | Burich et al. |
| 2013/0041617 A1 | 2/2013 | Pease et al. |
| 2013/0044521 A1 | 2/2013 | Zhao et al. |
| 2013/0050973 A1 | 2/2013 | Rohrbach |
| 2013/0053222 A1 | 2/2013 | Lo |
| 2013/0053990 A1 | 2/2013 | Ackland |
| 2013/0092647 A1 | 4/2013 | Chen |
| 2013/0095959 A1 | 4/2013 | Marty |
| 2013/0095978 A1 | 4/2013 | Sauter |
| 2013/0116095 A1 | 5/2013 | Hsieh |
| 2013/0123073 A1 | 5/2013 | Olson et al. |
| 2013/0130868 A1 | 5/2013 | Hou |
| 2013/0130869 A1 | 5/2013 | Hou |
| 2013/0139736 A1 | 6/2013 | Flaherty |
| 2013/0141235 A1 | 6/2013 | Utter, II |
| 2013/0143721 A1 | 6/2013 | Dalebout |
| 2013/0147411 A1 | 6/2013 | Pang et al. |
| 2013/0150214 A1 | 6/2013 | Wu |
| 2013/0154441 A1 | 6/2013 | Redmond |
| 2013/0165297 A1 | 6/2013 | Daly |
| 2013/0172152 A1 | 7/2013 | Watterson |
| 2013/0182781 A1 | 7/2013 | Matsutani |
| 2013/0185003 A1 | 7/2013 | Carbeck et al. |
| 2013/0190136 A1 | 7/2013 | Watterson |
| 2013/0190143 A1 | 7/2013 | Greenhill et al. |
| 2013/0190657 A1 | 7/2013 | Flaction et al. |
| 2013/0196821 A1 | 8/2013 | Watterson et al. |
| 2013/0196826 A1 | 8/2013 | Colledge |
| 2013/0196827 A1 | 8/2013 | Chang |
| 2013/0203561 A1 | 8/2013 | Lee et al. |
| 2013/0211858 A1 | 8/2013 | Ohnemus et al. |
| 2013/0228063 A1 | 9/2013 | Turner |
| 2013/0228422 A1 | 9/2013 | Mathieu |
| 2013/0231219 A1 | 9/2013 | Huang |
| 2013/0237383 A1 | 9/2013 | Chen |
| 2013/0245966 A1 | 9/2013 | Burroughs et al. |
| 2013/0263418 A1 | 10/2013 | Johnson, Jr. |
| 2013/0267386 A1 | 10/2013 | Her |
| 2013/0274040 A1 | 10/2013 | Coza et al. |
| 2013/0274069 A1 | 10/2013 | Watterson et al. |
| 2013/0274071 A1 | 10/2013 | Wang |
| 2013/0280682 A1 | 10/2013 | Levine et al. |
| 2013/0324368 A1 | 12/2013 | Aragones et al. |
| 2013/0325394 A1 | 12/2013 | Yuen et al. |
| 2013/0337981 A1 | 12/2013 | Habing |
| 2013/0338802 A1 | 12/2013 | Winsper et al. |
| 2013/0346043 A1 | 12/2013 | Mewes et al. |
| 2014/0011645 A1 | 1/2014 | Johnson et al. |
| 2014/0026788 A1 | 1/2014 | Kallio, III et al. |
| 2014/0031703 A1 | 1/2014 | Rayner et al. |
| 2014/0039840 A1 | 2/2014 | Yuen et al. |
| 2014/0052280 A1 | 2/2014 | Yuen et al. |
| 2014/0056461 A1 | 2/2014 | Afshar |
| 2014/0073488 A1 | 3/2014 | Wu |
| 2014/0077494 A1 | 3/2014 | Sutkowski |
| 2014/0080678 A1 | 3/2014 | Wu |
| 2014/0085077 A1 | 3/2014 | Luna et al. |
| 2014/0100464 A1 | 4/2014 | Kaleal et al. |
| 2014/0102340 A1 | 4/2014 | Kooistra |
| 2014/0121066 A1 | 5/2014 | Huang et al. |
| 2014/0139450 A1 | 5/2014 | Levesque et al. |
| 2014/0156228 A1 | 6/2014 | Molettiere et al. |
| 2014/0171266 A1 | 6/2014 | Hawkins, III et al. |
| 2014/0187383 A1 | 7/2014 | Martin |
| 2014/0195103 A1 | 7/2014 | Nassef |
| 2014/0221160 A1 | 8/2014 | Hardy et al. |
| 2014/0222173 A1 | 8/2014 | Giedwoyn et al. |
| 2014/0265690 A1 | 9/2014 | Henderson |
| 2014/0270375 A1 | 9/2014 | Canavan et al. |
| 2014/0274564 A1 | 9/2014 | Greenbaum |
| 2014/0274579 A1 | 9/2014 | Olson |
| 2014/0338120 A1 | 11/2014 | Baugh et al. |
| 2014/0358473 A1 | 12/2014 | Goel et al. |
| 2014/0360413 A1 | 12/2014 | Schenk |
| 2015/0001048 A1 | 1/2015 | Koppes et al. |
| 2015/0003621 A1 | 1/2015 | Trammell |
| 2015/0004579 A1 | 1/2015 | Shelton |
| 2015/0016623 A1 | 1/2015 | Trammell |
| 2015/0044648 A1 | 2/2015 | White et al. |
| 2015/0048807 A1 | 2/2015 | Fan et al. |
| 2015/0051051 A1 | 2/2015 | Liu et al. |
| 2015/0065273 A1 | 3/2015 | Lake |
| 2015/0065301 A1 | 3/2015 | Oteman |
| 2015/0105220 A1 | 4/2015 | Hong |
| 2015/0182782 A1 | 7/2015 | Cutler |
| 2015/0192929 A1 | 7/2015 | Rihn et al. |
| 2015/0199494 A1 | 7/2015 | Koduri et al. |
| 2015/0201722 A1 | 7/2015 | Brouard |
| 2015/0202487 A1 | 7/2015 | Wu |
| 2015/0209610 A1 | 7/2015 | Dalebout et al. |
| 2015/0209617 A1 | 7/2015 | Hsiao |
| 2015/0238806 A1 | 8/2015 | Mintz |
| 2015/0246751 A1 | 9/2015 | Spivack et al. |
| 2015/0250304 A1 | 9/2015 | Dalebout |
| 2015/0251047 A1 | 9/2015 | Maaniitty |
| 2015/0251048 A1 | 9/2015 | Dalebout |
| 2015/0251055 A1 | 9/2015 | Ashby |
| 2015/0253210 A1 | 9/2015 | Ashby et al. |

(56) References Cited

U.S. PATENT DOCUMENTS

| | | |
|---|---|---|
| 2015/0265903 A1 | 9/2015 | Kolen et al. |
| 2015/0295397 A1 | 10/2015 | Lin et al. |
| 2015/0314184 A1 | 11/2015 | Moya Saez |
| 2015/0335941 A1 | 11/2015 | Lo |
| 2015/0346994 A1 | 12/2015 | Chanyontpatanakul |
| 2015/0352396 A1 | 12/2015 | Dalebout |
| 2015/0352401 A1 | 12/2015 | Johnson |
| 2015/0352402 A1 | 12/2015 | Arnold et al. |
| 2015/0367158 A1 | 12/2015 | Pretz et al. |
| 2015/0367176 A1 | 12/2015 | Bejestan et al. |
| 2016/0008650 A1 | 1/2016 | Jue et al. |
| 2016/0016035 A1 | 1/2016 | Hao |
| 2016/0027325 A1 | 1/2016 | Malhotra |
| 2016/0038785 A1 | 2/2016 | Netter |
| 2016/0047446 A1 | 2/2016 | Hung |
| 2016/0066818 A1 | 3/2016 | Cowley et al. |
| 2016/0074701 A1 | 3/2016 | Wiener |
| 2016/0074705 A1 | 3/2016 | Wiener |
| 2016/0096064 A1 | 4/2016 | Gatti |
| 2016/0121161 A1 | 5/2016 | Mountain |
| 2016/0175643 A1 | 6/2016 | Kueker et al. |
| 2016/0184625 A1 | 6/2016 | Chang |
| 2016/0193518 A1 | 7/2016 | Baxter |
| 2016/0211841 A1 | 7/2016 | Harrison |
| 2016/0219968 A1 | 8/2016 | Martin |
| 2016/0263426 A1 | 9/2016 | Mueller et al. |
| 2016/0287930 A1 | 10/2016 | Moser |
| 2016/0303421 A1 | 10/2016 | Tyger et al. |
| 2016/0317861 A1 | 11/2016 | Dalebout |
| 2016/0367851 A1 | 12/2016 | Astilean et al. |
| 2017/0056716 A1 | 3/2017 | Cutler |
| 2017/0056726 A1 | 3/2017 | Dalebout et al. |
| 2017/0068782 A1 | 3/2017 | Pillai et al. |
| 2017/0113093 A1 | 4/2017 | Bellavista et al. |
| 2017/0120102 A1 | 5/2017 | Chen |
| 2017/0128784 A1 | 5/2017 | Molins et al. |
| 2017/0136280 A1 | 5/2017 | Lee |
| 2017/0136288 A1 | 5/2017 | Huang |
| 2017/0136289 A1 | 5/2017 | Frank |
| 2017/0136291 A1 | 5/2017 | Huang |
| 2017/0136339 A1 | 5/2017 | Habiche |
| 2017/0165523 A1 | 6/2017 | Chou |
| 2017/0189745 A1 | 7/2017 | Hamilton et al. |
| 2017/0216660 A1 | 8/2017 | Lernihan |
| 2017/0266483 A1 | 9/2017 | Dalebout et al. |
| 2017/0266532 A1 | 9/2017 | Watterson |
| 2017/0266533 A1 | 9/2017 | Dalebout |
| 2017/0266534 A1 | 9/2017 | Watterson |
| 2017/0266535 A1 | 9/2017 | Watterson |
| 2017/0274242 A1 | 9/2017 | Corbalis |
| 2017/0326411 A1 | 11/2017 | Watterson |
| 2017/0340917 A1 | 11/2017 | Chang |
| 2018/0001135 A1 | 1/2018 | Powell |
| 2018/0036585 A1 | 2/2018 | Powell |
| 2018/0056111 A1 | 3/2018 | Chiang et al. |
| 2018/0092603 A1 | 4/2018 | Duan et al. |
| 2018/0099179 A1 | 4/2018 | Chatterton et al. |
| 2018/0099180 A1 | 4/2018 | Wilkinson |
| 2018/0099181 A1 | 4/2018 | Powell et al. |
| 2018/0104533 A1 | 4/2018 | Powell et al. |
| 2018/0111018 A1 | 4/2018 | Lee |
| 2018/0117385 A1 | 5/2018 | Watterson et al. |
| 2018/0117388 A1 | 5/2018 | Porter |
| 2018/0117419 A1 | 5/2018 | Jackson |
| 2018/0147440 A1 | 5/2018 | Lin |
| 2018/0154205 A1 | 6/2018 | Watterson |

* cited by examiner

CONTROLS FOR AN EXERCISE DEVICE

RELATED APPLICATIONS

This application claims priority to U.S. patent application Ser. No. 62/104,146 titled "Controls for an Exercise Device" and filed on 16 Jan. 2015, which application is herein incorporated by reference for all that it discloses.

BACKGROUND

Aerobic exercise is a popular form of exercise that improves one's cardiovascular health by reducing blood pressure and providing other benefits to the human body. Aerobic exercise generally involves low intensity physical exertion over a long duration of time. Typically, the human body can adequately supply enough oxygen to meet the body's demands at the intensity levels involved with aerobic exercise. Popular forms of aerobic exercise include running, jogging, swimming, and cycling among others activities. In contrast, anaerobic exercise typically involves high intensity exercises over a short duration of time. Popular forms of anaerobic exercise include strength training and short distance running.

Many choose to perform aerobic exercises indoors, such as in a gym or their home. Often, a user uses an aerobic exercise machine to have an aerobic workout indoors. One such type of aerobic exercise machine is a treadmill, which is a machine that has a running deck attached to a support frame. The running deck can support the weight of a person using the machine. The running deck incorporates a tread belt that is driven by a motor. A user can run or walk in place on the tread belt by running or walking at the tread belt's speed. The speed and other operations of the treadmill are generally controlled through a control module that is also attached to the support frame and within a convenient reach of the user. The control module can include a display, buttons for increasing or decreasing a speed of the conveyor belt, controls for adjusting a tilt angle of the running deck, or other controls. Other popular exercise machines that allow a user to perform aerobic exercises indoors include elliptical machines, rowing machines, stepper machines, and stationary bikes to name a few.

One type of treadmill is disclosed in U.S. Pat. No. 5,512,025 issued to William T. Dalebout, et al. In this reference, a control console for exercise machines, such as treadmills, has a microprocessor to generate signals to control the exercise. The console is operable to control an exercise program, which has a series of time segments for which the difficulty levels are individually specified, and to provide a display of the program time segments. The console is further operable to display and store user-designed programs of the type described. Optionally, the console is operable to control two difficulty parameters of an exercise machine. The console may also include preset programs selectable by a user. The preset programs may include a fitness test comprising a series of exercise time segments of increasing difficulty, in which a user's fitness level is based on the user's inability to continue exercising beyond a particular time segment. U.S. Pat. No. 5,512,025 is herein incorporated by reference for all that it contains.

SUMMARY

In one aspect of the invention, an exercise machine includes a frame.

In one aspect of the invention, the exercise machine includes a movable element that is movable in a performance of an exercise, the movable element having at least one selectively adjustable operating parameter that selectively alters a difficulty of the exercise.

In one aspect of the invention, the exercise machine includes a recall mechanism connected to the frame.

In one aspect of the invention, the exercise machine includes a processor and memory.

In one aspect of the invention, the memory comprises programmed instructions executable by the processor to apply a first difficulty setting of the at least one selectively adjustable operating parameter to the movable element.

In one aspect of the invention, the programmed instructions are further executable by the processor to selectively store the first difficulty setting in the memory in response to store instructions from a user.

In one aspect of the invention, the programmed instructions are further executable by the processor to reapply the first difficulty setting to the movable element based on activation of the recall mechanism.

In one aspect of the invention, the movable element is a foot pedal.

In one aspect of the invention, the movable element is a tread belt.

In one aspect of the invention, the programmed instructions are further executable by the processor to change the difficulty to a second difficulty setting in response to activation of a toggle switch.

In one aspect of the invention, the programmed instructions to change the difficulty to the second difficulty setting are executable by the processor in response to second command from an operation controller integrated into the exercise machine.

In one aspect of the invention, the programmed instructions to change the difficulty to the second difficulty setting are executable by the processor in response to activation of a stop mechanism.

In one aspect of the invention, the programmed instructions are further executable by the processor to change the difficulty back to the first difficulty setting from the second difficulty setting based on activation of the recall mechanism.

In one aspect of the invention, the exercise machine includes a console connected to the frame.

In one aspect of the invention, the operating controller is integrated into the console.

In one aspect of the invention, the frame includes an arm rest.

In one aspect of the invention, the recall mechanism is integrated into the arm rest.

In one aspect of the invention, the arm rest has an upper section that is elevated higher than a base portion of a console of the exercise machine and a lower section where the lower section is located at an elevation that is lower than the console.

In one aspect of the invention, the recall mechanism is integrated into the upper section of the arm rest.

In one aspect of the invention, the recall mechanism is integrated into the lower section of the arm rest.

In one aspect of the invention, an exercise machine includes a frame.

In one aspect of the invention, the exercise machine includes a movable element that is movable in a performance of an exercise, the movable element having at least one selectively adjustable operating parameter that selectively alters a difficulty of the exercise.

In one aspect of the invention, the exercise machine includes a console connected to the frame.

In one aspect of the invention, the exercise machine includes an operation controller integrated into the console.

In one aspect of the invention, the exercise machine includes an arm rest integrated into the frame.

In one aspect of the invention, the exercise machine includes a recall mechanism integrated into the arm rest.

In one aspect of the invention, the exercise machine includes a processor and memory.

In one aspect of the invention, the memory has programmed instructions executable by the processor to apply a first difficulty setting of the at least one selectively adjustable operating parameter to the movable element based on a first command received through the operation controller.

In one aspect of the invention, the memory has programmed instructions executable by the processor to selectively store the first difficulty setting in the memory in response to store instructions from a user.

In one aspect of the invention, the memory has programmed instructions executable by the processor to change the difficulty to a second difficulty setting in response to user input.

In one aspect of the invention, the memory has programmed instructions executable by the processor to reapply the first difficulty setting from the second difficulty setting to the movable element based on activation of the recall mechanism.

In one aspect of the invention, the programmed instructions to change the difficulty to the second difficulty setting are executable by the processor in response to second command from the operation controller.

In one aspect of the invention, the programmed instructions to change the difficulty to the second difficulty setting are executable by the processor in response to activation of a stop mechanism.

In one aspect of the invention, the programmed instructions are further executable by the processor to change the difficulty to a second difficulty setting in response to activation of a toggle switch.

In one aspect of the invention, an exercise machine includes a frame.

In one aspect of the invention, a movable element that is movable in a performance of an exercise, the movable element having at least one selectively adjustable operating parameter that selectively alters a difficulty of the exercise.

In one aspect of the invention, the exercise machine includes a console connected to the frame.

In one aspect of the invention, the exercise machine includes an operation controller integrated into the console.

In one aspect of the invention, the exercise machine includes an arm rest connected to the frame, the arm rest having an upper section and a lower section where the lower section is spaced a shorter distance away from the movable element than the upper section.

In one aspect of the invention, the exercise machine includes a recall mechanism integrated into the lower section of the arm rest.

In one aspect of the invention, the exercise machine includes a stop mechanism connected to the frame.

In one aspect of the invention, the exercise machine includes a processor and memory.

In one aspect of the invention, the memory comprises programmed instructions executable by the processor to apply a first difficulty setting of the at least one selectively adjustable operating parameter to the movable element based on a first command received through the operation controller.

In one aspect of the invention, the memory comprises programmed instructions executable by the processor to selectively store the first difficulty setting in the memory in response to store instructions from a user.

In one aspect of the invention, the memory comprises programmed instructions executable by the processor to change the difficulty to a second difficulty setting based on activation of the stop mechanism.

In one aspect of the invention, the memory comprises programmed instructions executable by the processor to reapply the first difficulty setting from the second difficulty setting to the movable element based on activation of the recall mechanism.

In one aspect of the invention, an exercise machine includes a frame.

In one aspect of the invention, the exercise machine includes a movable element that is movable in a performance of an exercise, the movable element having at least one selectively adjustable operating parameter that selectively alters a difficulty of the exercise.

In one aspect of the invention, an exercise machine includes a recall mechanism connected to the frame.

In one aspect of the invention, an exercise machine includes a processor and memory.

In one aspect of the invention, the memory comprises programmed instructions executable by the processor to execute a programmed exercise routine that controls the at least one selectively operating parameter to the movable element.

In one aspect of the invention, the memory comprises programmed instructions executable by the processor to pause the programmed exercise routine based on predetermined breaks programmed into the programmed exercise routine.

In one aspect of the invention, the memory comprises programmed instructions executable by the processor to resume the programmed exercise routine based on activation of the recall mechanism.

In one aspect of the invention, the programmed instructions are further executable by the processor to instruct a user to perform an exercise movement off of the exercise machine in conjunction with pausing the programmed exercise routine.

In one aspect of the invention, the recall mechanism includes a button.

In one aspect of the invention, the recall mechanism includes a toggle switch.

In one aspect of the invention, the recall mechanism includes an icon of a touch screen.

In one aspect of the invention, the programmed instructions are further executable by the processor to calculate an energy expenditure value based at least in part on the programmed exercise routine.

In one aspect of the invention, the programmed instructions are further executable by the processor to calculate the energy expenditure value based at least in part on a received user weight.

In one aspect of the invention, the programmed instructions are further executable by the processor to calculate the energy expenditure value based at least in part on a received user gender.

In one aspect of the invention, the programmed instructions are further executable by the processor to calculate the energy expenditure value based at least in part on a received user age.

In one aspect of the invention, the programmed instructions are further executable by the processor to calculate the energy expenditure value based at least in part on a received user body composition.

In one aspect of the invention, the exercise machine includes an arm rest attached to the frame and the recall mechanism is integrated into the arm rest.

In one aspect of the invention, the exercise machine comprises tread belt and the arm rest is accessible to a user while the user exercises on the tread belt.

In one aspect of the invention, the recall mechanism is incorporated into a section of the arm rest that is accessible to the user when the user exercises on the tread belt with a backside of the user facing a console of the exercise machine attached to the frame.

In one aspect of the invention, the movable element is a foot pedal.

In one aspect of the invention, an exercise machine includes a frame.

In one aspect of the invention, the exercise machine includes a movable element that is movable in a performance of an exercise, the movable element having at least one selectively adjustable operating parameter that selectively alters a difficulty of the exercise.

In one aspect of the invention, the exercise machine includes a recall mechanism connected to the frame.

In one aspect of the invention, the exercise machine includes a processor and memory.

In one aspect of the invention, the memory comprises programmed instructions executable by the processor to execute a programmed exercise routine that controls the at least one selectively operating parameter to the movable element.

In one aspect of the invention, the memory comprises programmed instructions executable by the processor to pause the programmed exercise routine based on predetermined breaks programmed into the programmed exercise routine.

In one aspect of the invention, the memory comprises programmed instructions executable by the processor to instruct a user to perform an exercise movement off of the exercise machine in conjunction with pausing the programmed exercise routine.

In one aspect of the invention, the memory comprises programmed instructions executable by the processor to resume the programmed exercise routine based on activation of the recall mechanism.

In one aspect of the invention, the programmed instructions are further executable by the processor to calculate an energy expenditure value based at least in part on the programmed exercise routine.

In one aspect of the invention, the programmed instructions are further executable by the processor to calculate the energy expenditure value based at least in part on at least one of a user weight, user gender, user age, and a user body composition.

In one aspect of the invention, the recall mechanism includes a toggle switch.

In one aspect of the invention, the recall mechanism is incorporated into a section of an arm rest that is accessible to the user when the user exercises on a tread belt of the exercise machine with a backside of the user facing a console of the exercise machine attached to the frame.

In one aspect of the invention, an exercise machine includes a frame.

In one aspect of the invention, the exercise machine includes a movable element that is movable in a performance of an exercise, the movable element having at least one selectively adjustable operating parameter that selectively alters a difficulty of the exercise.

In one aspect of the invention, the exercise machine includes a recall mechanism connected to the frame.

In one aspect of the invention, the exercise machine includes a processor and memory.

In one aspect of the invention, the memory comprises programmed instructions executable by the processor to execute a programmed exercise routine that controls the at least one selectively operating parameter to the movable element.

In one aspect of the invention, the memory comprises programmed instructions executable by the processor to pause the programmed exercise routine based on predetermined breaks programmed into the programmed exercise routine.

In one aspect of the invention, the memory comprises programmed instructions executable by the processor to instruct a user to perform an exercise movement off of the exercise machine in conjunction with pausing the programmed exercise routine.

In one aspect of the invention, the memory comprises programmed instructions executable by the processor to resume the programmed exercise routine based on activation of the recall mechanism.

In one aspect of the invention, the memory comprises programmed instructions executable by the processor to calculate an energy expenditure value based at least in part on the programmed exercise routine and at least one of a user weight, user gender, user age, and a user body composition.

In one aspect of the invention, an exercise machine includes a frame.

In one aspect of the invention, the exercise machine includes an exercise deck attached to the frame.

In one aspect of the invention, the exercise machine includes a tread belt rotatably disposed about the exercise deck between a front pulley and rear pulley where a top surface of the tread belt moves from the front pulley to the rear pulley.

In one aspect of the invention, the exercise machine includes an arm rest integrated into the frame.

In one aspect of the invention, a first section of the arm rest accessible to a user performing an exercise on the tread belt when a backside of the user faces the front pulley.

In one aspect of the invention, the exercise machine includes a user input integrated into the first section.

In one aspect of the invention, the user input integrated into the first section is a physiological parameter input.

In one aspect of the invention, the physiological parameter input is a heart rate parameter.

In one aspect of the invention, the user input integrated into the first section is an exercise deck incline input.

In one aspect of the invention, the user input integrated into the first section is a tread belt speed input.

In one aspect of the invention, the user input integrated into the first section is a stop input.

In one aspect of the invention, the exercise machine includes a processor and memory.

In one aspect of the invention, the memory comprises programmed instructions executable by the processor to apply a first difficulty setting of at least one selectively adjustable operating parameter to the tread belt.

In one aspect of the invention, the memory comprises programmed instructions executable by the processor to apply a first difficulty setting of at least one selectively adjustable operating parameter to the tread belt.

In one aspect of the invention, the memory comprises programmed instructions executable by the processor to reapply the first difficulty setting to the tread belt based on activation of a recall mechanism.

In one aspect of the invention, the recall mechanism is integrated into the first section of the arm rest.

In one aspect of the invention, the user input integrated into the first section is redundant to a console input integrated into a console attached to the frame.

In one aspect of the invention, the arm rest further comprises a second section positioned a greater distance away from the exercise deck than the first section, and the second section comprises a second input.

In one aspect of the invention, the second input is redundant with the user input integrated into the first section.

In one aspect of the invention, the exercise machine includes a processor and memory.

In one aspect of the invention, the memory comprising programmed instructions executable by the processor to execute a programmed exercise routine.

In one aspect of the invention, the programmed instructions are further executable by the processor to instruct the user to perform the exercise on the tread belt so that the backside of the user faces the front pulley.

In one aspect of the invention, the programmed instructions are further executable by the processor to calculate an energy expenditure value based at least in part on the exercise performed with the backside of the user facing the front pulley.

In one aspect of the invention, the exercise deck comprises a length in a longest dimension of the deck and midpoint divides the length into a front portion and a back portion; wherein the user input is superjacent the back portion.

In one aspect of the invention, an exercise machine includes a frame.

In one aspect of the invention, the exercise machine includes an exercise deck attached to the frame.

In one aspect of the invention, the exercise machine includes a tread belt movably disposed about the exercise deck, the tread belt has at least one selectively adjustable operating parameter that selectively alters a difficulty of an exercise performed on the tread belt.

In one aspect of the invention, the exercise machine includes a console connected to the frame.

In one aspect of the invention, the exercise machine includes an operation controller integrated into the console to control the at least one selectively adjustable operating parameter.

In one aspect of the invention, the exercise machine includes an arm rest integrated into the frame.

In one aspect of the invention, the exercise machine includes a first section of the arm rest comprising a recall mechanism wherein the exercise deck comprises a length in a longest dimension of the deck and a midpoint divides the length into a front portion and a back portion; wherein the recall mechanism is superjacent the back portion.

In one aspect of the invention, the exercise machine includes a processor and memory.

In one aspect of the invention, the memory comprises programmed instructions executable by the processor to apply a first difficulty setting of the at least one selectively adjustable operating parameter to the tread belt.

In one aspect of the invention, the memory comprises programmed instructions executable by the processor to selectively store the first difficulty setting in the memory based on user input.

In one aspect of the invention, the memory comprises programmed instructions executable by the processor to reapply the first difficulty setting to the tread belt based on activation of the recall mechanism.

In one aspect of the invention, the recall mechanism is integrated into the first section of the arm rest.

In one aspect of the invention, the arm rest further comprises a second section positioned a greater distance away from the exercise deck than the first section, and the second section comprises a second input.

In one aspect of the invention, the second input is redundant with the user input integrated into the first section.

In one aspect of the invention, the programmable instructions are further executable by the processor to instruct the user to perform the exercise on the tread belt so that a backside of the user faces the console.

In one aspect of the invention, the programmable instructions are further executable by the processor to calculate an energy expenditure value based at least in part on the exercise performed with the backside of the user facing the console.

In one aspect of the invention, an exercise machine includes a frame.

In one aspect of the invention, the exercise machine includes an exercise deck attached to the frame.

In one aspect of the invention, the exercise machine includes a tread belt movably disposed about the exercise deck, the tread belt has at least one selectively adjustable operating parameter that selectively alters a difficulty of an exercise performed on the tread belt.

In one aspect of the invention, the exercise machine includes a console connected to the frame.

In one aspect of the invention, the exercise machine includes an operation controller integrated into the console to control the at least one selectively adjustable operating parameter.

In one aspect of the invention, the exercise machine includes an arm rest integrated into the frame.

In one aspect of the invention, the exercise machine includes a first section of the arm rest accessible to a user performing the exercise on the tread belt when a backside of the user faces the console.

In one aspect of the invention, a recall mechanism is integrated into the first section of the arm rest, the exercise deck comprises a length in a longest dimension of the deck and midpoint divides the length into a front portion and a back portion where the recall mechanism is superjacent the back portion.

In one aspect of the invention, the arm rest further comprises a second section positioned a greater distance away from the exercise deck than the first section.

In one aspect of the invention, a second input integrated into the second section.

In one aspect of the invention, the second input is redundant with the recall mechanism integrated into the first section.

In one aspect of the invention, the exercise machine includes a processor and memory.

In one aspect of the invention, the memory comprises programmed instructions executable by the processor to instruct the user to perform the exercise on the tread belt so that the backside of the user faces the console.

In one aspect of the invention, the memory comprises programmed instructions executable by the processor to apply a first difficulty setting of the at least one selectively adjustable operating parameter to the tread belt.

In one aspect of the invention, the memory comprises programmed instructions executable by the processor to selectively store the first difficulty setting in the memory based on user input.

In one aspect of the invention, the memory comprises programmed instructions executable by the processor to calculate an energy expenditure value based at least in part on the exercise performed with the backside of the user facing the console.

In one aspect of the invention, the memory comprises programmed instructions executable by the processor to reapply the first difficulty setting to the tread belt based on activation of the recall mechanism.

Any of the aspects of the invention detailed above may be combined with any other aspect of the invention detailed herein.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

Figure 1:
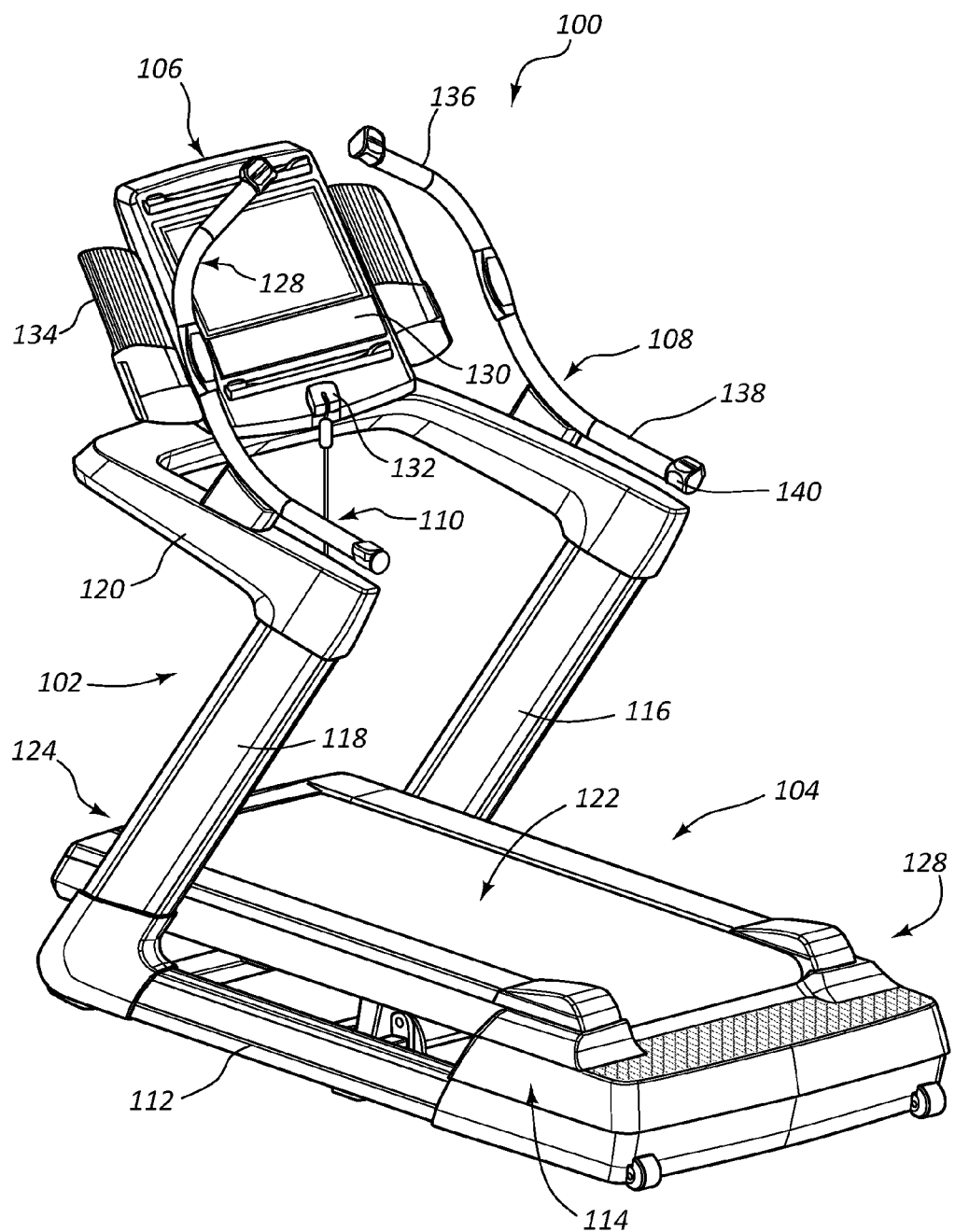
FIG. 1 illustrates a perspective view of an example of an exercise machine in accordance with the present disclosure.
Figure 2:
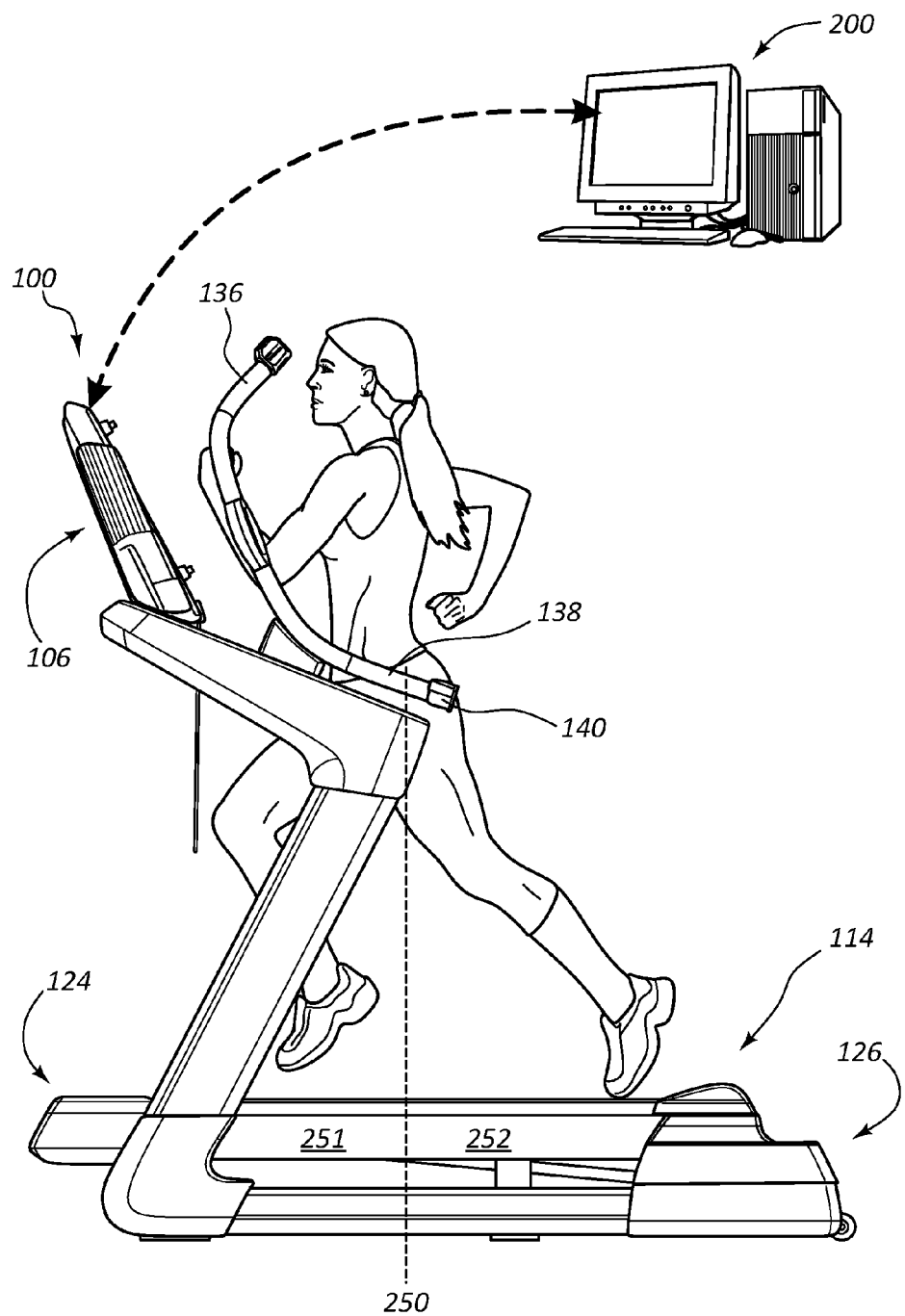
FIG. 2 illustrates a perspective view of an example of an exercise machine in communication with a remote device in accordance with the present disclosure.
Figure 3:
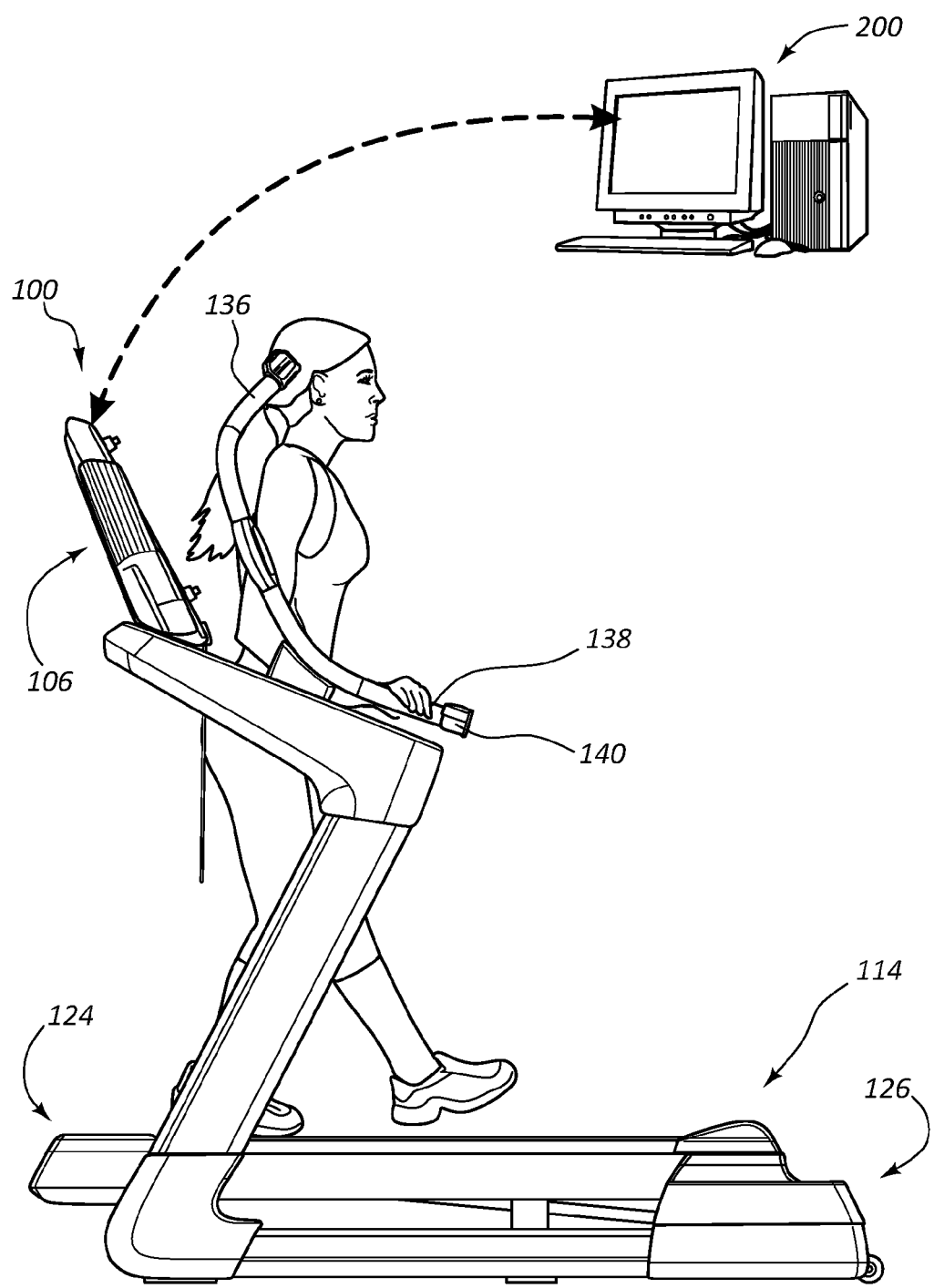
FIG. 3 illustrates a perspective diagram of an example of an exercise machine with a user walking backwards thereon in accordance with the present disclosure.

Particularly, with reference to the figures, FIGS. 1-3 illustrate examples of an exercise machine 100 in accordance with the present disclosure. FIG. 2 depicts a user working out on the exercise machine facing a forward direction, and FIG. 3 depicts a user working out facing a backwards direction. In these examples, the exercise machine includes a frame 102, an exercise deck 104, a console 106, a first arm rest 108, and a second arm rest 110.

In these examples, the frame 102 includes a base section 112 that is pivotally attached to a rear end 114 of the exercise deck 104. A first frame post 116 and a second frame post 118 extend upward from the base section 112. At top ends of the first post 116 and the second post 118, the posts 116, 118 are connected by a console section 120 of the frame 102. The console 106 and the first and second arm rests 108, 110 are attached to the console section 120 of the frame 102.

The exercise deck 104 includes a tread belt 122 that spans between a front pulley at a front end 124 of the exercise machine 100 and a rear pulley at a rear end 126 of the exercise machine 100. In some examples, one of the front pulley or the rear pulley is driven by a motor, which causes the tread belt 122 to rotate about the front and rear pulleys. In some examples, a top surface of the tread belt moves from the front pulley to the rear pulley. The speed of the tread belt 122 can be controlled by the user or an exercise program at a pace that the user desires to walk or run. In other examples, the speed of the tread belt 122 may be paced for riding a bicycle or another type of self-propelled exercise device on the exercise deck 104. An incline mechanism may be used to control the front to rear slope of the exercise deck 104. In the illustrated example, the slope of the exercise deck is relatively flat. However, in other examples, the incline mechanism may raise or lower a front section 127 of the exercise deck to create a different slope. Any appropriate type of incline mechanism may be used to raise and/or lower either a front section 127 or a rear section 129 of the exercise deck 104. Further, any appropriate type of slope may be achieved with the incline mechanism. In some examples, the front to rear slope of the exercise deck 104 may be negative 15.0 degrees where the front section 127 is lower than the rear section 129. In yet other examples, the front to rear slope may be a positive 45.0 degrees where the front section 127 is higher than the rear section 129. In other examples, the front to rear slope angle is between negative 45.0 degrees and positive 45.0 degrees. Further, in some embodiments, the exercise deck 104 is capable of changing its side to side tilt angle.

The console 106 includes a display 128, at least one operations controller 130, a stop mechanism 132, speakers 134, physiological sensors, timers, clocks, other features, or combinations thereof. The display 128 may be used to present videos, scenery, entertainment, images, clocks, physiological conditions of the user, touch screen buttons, other information, or combinations thereof. The operations controller 130 may be used to control various operating parameters of exercises performed on the exercise machine 100. Such operating parameters may include the side to side tilt of the exercise deck 104, the incline of the exercise deck 104, the speed of the tread belt 122, the volume of the speakers 134, image characteristics of the display 128, use of the timers, operation of the physiological sensors, or other functions. The operations controller 130 may be controlled with an input mechanism such as a push button, a touch screen icon, a lever, a dial, a switch, a microphone, a hand gesture camera, another type of input mechanism, or combinations thereof.

The stop mechanism 132 may be used to cause at least one of the operating parameters to stop. For example, activation of the stop mechanism 132 may cause an immediate stop of power to the motor driving the tread belt 122. In such an example, a user may activate the stop mechanism 132 in an emergency. In other examples, the user may activate the stop mechanism when the user desires to get off or leave the exercise machine 10. There are situations when the user may get off of the exercise deck 104 when the user has not finished his or her workout on the exercise machine 100. For example, the user's workout may include multiple types of exercises such as several rounds of running on the exercise deck 104 and weight lifting exercises off of the exercise machine 100. The user may get off of the exercise machine 100 to perform the weight lifting exercises and then resume training on the exercise machine 100. The user may cause the power to the tread belt's motor to be cut each time he or she gets off of the exercise machine 100 to perform these other exercises.

The physiological sensors may track physiological information about the user such as the user's heart rate, blood pressure, oxygen saturation level, pulse, respiration, muscle condition, or other physiological conditions. In some examples, such sensors are incorporated into the console 106. However, in other examples, such physiological sensors are incorporated into one of the first and second arm rests 108, 110. The physiological sensors may be used to monitor the health of the user which may assist the user in planning future workouts, in maintaining a target health condition during the workout, in calculating an energy expenditure value representing the amount of energy that the user expended during the workout, in performing other functions, or combinations thereof. Generating such an energy expenditure value may take into account the user's weight, age, height, gender, body composition, other personal information, or combinations thereof.

The processes for calculating the energy expenditure may be in communication with a remote device 200, which has access to personal information about the user. For example, the remote device 200 may include a profile of the user which includes the user's age, weigh, height, gender, body composition, health conditions, other personal information, or combinations thereof. In some cases, the remote device 200 includes a mobile device, a laptop, a remote computer, a server, a computing device, a data center, another type of device, or combinations thereof. Such profile information may be available to the user through an iFit program available through www.ifit.com and administered through ICON Health and Fitness, Inc. located in Logan, Utah, U.S.A. An example of a program that may be compatible with the principles described in this disclosure is described in U.S. Pat. No. 7,980,996 issued to Paul Hickman. U.S. Pat. No. 7,980,996 is herein incorporated by reference for all that it discloses. However, such profile information may be available through other types of programs. For example, such information may be gleaned from social media websites, blogs, government databases, private databases, other sources, or combinations thereof. In yet other examples, the user information may be accessible through the exercise machine 100. In such an example, the user may input the personal information into the exercise machine 100 before, after, or during the workout.

In the illustrated examples, the arm rests 108, 110 are connected to the console section 120 of the frame 102. The arm rests 108, 110 may each have an upper section 136 and a lower section 138 where the lower section 138 is spaced a shorter distance away from the exercise deck 104 than the upper section 136. The upper section 136 may be positioned to allow the user to grasp the arm rest when the user is walking, running, cycling, or performing another type of exercise on the exercise deck 104. During such exercises, the user may face the console 106 and reach his or her hands towards and grasp the upper section 136 of the arm rests 108, 110.

The lower section 138 of the arm rests 108, 110 may be oriented to allow the user to grasp the lower sections 138 when the user is on the exercise deck with his or her backside facing the console 106. In other words, the user can hold onto the lower sections 138 of the arm rests 108, 110 when the user is performing an exercise while facing the rear end 114 of the exercise deck. Performing exercises backwards, such as walking or running backwards can work different muscle groups and may be effective for expending additional energy in a shorter amount of time than when performing the same exercise forwards. The lower sections 138 of the arm rests 108, 110 may provide stability to the user when performing such backward exercises. The lower sections 138 of the arm rests 108, 110 may additionally locate input mechanisms for controlling operations of the exercise machine 100, sensors, stop mechanisms 132, recall mechanisms 140, or other types of controllers within the user's convenient reach while exercising backwards. In some examples, the recall mechanism is a toggle switch.

At least one controller may be integrated into the lower sections 138 of the arm rests 108, 110, which may give the user an ability to provide instructions to the exercise machine 100 while performing a backwards exercise. Such controllers may be redundant to the controllers integrated into the console 106, but in some examples, the controllers in the lower section 138 of the arm rests 108, 110 do not have redundant controllers integrated into the console 106. An example of a controller that may be integrated into the lower section 138 of the arm rests 108, 110 may include controllers for the incline of the exercise deck 104, the speed of the tread belt 122, the side to side tile of the exercise deck 104, the volume of the speakers 134, other types of parameters, or combinations thereof. Further, the stop mechanism may be integrated into the lower arm rest sections 138. In some instances, at least one of the physiological sensors is integrated into the lower arm rest sections 138.

The exercise machine 100 may also include a recall mechanism 140. The recall mechanism may be integrated into the console 106, the upper sections 136 of the arm rests 108, 110, the lower sections 138 of the arm rests 108, 110, another portion of the arm rests 108, 110, another location on the exercise machine 100, or combinations thereof. The user may use the recall mechanism 140 to cause at least one of the operating parameters of the exercise machine to return to a difficulty setting at which the operating parameter was previously operating. For example, in situations where the user is performing a workout that includes both exercises on the exercise machine 100 and off of the exercise machine 100, the user can use the stop mechanism 132 to stop the power to the tread belt's motor when getting off of the exercise machine and use the recall mechanism 140 to instruct the motor to resume the speed at which the tread belt 122 was previously moving prior to stopping the motor when the user resumes training on the exercise machine 100. In other examples, the recall mechanism 140 can be used to cause the exercise machine 100 to resume an incline of the exercise deck 104, resume a side to side tilt of the exercise deck 104, resume another operating parameter of the exercise machine 100, or combinations thereof.

The recall mechanism 140 may also be useful for interval exercises where the user desires to repeat an intense difficulty setting for at least one of the operating parameters for a short amount of time while exercising at lower intensity levels between intervals. In such a situation, the user may exercise at the desire exercise difficulty setting during an interval and cause the recall mechanism 140 to remember that difficulty setting. Then the user may exercise at a lower intensity and cause the recall mechanism 140 to remember that lower setting. Then the user may instruct the recall mechanism 140 to apply the first difficulty setting for the next interval. When the next interval is complete, the user can instruct the exercise machine 100 to resume the lower difficulty setting through the recall mechanism 140. Thus, the user may switch back and forth between two difficulty settings with the recall mechanism 140. In some examples, the user can record the desired difficulty settings in the exercise machine 100 without having to first perform exercises at those difficulty settings. For example, the user may input into the console 106 that the first difficulty setting is a tread belt speed of 10.0 miles per hour and that a second difficulty setting is a tread belt speed of 5.0 miles per hour without actually having to run at those speeds first.

In such an example, the user may control how long the exercise machine 100 operates at the desired difficulty settings by activating the recall mechanism 140 to switch to the previously operated difficulty settings at the moment that the user desires to make the switch. In such examples, the user may decide to exercise at the different difficulty settings at different time lengths. This may give a user who feels that he or she can exercise at the more intense difficulty setting for a longer time period than previously planned an option to perform the exercise at the more difficult setting longer. Likewise, the user who desires a longer rest period between intervals can lengthen the rest period as desired by keeping the exercise machine at the lower difficulty setting for a longer time period before manually instructing the exercise machine to switch to the more difficult setting through the recall mechanism 140.

While the examples above have been described with the recall mechanism 140 having the ability to store a single difficulty setting or store two difficulty settings, any appropriate number of difficulty settings may be stored with the recall mechanism 140. For example, the user may desire to repeat a series of progressively harder settings. In such an example, the user may instruct the exercise machine 100 to operate sequentially at a first difficulty setting, then a second difficulty setting, and then a third difficulty setting. The user may repeat that sequence of difficulty settings through use of the recall mechanism 140. Additionally, different difficulty settings may be stored for different types of workouts. For example, the user may cause the exercise machine 100 to store difficulty settings for walking backwards, sprint exercises, cardio workouts, cycling workouts, other types of workouts, or combinations thereof.

In some examples, the user may not know which difficulty setting is desirable for a particular exercise. In such examples, the user may tryout the exercise until he or she finds a difficulty setting that he or she feels is appropriate for that exercise. In such an example, the user may instruct the exercise machine 100 to store the desired setting. The user does not have to remember the specific details about the difficulty level, such as the speed, incline angle, side to side tilt angle, or other parameters. Instead, the user can merely cause the difficulty setting to be resumed by activating the recall mechanism at a later time. In some instances the difficulty setting is permanently stored for a user who uses the machine over a long time period. In other examples, the difficulty settings are stored for a short period of time, such as the time period of the workout. Additionally, the difficulty setting may include a setting for a specific operating parameter. In other cases, the difficulty settings include multiple operating parameters. For example, the difficulty setting may include both the tread belt speed and the exercise deck's front to rear incline slope.

The recall mechanism 140 may include a button, a lever, a dial, a switch, a touch screen button, a toggle switch, another type of input mechanism, or combinations thereof. In the example of FIG. 1, the recall mechanism 140 is integrated into the lower sections 138 of the arm rests 108, 110. In this example, the recall mechanism 140 has a toggle switch that allows the user to switch between two desired difficulty settings. Also, in the example of FIG. 1, the recall mechanism 140 also includes a toggle switch in the upper section 136 of the arm rests 108, 110.

The exercise machine 100 may include a programmed exercise routine that controls one or more of the operating parameters of the exercise machine 100. For example, the programmed exercise routine may cause the speed of the tread belt 122 to vary over a period of time, change the incline of the exercise deck 104 over a period of time, change the side to side tilt of the exercise deck 104 over the period of time, vary other parameters, or combinations thereof. In some examples, the programmed exercise routine may instruct the user to get off of the exercise machine 100 to perform an exercise without the exercise machine 100. For example, the programmed exercise routine may instruct the user to perform a number of push-ups, sit-ups, pull-ups, jumping exercises, core exercises, weight lifting exercises, exercises on a different exercise machine, or combinations thereof. The user may return to the exercise machine 100 after completing the instructed exercises and cause the programmed exercise routine to resume by activating the recall mechanism 140.

While the exercise machine 100 in the example of FIG. 1 is a treadmill, the principles described herein relating to the recall mechanism 140 may apply to any appropriate type of exercise machine. For example, the recall mechanism 140 may be incorporated into elliptical machines, stepper machines, skier machines, stationary bikes, rowing machines, other types of machines, or combinations thereof. For example, a non-exhaustive list of operating parameters that may resume a previous difficulty setting in an elliptical machine may include a foot pedal resistance parameter, an incline parameter, a stride length parameter, another type of parameter, a side to side tilt parameter, or combinations thereof. Further, a non-exhaustive list of operating parameters that may resume a previous difficulty setting in a stationary bike may include a foot pedal resistance parameter, a seat height parameter, another type of parameter, or combinations thereof. Also, a non-exhaustive list of operating parameters that may resume a previous difficulty setting in a rowing machine may include a hand pedal resistance parameter, a stroke length parameter, a stroke angle parameter, another type of parameter, or combinations thereof.

The exercise deck 104 has a length in a longest dimension of the deck 104 and midpoint 250 divides the length into a front portion 251 and a back portion 252. The recall mechanism 140, user input, and/or the controller may be superjacent the back portion of the exercise deck 104. The midpoint 250 may be half way between a first end and a second end of the exercise deck 104. In some examples, the recall mechanism 140, user input, and/or the controller that are superjacent the back portion 252 of the exercise deck 104 are accessible to the user when the user is exercising backwards on the treadmill. For example, the user may be able to reach forward to access the recall mechanism 140, user input, and/or the controller when the user is positioned on the exercise deck 104 with his or her backside facing the console 106 and/or front pulley.

Figure 4:
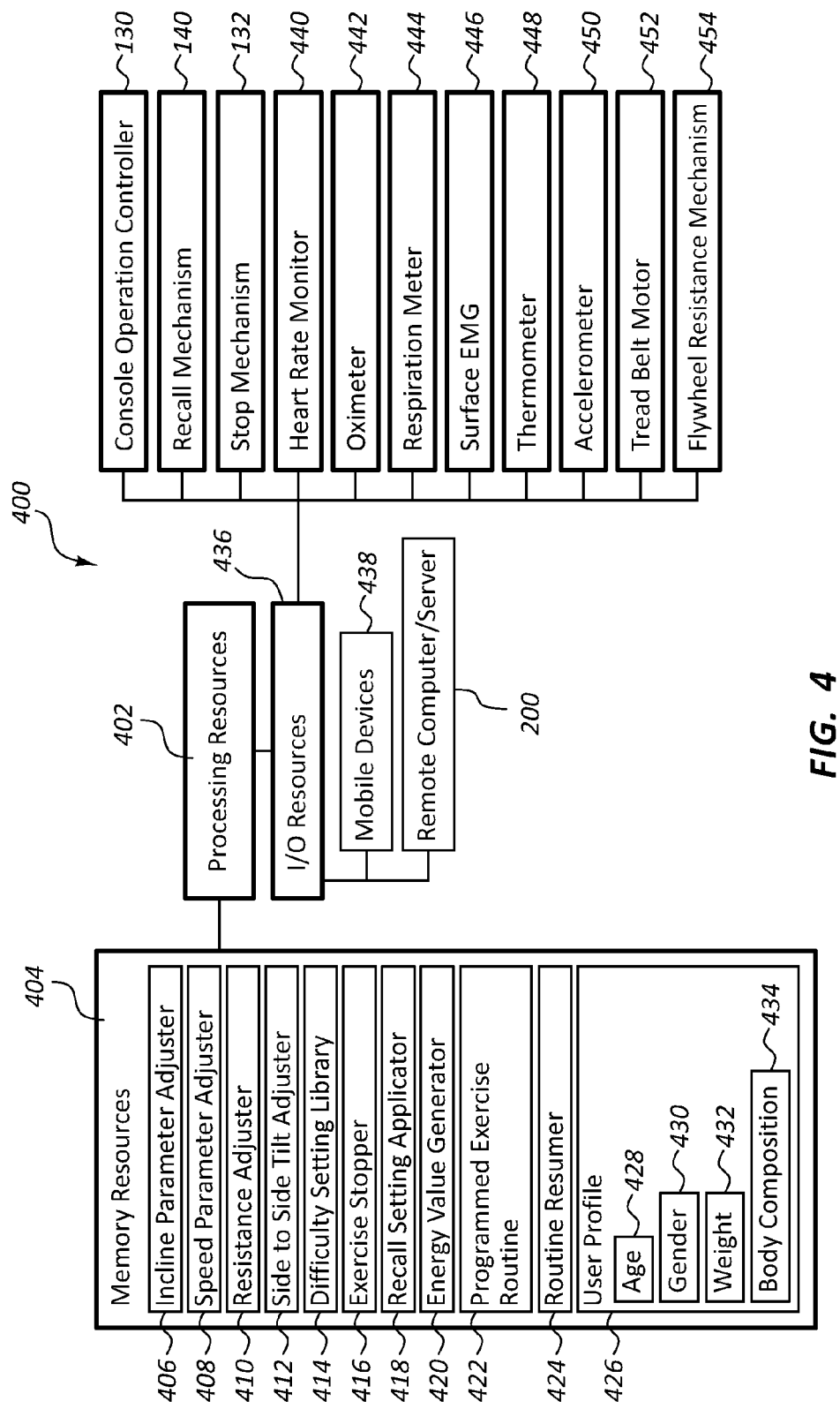
FIG. 4 illustrates a block diagram of an example of an exercise system in accordance with the present disclosure.

FIG. 4 illustrates a perspective view of an example of an exercise system 400 in accordance with the present disclosure. The exercise system 400 may include a combination of hardware and programmed instructions for executing the functions of the exercise system 400. In this example, the exercise system 400 includes processing resources 402 that are in communication with memory resources 404. Processing resources 402 include at least one processor and other resources used to process the programmed instructions. The memory resources 404 represent generally any memory capable of storing data such as programmed instructions or data structures used by the exercise system 400. The programmed instructions and data structures shown stored in the memory resources 404 include an incline parameter adjuster 406, a speed parameter adjuster 408, a resistance adjuster 410, a side to side tilt adjuster 412, a difficulty setting library 414, an exercise stopper 416, a recall setting applicator 418, an energy value generator 420, a programmed exercise routine 422, a routine resumer 424, a user profile 426, an age parameter 428, a gender parameter 430, a weight parameter 432, and a body composition parameter 434.

The processing resources 402 may be in communication with I/O resources 436 that communicate with external devices. Such external devices may include a mobile device 438, a remote device 200, a remote computer, a remote server, another external device, or combinations thereof. In some examples, the exercise system 400 communicates with the remote device through a mobile device which relays communications between the exercise system 400 and the remote device. In other examples, the mobile device has access to information about the user. In some cases, the remote device collects information about the user throughout the day, such as tracking calories, exercise, activity level, sleep, other types of information, or combination thereof.

The remote device 200 may execute a program that can provide useful information to the exercise system 400. An example of a program that may be compatible with the principles described herein includes the iFit program as described above. In some examples, the user information accessible through the remote device includes the user's age, gender, body composition, height, weight, health conditions, other types of information, or combinations thereof.

The processing resources 402, memory resources 404 and remote devices may communicate over any appropriate network and/or protocol through the I/O resources 436. In some examples, the I/O resources 436 includes a transceiver for wired and/or wireless communications. For example, these devices may be capable of communicating using the ZigBee protocol, Z-Wave protocol, BlueTooth protocol, Wi-Fi protocol, Global System for Mobile Communications (GSM) standard, another standard, or combinations thereof. In other examples, the user can directly input some information into the exercise system 400 through a digital input/output mechanism, a mechanical input/output mechanism, another type of mechanism, or combinations thereof.

The memory resources 404 include a computer readable storage medium that contains computer readable program code to cause tasks to be executed by the processing resources 402. The computer readable storage medium may be a tangible and/or non-transitory storage medium. The computer readable storage medium may be any appropriate storage medium that is not a transmission storage medium. A non-exhaustive list of computer readable storage medium types includes non-volatile memory, volatile memory, random access memory, write only memory, flash memory, electrically erasable program read only memory, magnetic based memory, other types of memory, or combinations thereof.

The incline parameter adjuster 406 represents programmed instructions that, when executed, cause the processing resources 402 to adjust the incline for those types of exercise machines that have an exercise deck 104 or another movable element that can be inclined. The speed parameter adjuster 408 represents programmed instructions that, when executed, cause the processing resources 402 to adjust the speed of those types of exercise machines that have tread belts 122. The resistance adjuster 410 represents programmed instructions that, when executed, cause the processing resources 402 to adjust the operating parameter of resistance for those types of exercise machines that have a resistance mechanism. The side to side tilt adjuster 412 represents programmed instructions that, when executed, cause the processing resources 402 to adjust the side to side tilt for those types of exercise machines that have an exercise deck 104 or another movable element that can be tilted side to side.

The difficulty setting library 414 may include the various difficulty settings for use in a programmed exercise routine or difficulty settings identified by the user. The library 414 may associate specific difficulty settings with the recall mechanism 140 such that when a recall command is received, the associated difficulty settings are applied. The exercise stopper 416 represents programmed instructions that, when executed, cause the processing resources 402 to stop an exercise by reducing the value of at least one operating parameter to a zero value. In some examples, this may include cutting power to a tread belt motor 452 that drives the tread belt so that the speed of the tread belt 122 approaches zero miles per hour. In other examples, a resistance setting is reduced to having substantially no resistance added to the foot pedal or another type of movable element.

The recall setting applicator 418 represents programmed instructions that, when executed, cause the processing resources 402 to apply the difficulty setting to the appropriate component of the exercise machine 100. For example, the difficulty setting library 414 may indicate the appropriate difficulty setting for a flywheel resistance mechanism 454 of an elliptical machine at a specific amount of force. In such an instance, that specific amount of force is applied to the flywheel resistance mechanism 454 to resist movement of the elliptical machine's foot pedals.

The energy value generator 420 represents programmed instructions that, when executed, cause the processing resources 402 to generate a value representative of the energy expended by the user during at least a portion of the user's workout. Such an energy value may be in calories or another unit of energy. The energy value may be based, in part, on information from the user profile 426, such as the age parameter 428, the gender parameter 430, the weight parameter 432, and the body composition parameter 434. In some examples, input from physiological sensors may be used to contribute to the energy value. For example, input from a heart rate monitor 440, an oximeter 442, a respiration meter 444, a surface electromyograph 446, a thermometer 448, another type of physiological sensor, or combinations thereof may be used to provide input for the energy value. Further, an accelerometer 450 may be used to confirm that the user is performing the exercise at the difficulty applied to the parameters of the exercise machine. For example, the user may be standing next to the exercise machine while the tread belt 122 rotates. In such an situation, the accelerometer 450 can indicate that the user is resting even though the tread belt 122 is rotating. Thus, the energy value may reflect that the user was not exercising at that time despite inputs from the exercise machine 100 indicating that the tread belt 122 is rotating. Further, if the programmed exercise routine instructs the user to perform push-ups off of the exercise machine, the accelerometer 450 may confirm that the user actually performed the push-ups as instructed by recording the user's movements as the user performs the exercises. Such physiological sensors and/or the accelerometer may be integrated into the exercise machine 100, the console 106, the arm rests 108, 110, the lower section 138 of the arm rests 108, 110, a mobile device 438, a device carried by the user, a remote device, or combinations thereof.

The programmed exercise routine 422 represents programmed instructions that, when executed, cause the processing resources 402 to vary the difficulty levels of the exercise machine's operating parameters to achieve a desired workout. In some instances, the programmed exercise routine 422 has segments where the program instructs the user to perform an activity off of the exercise machine 100 such as perform stretches, use a different exercise machine, perform other types of exercises off of the exercise machine 100, ingest food or liquid, perform another type of activity, or combinations thereof. The routine resumer 424 represents programmed instructions that, when executed, cause the processing resources 402 to cause the programmed exercise routine 422 to resume. In some instances, the user may have returned from getting off of the exercise machine either because the user followed a command from the programmed exercise routine 422 to perform a certain activity or because the user got off of the exercise machine 100 for a different reason.

Further, the memory resources 404 may be part of an installation package. In response to installing the installation package, the programmed instructions of the memory resources 404 may be downloaded from the installation package's source, such as a portable medium, a server, a remote network location, another location, or combinations thereof. Portable memory media that are compatible with the principles described herein include DVDs, CDs, flash memory, portable disks, magnetic disks, optical disks, other forms of portable memory, or combinations thereof. In other examples, the program instructions are already installed. Here, the memory resources 404 can include integrated memory such as a hard drive, a solid state hard drive or the like.

In some examples, the processing resources 402 and the memory resources 404 are located within the exercise machine 100, the console 106, the arm rests 108, 110 another portion of the exercise machine 100, a mobile device, an external device, another type of device, or combinations thereof. The memory resources 404 may be part of any of these device's main memory, caches, registers, non-volatile memory, or elsewhere in their memory hierarchy. Alternatively, the memory resources 404 may be in communication with the processing resources 402 over a network. Further, data structures, such as libraries or databases containing user and/or workout information, may be accessed from a remote location over a network connection while the programmed instructions are located locally. Thus, the exercise system 400 may be implemented with the exercise machine, a mobile device, a phone, an electronic tablet, a wearable computing device, a head mounted device, a server, a collection of servers, a networked device, a watch, or combinations thereof. Such an implementation may occur through input/output mechanisms, such as push buttons, touch screen buttons, voice commands, dials, levers, other types of input/output mechanisms, or combinations thereof. Any appropriate type of wearable device may be used. A non-exhaustive list of wearable devices may include glasses, arm bands, leg bands, torso bands, head bands, chest straps, wrist watches, belts, earrings, nose rings, other types of rings, necklaces, garment integrated devices, other types of devices, or combinations thereof.

While the examples above have been primarily described with reference to an exercise machine that includes a tread belt 122 as the movable element, other type of exercise machines with other types of movable elements may be used in accordance to the principles described herein. For example, the movable elements of other exercise machines may include foot pedals, flywheels, crankshafts, ski tracks, seats (i.e. such as seats in rowing machines or core machines), arm levers, other types of exercise machines, or combinations thereof.

Figure 5:
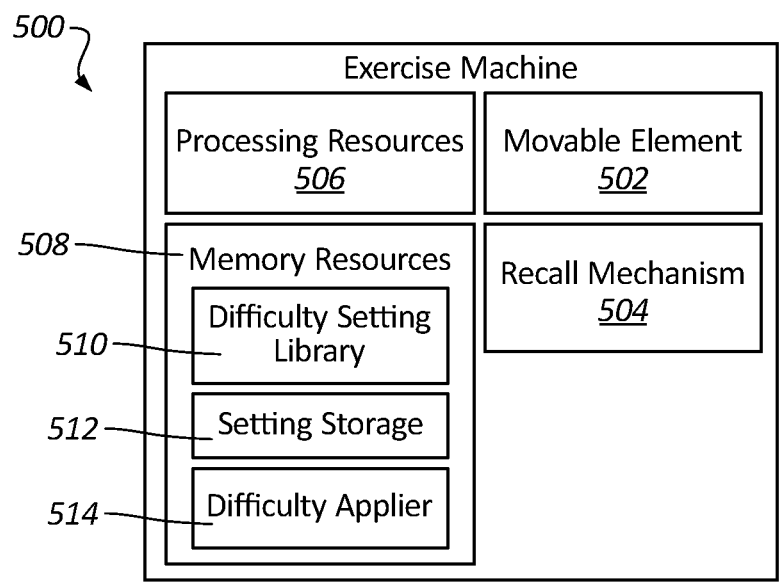
FIG. 5 illustrates a block diagram of an example of an exercise system in accordance with the present disclosure.

FIG. 5 depicts an exercise machine 500 with a movable element 502 that is movable in performance of an exercise. The movable element 502 has at least one selectively adjustable operating parameter that selectively alters a difficulty of the exercise. The exercise machine 500 also includes a recall mechanism 504. The exercise machine 500 also includes a processor 506 and memory 508. The memory 508 comprises programmed instructions executable by the processor 506 to apply a first difficulty setting of the at least one selectively adjustable operating parameter to the movable element 502. Such a difficulty setting may be selected from a difficulty setting library 510, and the difficulty setting may be applied with a difficulty applier 514. The programmed instructions may also cause the processor 506 to store the first difficulty setting in the memory 508. The applied difficulty setting may be stored in a setting storage 512. The programmed instructions may also include reapplying the difficulty setting with the difficulty 514 or another mechanism to the movable element based on activation of the recall mechanism 504.

Figure 6:
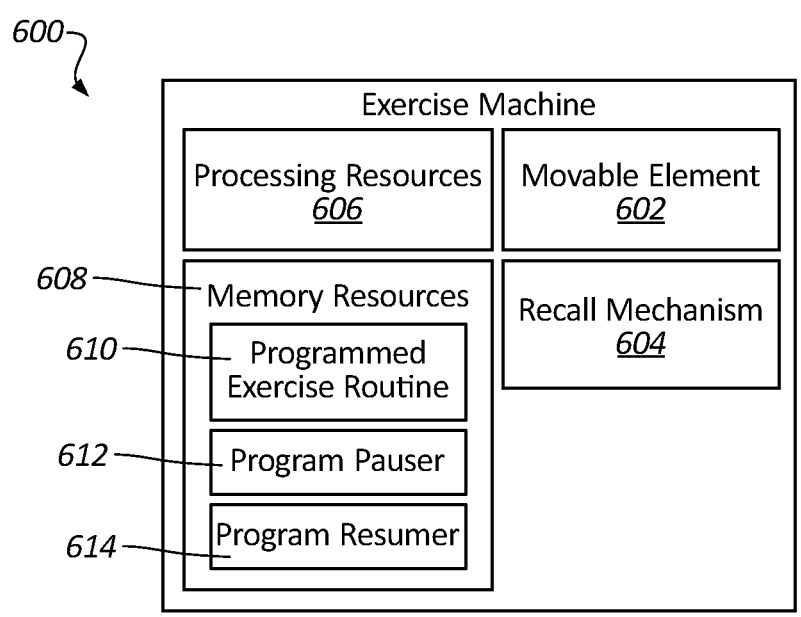
FIG. 6 illustrates a block diagram of an examples of an exercise system in accordance with the present disclosure.

FIG. 6 depicts an exercise machine 600 that has a movable element 602 that is movable in a performance of an exercise. The movable element 602 may have at least one selectively adjustable operating parameter that selectively alters a difficulty of the exercise. The exercise machine 600 may also include a recall mechanism connected to a frame. The exercise machine 600 may include a processor 606 and memory 608. The memory 608 may include programmed instructions executable by the processor 606 to execute a programmed exercise routine 610 that controls the at least one selectively operating parameter to the movable element 602, pause the programmed exercise routine 610, and resume the programmed exercise routine 610 based on activation of the recall mechanism 604.

Figure 7:
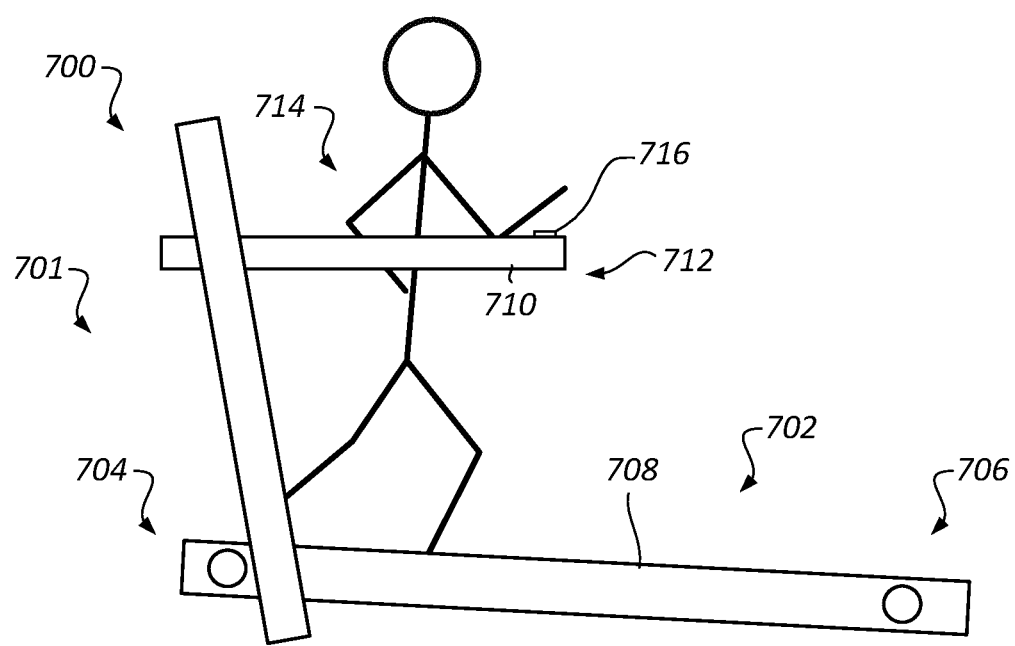
FIG. 7 illustrates an example of an exercise machine in accordance with the present disclosure.

FIG. 7 depicts an exercise machine 700 having a frame 701 and an exercise deck 702 attached to the frame 701. A tread belt is rotatably disposed about the exercise deck 702 between a front pulley 704 and rear pulley 706. A top surface 708 of the tread belt moves from the front pulley 704 to the rear pulley 706. The exercise machine 700 includes an arm rest 710 attached to the frame. A first section 712 of the arm rest 710 is positioned to be accessible to a user performing an exercise on the tread belt when a backside 714 of the user faces the front pulley 704, and a user input 716 integrated into the first section 712.

INDUSTRIAL APPLICABILITY

In general, the invention disclosed herein may provide the user with an ability to resume the previous difficulty settings on an exercise machine without having to re-input such difficulty settings. For example, a user may easily switch between different difficulty settings on the exercise machine during an interval workout by activating the recall mechanism to switch to the last used difficulty setting. In an interval workout the user may instruct the recall mechanism to switch to the intense interval setting by moving a toggle switch in the arm rest in a first direction and to switch to the lower difficulty setting by moving the toggle switch in the other direction. However, the recall mechanism may be activated to call the exercise machine to resume the same difficulty settings that were previously applied to the exercise machine before a user got off of the exercise machine. In some cases, the recall mechanism may store the exercise settings over a long period of time, so the user can use the recall mechanism to apply settings that the user applied during previous workouts. However, the user may use the recall mechanism to cause the exercise machine to apply the difficulty settings that were used earlier during the same workout.

In some cases, the user may instruct the exercise machine to store the difficulty settings. However, in other examples, the exercise machine may store each group of difficulty settings used by the user in temporary memory so that the user can return to the previous setting without instructing the exercise machine to store those specific settings. For example, the user may apply a first difficulty setting to the operating parameters of the exercise machine through the operations controller of the console and perform a workout at those difficulty settings for a time until the user desires to change the difficulty settings. After the user applies the second difficulty settings, the user may decide that he or she would rather workout at the first difficulty settings again. In such a circumstance, the user may activate the recall mechanism to cause the first difficulty settings to be applied to the exercise machine again. In such an example, the user does not have to remember the details about the first difficulty setting because the recall mechanism automatically returns the difficulty settings to the previous setting.

In some cases, the recall mechanism may be used for situations where the user is executing a programmed exercise routine with the exercise machine. In those instances where the user gets off of the exercise machine, either as part of the exercise routine or for another reason, the user can instruct the exercise machine to resume the operating parameters of the exercise machine at the previous difficulty settings or other settings in accordance with the programmed exercise routine. The user may be able to stop the exercise machine or at least some of the functions of the exercise machine with the stop mechanism. A user may desire to stop the exercise machine while the user completes other exercises off of the exercise machine and then return to the exercise machine as part of the workout without instructions from a programmed exercise routine.

The recall mechanism may be integrated into arm rests, a console, or another part of the exercise machine. In some cases, the recall mechanism is integrated into a portion of the exercise machine that is accessible to the user when the user is performing backward facing exercises. In such circumstances, the user may face the rear end of the exercise machine such that the user's back is facing the console of the exercise machine.

What is claimed is:

1. An exercise machine, comprising:
a frame;
a movable element that is movable in a performance of an exercise, the movable element having at least one selectively adjustable operating parameter that selectively alters a difficulty of the exercise;
a recall mechanism connected to the frame;
a processor and memory, the memory comprising programmed instructions executable by the processor to:
apply a first difficulty setting of the at least one selectively adjustable operating parameter to the movable element;
selectively store the first difficulty setting in the memory in response to store instructions from a user; and
reapply the first difficulty setting to the movable element based on activation of the recall mechanism.

2. The exercise machine of claim 1, wherein the movable element is a foot pedal or tread belt.

3. The exercise machine of claim 1, wherein the first difficulty setting is associated with an intensity level of an interval workout.

4. The exercise machine of claim 1, wherein the programmed instructions are further executable by the processor to change the difficulty to a second difficulty setting in response to activation of a toggle switch.

5. The exercise machine of claim 4, wherein the programmed instructions to change the difficulty to the second difficulty setting are executable by the processor in response to second command from an operation controller integrated into the exercise machine.

6. The exercise machine of claim 4, wherein the programmed instructions to change the difficulty to the second difficulty setting are executable by the processor in response to activation of a stop mechanism.

7. The exercise machine of claim 4, wherein the programmed instructions are further executable by the processor to change the difficulty back to the first difficulty setting from the second difficulty setting based on activation of the recall mechanism.

8. The exercise machine of claim 1, further comprising a console connected to the frame.

9. The exercise machine of claim 8, wherein an operation controller is integrated into the console.

10. An exercise machine, comprising:
a frame;
a movable element that is movable in a performance of an exercise, the movable element having at least one selectively adjustable operating parameter that selectively alters a difficulty of the exercise;
a console connected to the frame;
an operation controller integrated into the console;
a recall mechanism connected to the frame; and
a processor and memory, the memory comprising programmed instructions executable by the processor to:
apply a first difficulty setting of the at least one selectively adjustable operating parameter to the movable element based on a first command received through the operation controller;
selectively store the first difficulty setting in the memory in response to store instructions from a user;
change the difficulty to a second difficulty setting in response to user input; and
reapply the first difficulty setting from the second difficulty setting to the movable element based on activation of the recall mechanism.

11. The exercise machine of claim 10, wherein the programmed instructions to change the difficulty to the second difficulty setting are executable by the processor in response to a second command from the operation controller.

12. The exercise machine of claim 10, wherein the programmed instructions to change the difficulty to the second difficulty setting are executable by the processor in response to activation of a stop mechanism.

13. The exercise machine of claim 10, wherein the programmed instructions are further executable by the processor to change the difficulty to the second difficulty setting in response to activation of a toggle switch.

14. An exercise machine, comprising:
a frame;
a movable element that is movable in a performance of an exercise, the movable element having at least one selectively adjustable operating parameter that selectively alters a difficulty of the exercise;
a console connected to the frame;
an operation controller integrated into the console;
an arm rest connected to the frame, the arm rest having an upper section and a lower section where the lower section is spaced a shorter distance away from the movable element than the upper section;
a recall mechanism integrated into the lower section of the arm rest;
a stop mechanism connected to the frame;
a processor and memory, the memory comprising programmed instructions executable by the processor to:
apply a first difficulty setting of the at least one selectively adjustable operating parameter to the movable element based on a first command received through the operation controller;
selectively store the first difficulty setting in the memory in response to store instructions from a user;
change the difficulty to a second difficulty setting based on activation of the stop mechanism; and
reapply the first difficulty setting from the second difficulty setting to the movable element based on activation of the recall mechanism.

15. The exercise machine of claim 1, wherein the recall mechanism is connected to the frame remotely from a console for providing interval training.

16. The exercise machine of claim 1, wherein the instructions executable by the processor apply the first difficulty setting during at least a time period of a workout, selectively store the first difficulty setting in the memory in response to store instructions from the user for at least the time period of the workout but not permanently, and before ending the time period of the workout, reapply the first difficulty setting to the movable element based on activation of the recall mechanism.

17. The exercise machine of claim 1, wherein the activation of the recall mechanism is a single activation of the recall mechanism.

18. The exercise machine of claim 1, wherein the instructions executable by the processor store the first difficulty setting such that the activation of the recall mechanism applies the first difficulty setting to the movable element.

19. The exercise machine of claim 15, wherein the recall mechanism is integrated into an arm rest connected to the frame.

20. The exercise machine of claim 19, wherein the arm rest has an upper section that is elevated higher than a base portion of a console of the exercise machine and a lower section where the lower section is located at an elevation that is lower than the console and wherein the recall mechanism is integrated into the upper section or the lower section of the arm rest.

* * * * *